United States Patent
Stub Laursen et al.

(10) Patent No.: US 12,110,321 B2
(45) Date of Patent: Oct. 8, 2024

(54) SINGLE DOMAIN ANTIBODIES FOR COMPLEMENT REGULATION

(71) Applicant: Aarhus Universitet, Aarhus C (DK)

(72) Inventors: Nick Stub Laursen, Aarhus C (DK); Dennis Vestergaard Pedersen, Aarhus C (DK); Gregers Rom Andersen, Brabrand (DK); Steffen Thiel, Risskov (DK); Alessandra Zarantonello, Aarhus C (DK); Rasmus Kjeldsen Jensen, Aarhus C (DK); Henrik Pedersen, Aarhus C (DK)

(73) Assignee: Aarhus Universitet, Aarhus C (DK)

( * ) Notice: Subject to any disclaimer, the term of this patent is extended or adjusted under 35 U.S.C. 154(b) by 791 days.

(21) Appl. No.: 17/251,023

(22) PCT Filed: Jun. 11, 2019

(86) PCT No.: PCT/EP2019/065206
§ 371 (c)(1),
(2) Date: Dec. 10, 2020

(87) PCT Pub. No.: WO2019/238674
PCT Pub. Date: Dec. 19, 2019

(65) Prior Publication Data
US 2021/0253682 A1 Aug. 19, 2021

(30) Foreign Application Priority Data
Jun. 11, 2018 (EP) .................................. 18176954

(51) Int. Cl.
| | | |
|---|---|---|
| *C07K 16/00* | (2006.01) | |
| *A61P 35/00* | (2006.01) | |
| *C07K 16/18* | (2006.01) | |
| *C07K 16/46* | (2006.01) | |

(52) U.S. Cl.
CPC .............. *C07K 16/18* (2013.01); *A61P 35/00* (2018.01); *C07K 2317/31* (2013.01); *C07K 2317/33* (2013.01); *C07K 2317/34* (2013.01); *C07K 2317/565* (2013.01); *C07K 2317/569* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2010/0291106 A1* | 11/2010 | Etemad-Gilbertson | ..................... C07K 16/18 536/23.53 |
| 2011/0104156 A1 | 5/2011 | Christadoss et al. | |
| 2017/0212130 A1* | 7/2017 | Rout | ....................... C07K 16/44 |

FOREIGN PATENT DOCUMENTS

| | | |
|---|---|---|
| CA | 2862999 A1 | 7/2013 |
| WO | 2006/079372 A1 | 8/2006 |
| WO | 2008/154251 A2 | 12/2008 |
| WO | 2008/154251 A3 | 5/2009 |
| WO | 2008/154251 A4 | 7/2009 |
| WO | 2010/136311 A2 | 12/2010 |
| WO | 2010/136311 A3 | 5/2011 |
| WO | 2014/028560 A2 | 2/2014 |
| WO | 2015/006504 A1 | 1/2015 |

OTHER PUBLICATIONS

Laursen et al. Functional and Structural Characterization of a Potent C1q Inhibitor Targeting the Classical Pathway of the Complement System. Front. Immunol., Jul. 17, 2020. (Year: 2020).*
Brown et al. Tolerance of single, but not multiple, amino acid replacements in antibody VH CDR 2: a means of minimizing B cell wastage from somatic hypermutation? J. Immuno. May 1996, 3285-91. (Year: 1996).*
Vajdos et al. Comprehensive functional maps of the antigen-binding site of an anti-ErbB2 antibody obtained with shotgun scanning mutagenesis. J. Mol. Biol., Jul 5, 2002, 320(2):415-28. (Year: 2002).*
Hee Young Hwang et al.; Highly specific inhibition of C1q globular-head binding to human IgG: A novel approach to control and regulate the classical complement pathway using an engineered single chain antibody variable fragment; Molecular Immunology; vol. 45, Issue 9, May 2008, pp. 2570-2580.
Afonine, Pavel V., et al.: "Towards automated crystallographic structure refinement with phenix.refine", Acta Crystallogr D Biol Crystallogr. Apr. 2012;68(Pt 4):352-67.
Cruz, Jonathan W. et al..; "A novel bispecific antibody platform to direct complement activity for efficient lysis of target cells"; Scientific Reports; Published Aug. 19, 2019.
Emsley et al.: "Features and development of Coot", Acta Crystallogr D Biol Crystallogr. Apr. 2010; 66(Pt 4): 486-501.
Fryer, Jonathan P. et al; "Synthetic Peptides which inhibit the interaction between C1q and Immunoglubulin and progong Xenograft Survival"; Transplantation, vol. 70, 828-836, No. 5; Sep. 15, 2000.
Hsiung et al; "A Monoclonal Antibody which can distinguish between the two Isotypes of Human C4"; Molecular Immunology, vol. 24, No. 1, pp. 91-96; 1987.
Jensen, Rasmus K. et el; "A Potent complement factor C3 specific nanobody inhibiting multiple functions in the alternative pathway of human and murine complement"; J. Biol. Chem. (2018) 293(17) 6269-6281.

(Continued)

*Primary Examiner* — Maher M Haddad
(74) *Attorney, Agent, or Firm* — Greenberg Traurig, LLP

(57) ABSTRACT

Single domain antibodies are provided, which are capable of specifically binding to an epitope of a human complement factor selected from the group consisting of C1q, C3, C4 and/or the proteolytic derivatives C3b and C4b. Further the use of the antibodies are provided for methods in modulating the activity of the complement system as well 5 as methods of treating disorders associated with complement activation.

18 Claims, 25 Drawing Sheets

Specification includes a Sequence Listing.

(56) References Cited

OTHER PUBLICATIONS

Kabsch, W. "Integration, scaling, space-group assignment and post-refinement", Acta Crystallogr. D Biol. Crystallogr. 66, 133-144, 2010. ISSN 0907-4449, doi:10.1107/S0907444909047374.

Katschke; K. et al; "Structural and Functional Analysis of a C3b-specific Antibody That Selectively Inhibits the Alternative Pathway of Complement"; The Journal of Biological Chemistry, vol. 284, No. 16, 00 10473-10479, Apr. 17, 2009.

Kontermann et al.: "Complement recruitment using bispecific diabodies", Nature Biotechnology vol. 15, Jul. 1997, 629-31. doi: 10.1038/nbt0797-629.

Mccoy et al.: "Phaser crystallographic software", Journal of Applied Crystallography, Aug. 1, 2007;40(Pt4):658-674. Epub Jul. 13, 2007. doi:10.1107/S0021889807021206.

Moreau et al.: "Structural and Functional Characterization of a Single-Chain Form of the Recognition Domain of Complement Protein C1q", Frontiers in Immunology 2016, Mar 2; vol. 7, Article 79, doi:10.3389/fimmu.2016.00079.

Pardon, Els et al; "A general protocol for the generation of Nanobodies for structural biology"; Nature Protocols; vol. 9 No 3, Feb. 27, 2017.

Pilely, Katrine at al; A specific assay for quantification of human C4c by use of an anti-C4c monoclonal antibody; Journal of Immunological Methods; 405, 2014; 87-96.

Romão, Ema et al; "Identification of useful Nanobodies by Phage Display of Immuni Single Domain Libraries Derived from Camelid Heavy Chain Antibodies"; Current Pharmaceutical Design; 2016; 22,6500-6518.

Rossotti et al.: "Increasing the potency of neutralizing single-domain antibodies by functionalization with a CD11b/CD18 binding domain", MAbs. Sep.-Oct 2015; vol. 7 Issue 5: 820-828, doi:10.1080/19420862.2015.1068491.

Scheres, S.H: "Relion: implementation of a Bayesian approach to cryo-EM structure determination", Journal of Structural Biology Dec. 2012;180(3):519-30, doi: 10.1016/j.jsb.2012.09.006.

Suloway, C. et al.: "Automated molecular microscopy: the new Leginon system", Journal of Structural Biology 151, (2005) 41-60.

Voss, et al.: (2009) "DoG Picker and TiltPicker: software tools to facilitate particle selection in single particle electron microscopy", Journal of Structural Biology, 166, 205-213. doi:10.1016/j.jsb.2009.01.004.

Zarantonello, Alessandra et al; Two potent C4 and C4b nanobodies inhibiting the classical pathway of the complement system; Molecular Immunology 102, 2018, pp. 129-235.

Tenner, Andrea J., P. H. Lesavre, and N. R. Cooper. "Purification and radiolabeling of human C1q." Journal of immunology (Baltimore, Md.: 1950) 127.2 (1981): 648-653.

Van Audenhove, Isabel, and Jan Gettemans. "Nanobodies as versatile tools to understand, diagnose, visualize and treat cancer." EBioMedicine 8 (Apr. 2016): 40-48.

* cited by examiner

Figure 2C
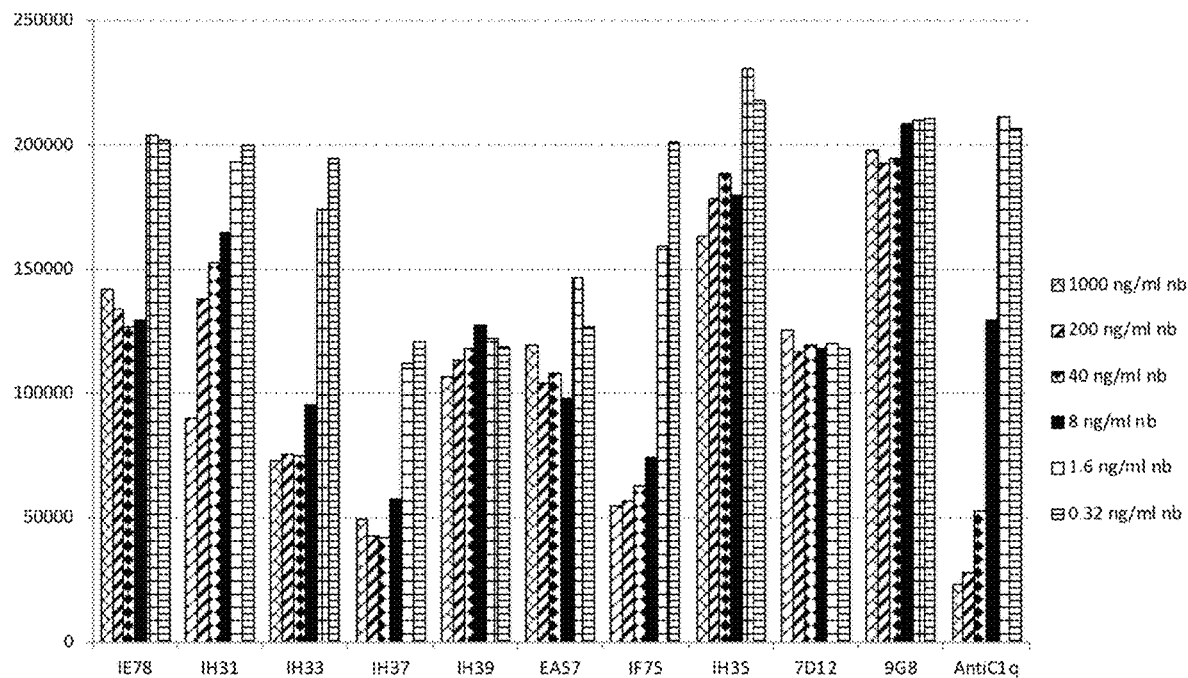
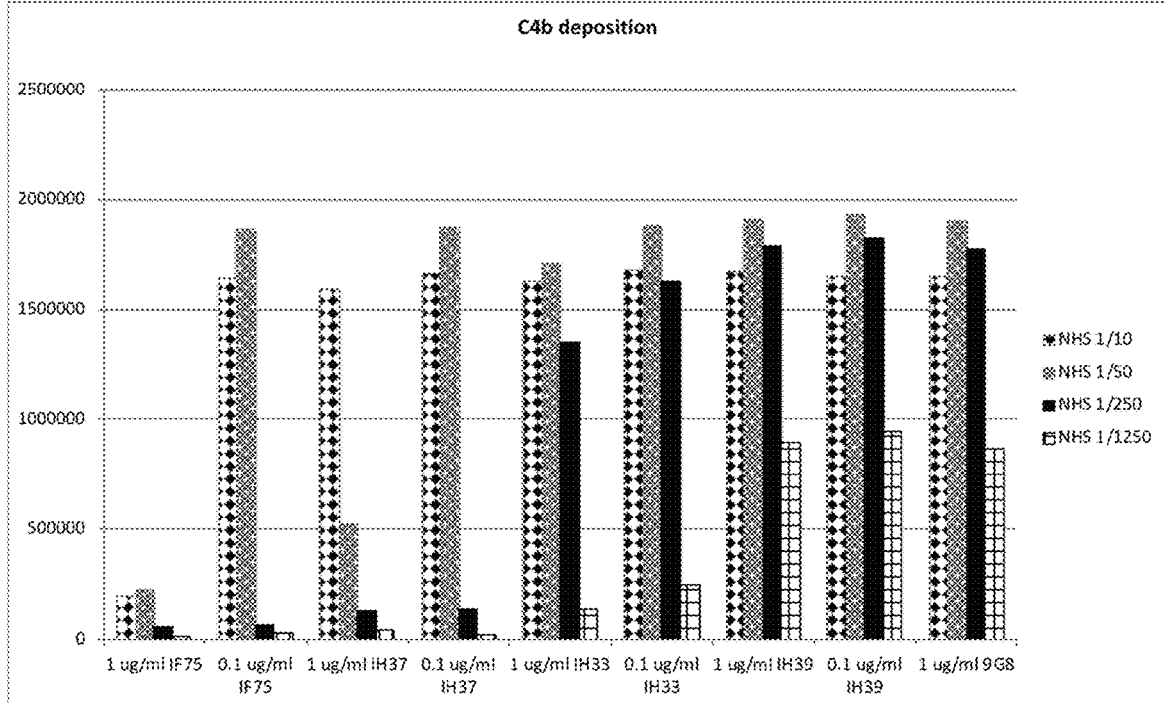
Figure 2D

Figure 4A
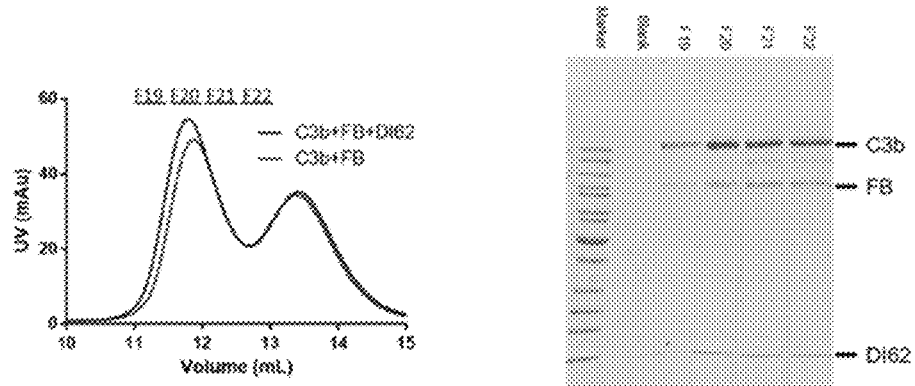
Figure 4B
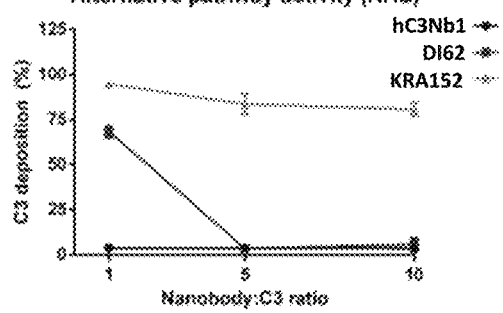
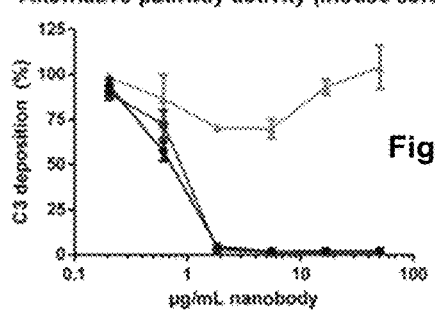
Figure 4C
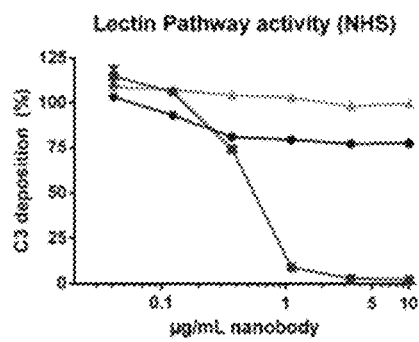
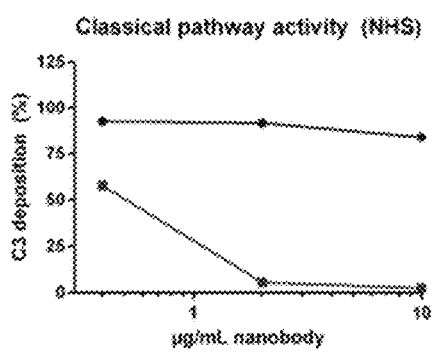
Figure 4D
Figure 4E

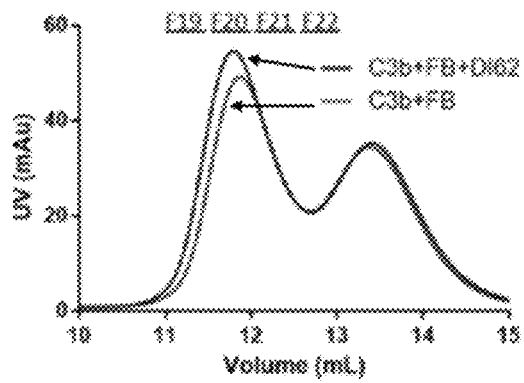
Figure 4F
Figure 5A
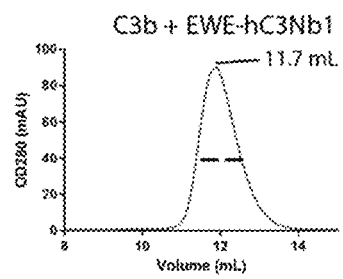
Figure 5B
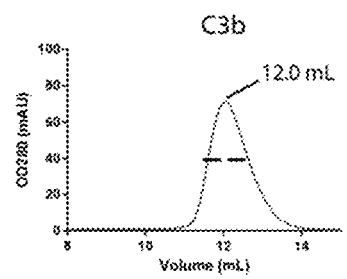
Figure 5C
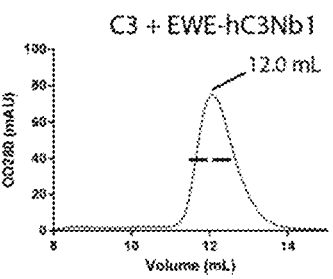
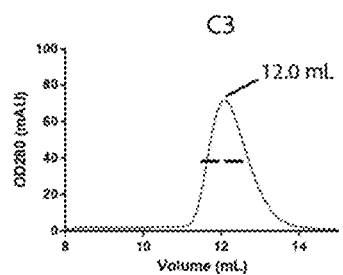
Figure 5D
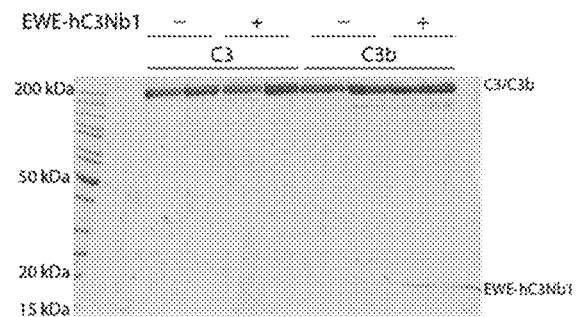
Figure 5E

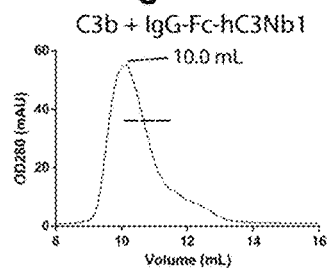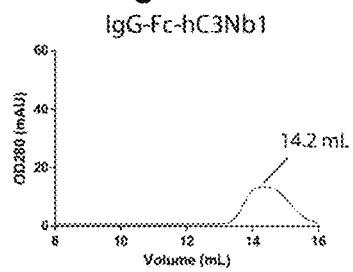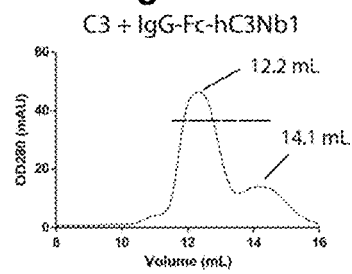
Figure 6A C3b + IgG-Fc-hC3Nb1
Figure 6B IgG-Fc-hC3Nb1
Figure 6C C3 + IgG-Fc-hC3Nb1
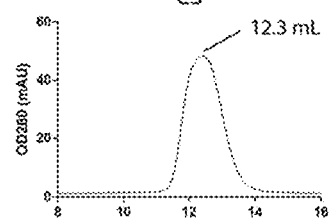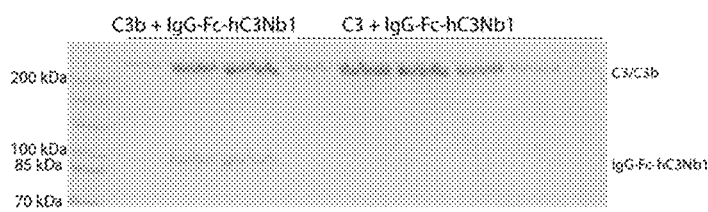
Figure 6D
Figure 6E
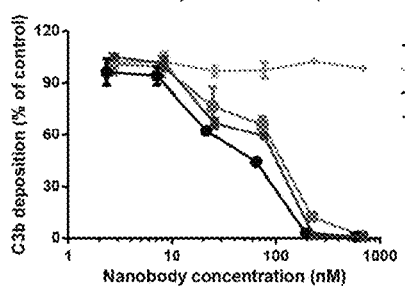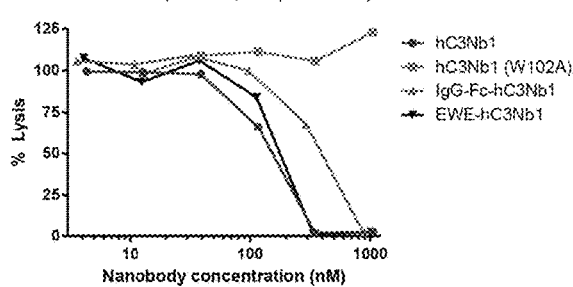
Figure 7A
Figure 7B

Figure 8A
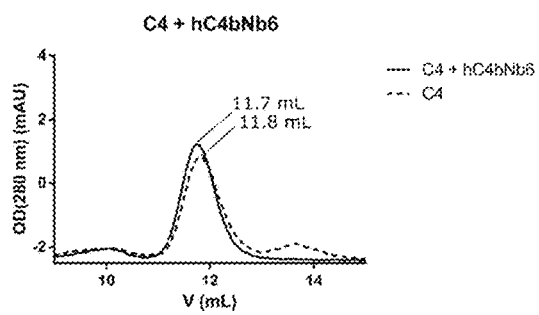
Figure 8B
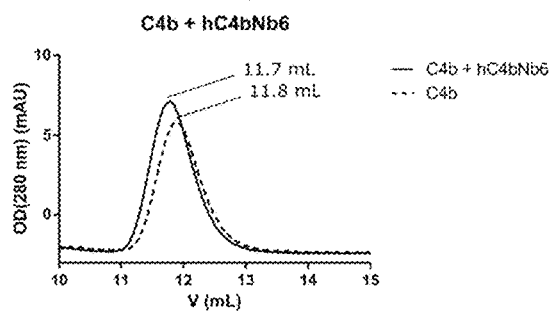
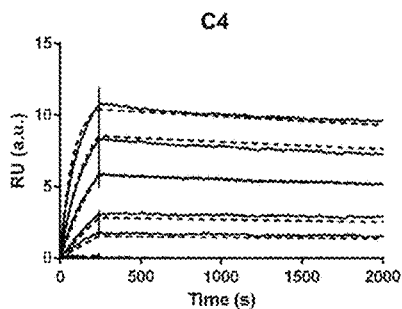
Figure 8C
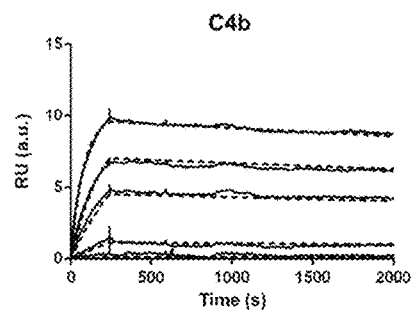
Figure 8D
| Analyte | $k_a$ (1/Ms) | $k_d$ (1/s) | $K_D$ (M) |
|---|---|---|---|
| C4 | $1.23 \cdot 10^5 \pm 0.04 \cdot 10^5$ | $5.7 \cdot 10^{-5} \pm 0.4 \cdot 10^{-5}$ | $4.6 \cdot 10^{-10} \pm 0.2 \cdot 10^{-10}$ |
| C4b | $5.3 \cdot 10^5 \pm 0.4 \cdot 10^5$ | $6.1 \cdot 10^{-5} \pm 0.6 \cdot 10^{-5}$ | $1.2 \cdot 10^{-10} \pm 0.2 \cdot 10^{-10}$ |
Figure 8E

Figure 12A
| Name | N-terminal | C-terminal |
|---|---|---|
| BiCE161 | IF75 | MU1053 |
| DF85 | IF75 | 7D12 |
| DH38 | IH31 | 7D12 |
| DF90 | IH35 | 7D12 |
| IA74 | EA57 | 7D12 |
| BiCE128 | DF85 | 9G8 |
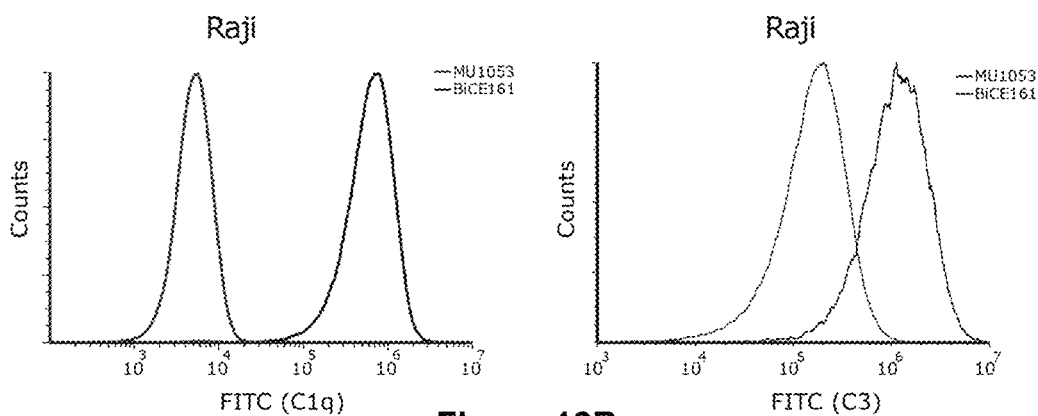
Figure 12B
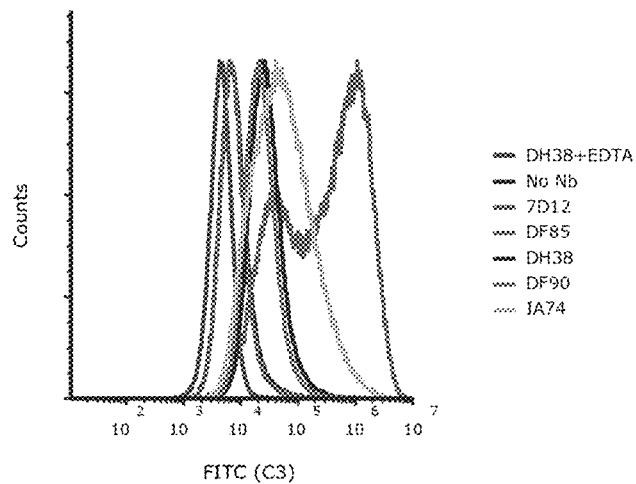
Figure 12C Figure 12D
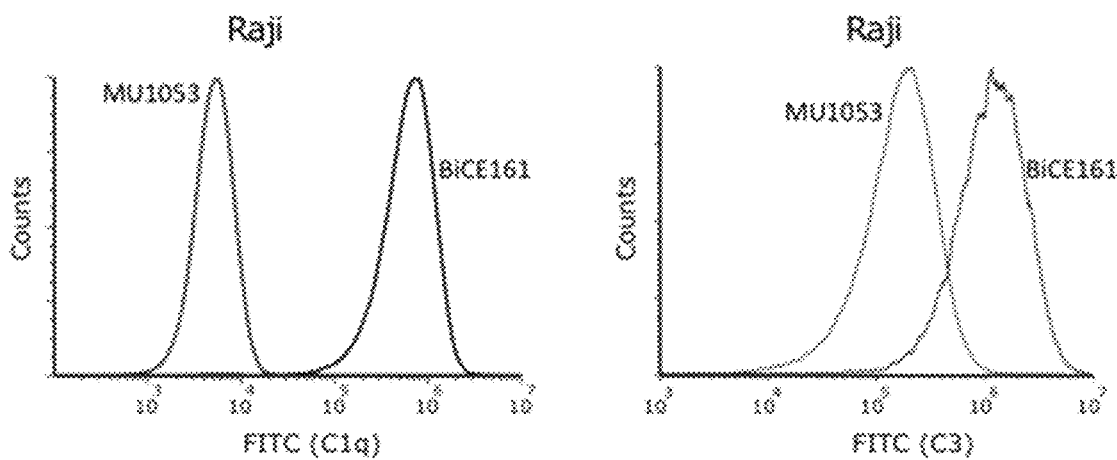
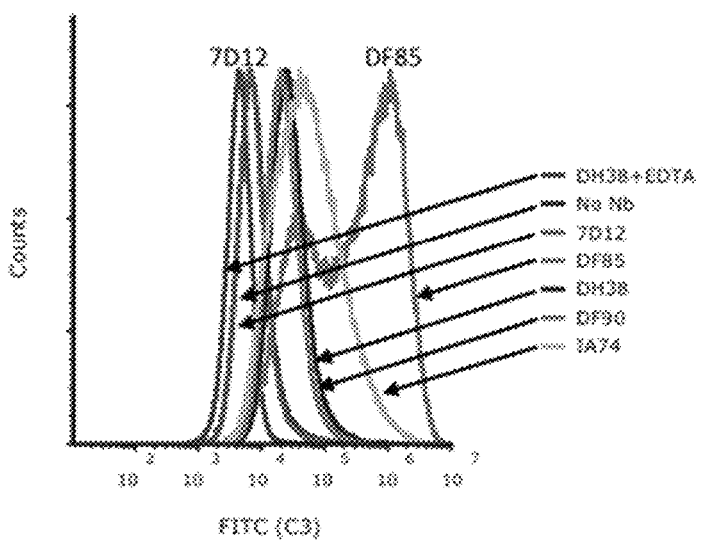
Figure 12E Figure 13A
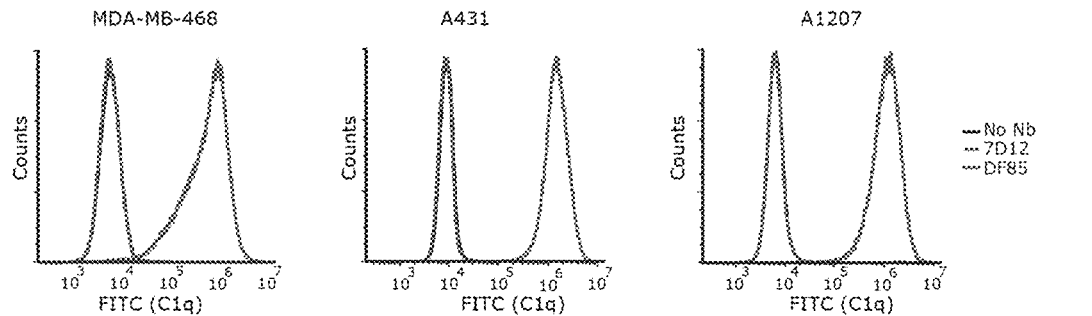
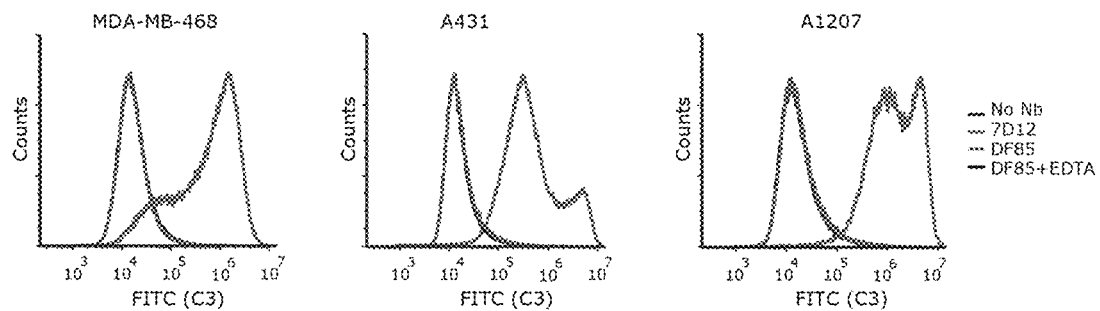
Figure 13B
Figure 13C
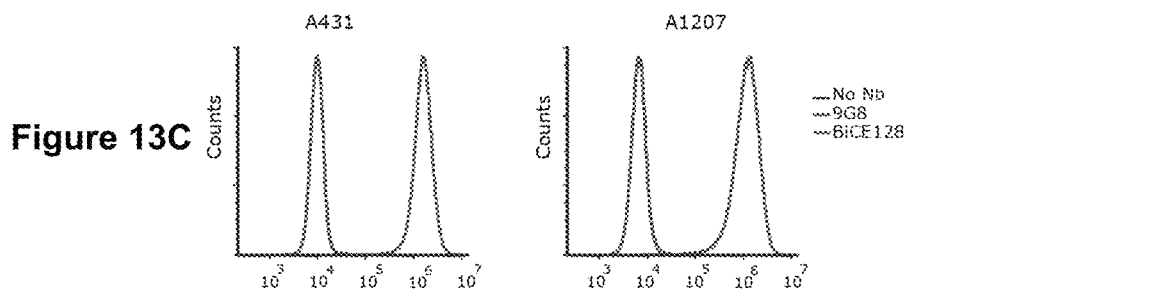
Figure 13D
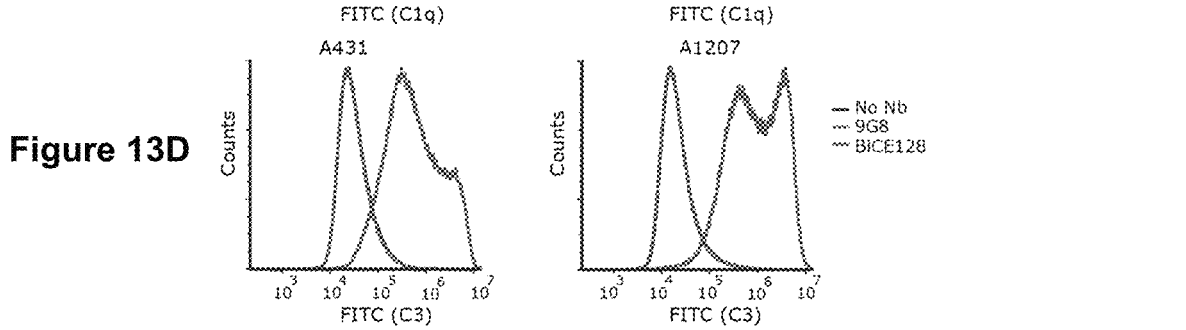

Figure 13E
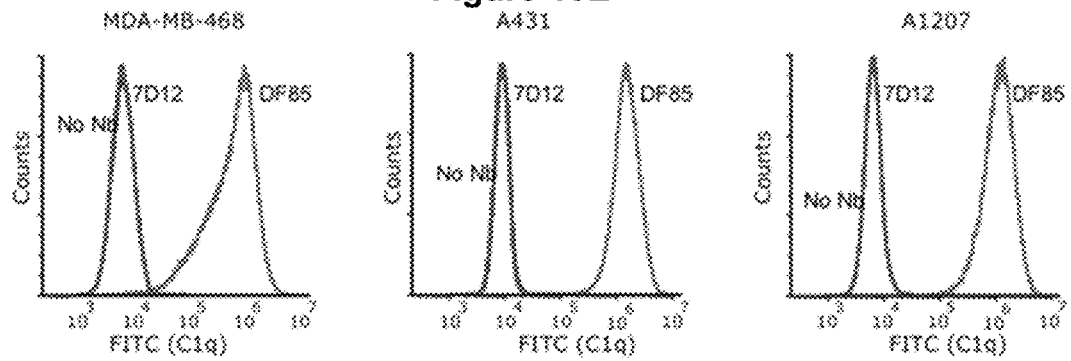
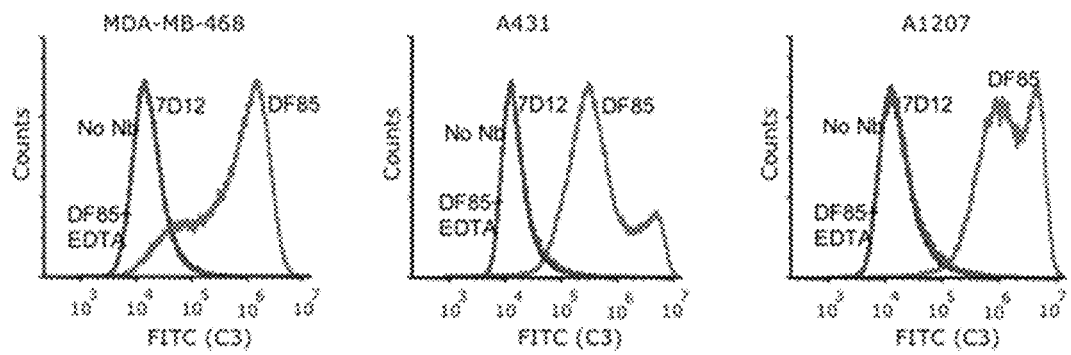
Figure 13F
Figure 13G
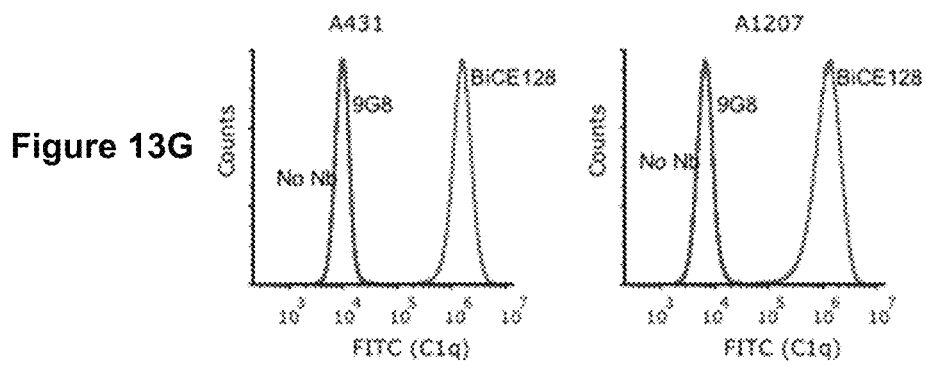
Figure 13H
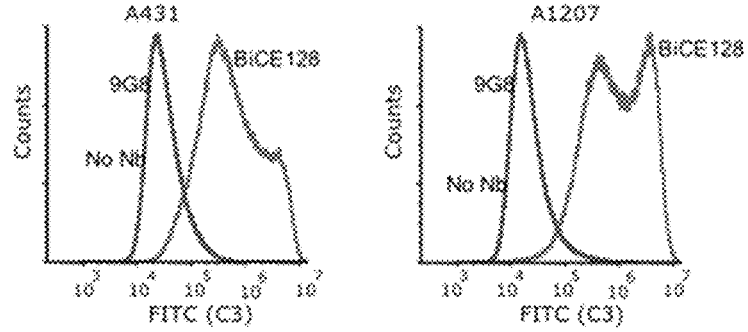

SEQUENCE LISTING

<160> NUMBER OF SEQ ID NOS: 85

<210> SEQ ID NO 1
<211> LENGTH: 1641
<212> TYPE: PRT
<213> ORGANISM: Homo sapiens

<400> SEQUENCE: 1

Ser Pro Met Tyr Ser Ile Ile Thr Pro Asn Ile Leu Arg Leu Glu Ser
1               5                   10                  15

Glu Glu Thr Met Val Leu Glu Ala His Asp Ala Gln Gly Asp Val Pro
            20                  25                  30

Val Thr Val Thr Val His Asp Phe Pro Gly Lys Lys Leu Val Leu Ser
        35                  40                  45

Ser Glu Lys Thr Val Leu Thr Pro Ala Thr Asn His Met Gly Asn Val
    50                  55                  60

Thr Phe Thr Ile Pro Ala Asn Arg Glu Phe Lys Ser Glu Lys Gly Arg
65                  70                  75                  80

Asn Lys Phe Val Thr Val Gln Ala Thr Phe Gly Thr Gln Val Val Glu
                85                  90                  95

Lys Val Val Leu Val Ser Leu Gln Ser Gly Tyr Leu Phe Ile Gln Thr
            100                 105                 110

Asp Lys Thr Ile Tyr Thr Pro Gly Ser Thr Val Leu Tyr Arg Ile Phe
        115                 120                 125

Thr Val Asn His Lys Leu Leu Pro Val Gly Arg Thr Val Met Val Asn
    130                 135                 140

Ile Glu Asn Pro Glu Gly Ile Pro Val Lys Gln Asp Ser Leu Ser Ser
145                 150                 155                 160

```
Gln Asn Gln Leu Gly Val Leu Pro Leu Ser Trp Asp Ile Pro Glu Leu
            165                 170                 175
Val Asn Met Gly Gln Trp Lys Ile Arg Ala Tyr Tyr Glu Asn Ser Pro
        180                 185                 190
Gln Gln Val Phe Ser Thr Glu Phe Glu Val Lys Glu Tyr Val Leu Pro
        195                 200                 205
Ser Phe Glu Val Ile Val Glu Pro Thr Glu Lys Phe Tyr Tyr Ile Tyr
        210                 215                 220
Asn Glu Lys Gly Leu Glu Val Thr Ile Thr Ala Arg Phe Leu Tyr Gly
225                 230                 235                 240
Lys Lys Val Glu Gly Thr Ala Phe Val Ile Phe Gly Ile Gln Asp Gly
                245                 250                 255
Glu Gln Arg Ile Ser Leu Pro Glu Ser Leu Lys Arg Ile Pro Ile Glu
                260                 265                 270
Asp Gly Ser Gly Glu Val Val Leu Ser Arg Lys Val Leu Leu Asp Gly
            275                 280                 285
Val Gln Asn Pro Arg Ala Glu Asp Leu Val Gly Lys Ser Leu Tyr Val
        290                 295                 300
Ser Ala Thr Val Ile Leu His Ser Gly Ser Asp Met Val Gln Ala Glu
305                 310                 315                 320
Arg Ser Gly Ile Pro Ile Val Thr Ser Pro Tyr Gln Ile His Phe Thr
                325                 330                 335
Lys Thr Pro Lys Tyr Phe Lys Pro Gly Met Pro Phe Asp Leu Met Val
                340                 345                 350
Phe Val Thr Asn Pro Asp Gly Ser Pro Ala Tyr Arg Val Pro Val Ala
            355                 360                 365
Val Gln Gly Glu Asp Thr Val Gln Ser Leu Thr Gln Gly Asp Gly Val
        370                 375                 380
Ala Lys Leu Ser Ile Asn Thr His Pro Ser Gln Lys Pro Leu Ser Ile
385                 390                 395                 400
Thr Val Arg Thr Lys Lys Gln Glu Leu Ser Glu Ala Glu Gln Ala Thr
                405                 410                 415
Arg Thr Met Gln Ala Leu Pro Tyr Ser Thr Val Gly Asn Ser Asn Asn
            420                 425                 430
Tyr Leu His Leu Ser Val Leu Arg Thr Glu Leu Arg Pro Gly Glu Thr
        435                 440                 445
Leu Asn Val Asn Phe Leu Leu Arg Met Asp Arg Ala His Glu Ala Lys
    450                 455                 460
Ile Arg Tyr Tyr Thr Tyr Leu Ile Met Asn Lys Gly Arg Leu Leu Lys
465                 470                 475                 480
Ala Gly Arg Gln Val Arg Glu Pro Gly Gln Asp Leu Val Val Leu Pro
                485                 490                 495
Leu Ser Ile Thr Thr Asp Phe Ile Pro Ser Phe Arg Leu Val Ala Tyr
            500                 505                 510
Tyr Thr Leu Ile Gly Ala Ser Gly Gln Arg Glu Val Val Ala Asp Ser
        515                 520                 525
Val Trp Val Asp Val Lys Asp Ser Cys Val Gly Ser Leu Val Val Lys
        530                 535                 540
Ser Gly Gln Ser Glu Asp Arg Gln Pro Val Pro Gly Gln Gln Met Thr
545                 550                 555                 560
Leu Lys Ile Glu Gly Asp His Gly Ala Arg Val Val Leu Val Ala Val
                565                 570                 575
Asp Lys Gly Val Phe Val Leu Asn Lys Lys Asn Lys Leu Thr Gln Ser
```

```
              580                 585                 590
Lys Ile Trp Asp Val Val Glu Lys Ala Asp Ile Gly Cys Thr Pro Gly
            595                 600                 605

Ser Gly Lys Asp Tyr Ala Gly Val Phe Ser Asp Ala Gly Leu Thr Phe
610                 615                 620

Thr Ser Ser Ser Gly Gln Gln Thr Ala Gln Arg Ala Glu Leu Gln Cys
625                 630                 635                 640

Pro Gln Pro Ala Ala Arg Arg Arg Ser Val Gln Leu Thr Glu Lys
                645                 650                 655

Arg Met Asp Lys Val Gly Lys Tyr Pro Lys Glu Leu Arg Lys Cys Cys
            660                 665                 670

Glu Asp Gly Met Arg Glu Asn Pro Met Arg Phe Ser Cys Gln Arg Arg
            675                 680                 685

Thr Arg Phe Ile Ser Leu Gly Glu Ala Cys Lys Lys Val Phe Leu Asp
            690                 695                 700

Cys Cys Asn Tyr Ile Thr Glu Leu Arg Arg Gln His Ala Arg Ala Ser
705                 710                 715                 720

His Leu Gly Leu Ala Arg Ser Asn Leu Asp Glu Asp Ile Ile Ala Glu
                725                 730                 735

Glu Asn Ile Val Ser Arg Ser Glu Phe Pro Glu Ser Trp Leu Trp Asn
                740                 745                 750

Val Glu Asp Leu Lys Glu Pro Pro Lys Asn Gly Ile Ser Thr Lys Leu
            755                 760                 765

Met Asn Ile Phe Leu Lys Asp Ser Ile Thr Thr Trp Glu Ile Leu Ala
            770                 775                 780

Val Ser Met Ser Asp Lys Lys Gly Ile Cys Val Ala Asp Pro Phe Glu
785                 790                 795                 800

Val Thr Val Met Gln Asp Phe Phe Ile Asp Leu Arg Leu Pro Tyr Ser
                805                 810                 815

Val Val Arg Asn Glu Gln Val Glu Ile Arg Ala Val Leu Tyr Asn Tyr
                820                 825                 830

Arg Gln Asn Gln Glu Leu Lys Val Arg Val Glu Leu Leu His Asn Pro
            835                 840                 845

Ala Phe Cys Ser Leu Ala Thr Thr Lys Arg Arg His Gln Gln Thr Val
            850                 855                 860

Thr Ile Pro Pro Lys Ser Ser Leu Ser Val Pro Tyr Val Ile Val Pro
865                 870                 875                 880

Leu Lys Thr Gly Leu Gln Glu Val Glu Val Lys Ala Ala Val Tyr His
                885                 890                 895

His Phe Ile Ser Asp Gly Val Arg Lys Ser Leu Lys Val Val Pro Glu
                900                 905                 910

Gly Ile Arg Met Asn Lys Thr Val Ala Val Arg Thr Leu Asp Pro Glu
            915                 920                 925

Arg Leu Gly Arg Glu Gly Val Gln Lys Glu Asp Ile Pro Pro Ala Asp
            930                 935                 940

Leu Ser Asp Gln Val Pro Asp Thr Glu Ser Glu Thr Arg Ile Leu Leu
945                 950                 955                 960

Gln Gly Thr Pro Val Ala Gln Met Thr Glu Asp Ala Val Asp Ala Glu
                965                 970                 975

Arg Leu Lys His Leu Ile Val Thr Pro Ser Gly Cys Gly Glu Gln Asn
            980                 985                 990

Met Ile Gly Met Thr Pro Thr Val  Ile Ala Val His Tyr  Leu Asp Glu
            995                 1000                1005
```

-continued

```
Thr Glu Gln Trp Glu Lys Phe Gly Leu Glu Lys Arg Gln Gly Ala
1010            1015                1020

Leu Glu Leu Ile Lys Lys Gly Tyr Thr Gln Leu Ala Phe Arg
1025            1030                1035

Gln Pro Ser Ser Ala Phe Ala Ala Phe Val Lys Arg Ala Pro Ser
1040            1045                1050

Thr Trp Leu Thr Ala Tyr Val Val Lys Val Phe Ser Leu Ala Val
1055            1060                1065

Asn Leu Ile Ala Ile Asp Ser Gln Val Leu Cys Gly Ala Val Lys
1070            1075                1080

Trp Leu Ile Leu Glu Lys Gln Lys Pro Asp Gly Val Phe Gln Glu
1085            1090                1095

Asp Ala Pro Val Ile His Gln Glu Met Ile Gly Gly Leu Arg Asn
1100            1105                1110

Asn Asn Glu Lys Asp Met Ala Leu Thr Ala Phe Val Leu Ile Ser
1115            1120                1125

Leu Gln Glu Ala Lys Asp Ile Cys Glu Glu Gln Val Asn Ser Leu
1130            1135                1140

Pro Gly Ser Ile Thr Lys Ala Gly Asp Phe Leu Glu Ala Asn Tyr
1145            1150                1155

Met Asn Leu Gln Arg Ser Tyr Thr Val Ala Ile Ala Gly Tyr Ala
1160            1165                1170

Leu Ala Gln Met Gly Arg Leu Lys Gly Pro Leu Leu Asn Lys Phe
1175            1180                1185

Leu Thr Thr Ala Lys Asp Lys Asn Arg Trp Glu Asp Pro Gly Lys
1190            1195                1200

Gln Leu Tyr Asn Val Glu Ala Thr Ser Tyr Ala Leu Leu Ala Leu
1205            1210                1215

Leu Gln Leu Lys Asp Phe Asp Phe Val Pro Pro Val Val Arg Trp
1220            1225                1230

Leu Asn Glu Gln Arg Tyr Tyr Gly Gly Gly Tyr Gly Ser Thr Gln
1235            1240                1245

Ala Thr Phe Met Val Phe Gln Ala Leu Ala Gln Tyr Gln Lys Asp
1250            1255                1260

Ala Pro Asp His Gln Glu Leu Asn Leu Asp Val Ser Leu Gln Leu
1265            1270                1275

Pro Ser Arg Ser Ser Lys Ile Thr His Arg Ile His Trp Glu Ser
1280            1285                1290

Ala Ser Leu Leu Arg Ser Glu Glu Thr Lys Glu Asn Glu Gly Phe
1295            1300                1305

Thr Val Thr Ala Glu Gly Lys Gly Gln Gly Thr Leu Ser Val Val
1310            1315                1320

Thr Met Tyr His Ala Lys Ala Lys Asp Gln Leu Thr Cys Asn Lys
1325            1330                1335

Phe Asp Leu Lys Val Thr Ile Lys Pro Ala Pro Glu Thr Glu Lys
1340            1345                1350

Arg Pro Gln Asp Ala Lys Asn Thr Met Ile Leu Glu Ile Cys Thr
1355            1360                1365

Arg Tyr Arg Gly Asp Gln Asp Ala Thr Met Ser Ile Leu Asp Ile
1370            1375                1380

Ser Met Met Thr Gly Phe Ala Pro Asp Thr Asp Asp Leu Lys Gln
1385            1390                1395
```

```
Leu Ala Asn Gly Val Asp Arg Tyr Ile Ser Lys Tyr Glu Leu Asp
    1400                1405                1410

Lys Ala Phe Ser Asp Arg Asn Thr Leu Ile Ile Tyr Leu Asp Lys
    1415                1420                1425

Val Ser His Ser Glu Asp Asp Cys Leu Ala Phe Lys Val His Gln
    1430                1435                1440

Tyr Phe Asn Val Glu Leu Ile Gln Pro Gly Ala Val Lys Val Tyr
    1445                1450                1455

Ala Tyr Tyr Asn Leu Glu Glu Ser Cys Thr Arg Phe Tyr His Pro
    1460                1465                1470

Glu Lys Glu Asp Gly Lys Leu Asn Lys Leu Cys Arg Asp Glu Leu
    1475                1480                1485

Cys Arg Cys Ala Glu Glu Asn Cys Phe Ile Gln Lys Ser Asp Asp
    1490                1495                1500

Lys Val Thr Leu Glu Glu Arg Leu Asp Lys Ala Cys Glu Pro Gly
    1505                1510                1515

Val Asp Tyr Val Tyr Lys Thr Arg Leu Val Lys Val Gln Leu Ser
    1520                1525                1530

Asn Asp Phe Asp Glu Tyr Ile Met Ala Ile Glu Gln Thr Ile Lys
    1535                1540                1545

Ser Gly Ser Asp Glu Val Gln Val Gly Gln Gln Arg Thr Phe Ile
    1550                1555                1560

Ser Pro Ile Lys Cys Arg Glu Ala Leu Lys Leu Glu Lys Lys
    1565                1570                1575

His Tyr Leu Met Trp Gly Leu Ser Ser Asp Phe Trp Gly Glu Lys
    1580                1585                1590

Pro Asn Leu Ser Tyr Ile Ile Gly Lys Asp Thr Trp Val Glu His
    1595                1600                1605

Trp Pro Glu Glu Asp Glu Cys Gln Asp Glu Glu Asn Gln Lys Gln
    1610                1615                1620

Cys Gln Asp Leu Gly Ala Phe Thr Glu Ser Met Val Val Phe Gly
    1625                1630                1635

Cys Pro Asn
    1640

<210> SEQ ID NO 2
<211> LENGTH: 1635
<212> TYPE: PRT
<213> ORGANISM: Mus musculus

<400> SEQUENCE: 2

Ile Pro Met Tyr Ser Ile Ile Thr Pro Asn Val Leu Arg Leu Glu Ser
1               5                   10                  15

Glu Glu Thr Ile Val Leu Glu Ala His Asp Ala Gln Gly Asp Ile Pro
                20                  25                  30

Val Thr Val Thr Val Gln Asp Phe Leu Lys Arg Gln Val Leu Thr Ser
            35                  40                  45

Glu Lys Thr Val Leu Thr Gly Ala Ser Gly His Leu Arg Ser Val Ser
        50                  55                  60

Ile Lys Ile Pro Ala Ser Lys Glu Phe Asn Ser Asp Lys Glu Gly His
65                  70                  75                  80

Lys Tyr Val Thr Val Val Ala Asn Phe Gly Glu Thr Val Val Glu Lys
                85                  90                  95

Ala Val Met Val Ser Phe Gln Ser Gly Tyr Leu Phe Ile Gln Thr Asp
                100                 105                 110
```

```
Lys Thr Ile Tyr Thr Pro Gly Ser Thr Val Leu Tyr Arg Ile Phe Thr
            115                 120                 125

Val Asp Asn Asn Leu Leu Pro Val Gly Lys Thr Val Ile Leu Ile
130                 135                 140

Glu Thr Pro Asp Gly Ile Pro Val Lys Arg Asp Ile Leu Ser Ser Asn
145                 150                 155                 160

Asn Gln His Gly Ile Leu Pro Leu Ser Trp Asn Ile Pro Glu Leu Val
                165                 170                 175

Asn Met Gly Gln Trp Lys Ile Arg Ala Phe Tyr Glu His Ala Pro Lys
            180                 185                 190

Gln Ile Phe Ser Ala Glu Phe Glu Val Lys Glu Tyr Val Leu Pro Ser
        195                 200                 205

Phe Glu Val Arg Val Glu Pro Thr Glu Thr Phe Tyr Tyr Ile Asp Asp
    210                 215                 220

Pro Asn Gly Leu Glu Val Ser Ile Ile Ala Lys Phe Leu Tyr Gly Lys
225                 230                 235                 240

Asn Val Asp Gly Thr Ala Phe Val Ile Phe Gly Val Gln Asp Gly Asp
                245                 250                 255

Lys Lys Ile Ser Leu Ala His Ser Leu Thr Arg Val Val Ile Glu Asp
            260                 265                 270

Gly Val Gly Asp Ala Val Leu Thr Arg Lys Val Leu Met Glu Gly Val
        275                 280                 285

Arg Pro Ser Asn Ala Asp Ala Leu Val Gly Lys Ser Leu Tyr Val Ser
    290                 295                 300

Val Thr Val Ile Leu His Ser Gly Ser Asp Met Val Glu Ala Glu Arg
305                 310                 315                 320

Ser Gly Ile Pro Ile Val Thr Ser Pro Tyr Gln Ile His Phe Thr Lys
                325                 330                 335

Thr Pro Lys Phe Phe Lys Pro Ala Met Pro Phe Asp Leu Met Val Phe
            340                 345                 350

Val Thr Asn Pro Asp Gly Ser Pro Ala Ser Lys Val Leu Val Val Thr
        355                 360                 365

Gln Gly Ser Asn Ala Lys Ala Leu Thr Gln Asp Asp Gly Val Ala Lys
    370                 375                 380

Leu Ser Ile Asn Thr Pro Asn Ser Arg Gln Pro Leu Thr Ile Thr Val
385                 390                 395                 400

Arg Thr Lys Lys Asp Thr Leu Pro Glu Ser Arg Gln Ala Thr Lys Thr
                405                 410                 415

Met Glu Ala His Pro Tyr Ser Thr Met His Asn Ser Asn Asn Tyr Leu
            420                 425                 430

His Leu Ser Val Ser Arg Met Glu Leu Lys Pro Gly Asp Asn Leu Asn
        435                 440                 445

Val Asn Phe His Leu Arg Thr Asp Pro Gly His Glu Ala Lys Ile Arg
    450                 455                 460

Tyr Tyr Thr Tyr Leu Val Met Asn Lys Gly Lys Leu Leu Lys Ala Gly
465                 470                 475                 480

Arg Gln Val Arg Glu Pro Gly Gln Asp Leu Val Val Leu Ser Leu Pro
                485                 490                 495

Ile Thr Pro Glu Phe Ile Pro Ser Phe Arg Leu Val Ala Tyr Tyr Thr
            500                 505                 510

Leu Ile Gly Ala Ser Gly Gln Arg Glu Val Val Ala Asp Ser Val Trp
        515                 520                 525
```

-continued

Val Asp Val Lys Asp Ser Cys Ile Gly Thr Leu Val Lys Gly Asp
    530                 535                 540

Pro Arg Asp Asn His Leu Ala Pro Gly Gln Gln Thr Thr Leu Arg Ile
545                 550                 555                 560

Glu Gly Asn Gln Gly Ala Arg Val Gly Leu Val Ala Val Asp Lys Gly
                565                 570                 575

Val Phe Val Leu Asn Lys Lys Asn Lys Leu Thr Gln Ser Lys Ile Trp
            580                 585                 590

Asp Val Val Glu Lys Ala Asp Ile Gly Cys Thr Pro Gly Ser Gly Lys
        595                 600                 605

Asn Tyr Ala Gly Val Phe Met Asp Ala Gly Leu Ala Phe Lys Thr Ser
    610                 615                 620

Gln Gly Leu Gln Thr Glu Gln Arg Ala Asp Leu Glu Cys Thr Lys Pro
625                 630                 635                 640

Ala Ala Ser Val Gln Leu Met Glu Arg Arg Met Asp Lys Ala Gly Gln
                645                 650                 655

Tyr Thr Asp Lys Gly Leu Arg Lys Cys Cys Glu Asp Gly Met Arg Asp
            660                 665                 670

Ile Pro Met Arg Tyr Ser Cys Gln Arg Ala Arg Leu Ile Thr Gln
        675                 680                 685

Gly Glu Asn Cys Ile Lys Ala Phe Ile Asp Cys Cys Asn His Ile Thr
    690                 695                 700

Lys Leu Arg Glu Gln His Arg Arg Asp His Val Leu Gly Leu Ala Arg
705                 710                 715                 720

Ser Glu Leu Glu Glu Asp Ile Ile Pro Glu Glu Asp Ile Ile Ser Arg
                725                 730                 735

Ser His Phe Pro Gln Ser Trp Leu Trp Thr Ile Glu Glu Leu Lys Glu
            740                 745                 750

Pro Glu Lys Asn Gly Ile Ser Thr Lys Val Met Asn Ile Phe Leu Lys
        755                 760                 765

Asp Ser Ile Thr Thr Trp Glu Ile Leu Ala Val Ser Leu Ser Asp Lys
    770                 775                 780

Lys Gly Ile Cys Val Ala Asp Pro Tyr Glu Ile Arg Val Met Gln Asp
785                 790                 795                 800

Phe Phe Ile Asp Leu Arg Leu Pro Tyr Ser Val Val Arg Asn Glu Gln
                805                 810                 815

Val Glu Ile Arg Ala Val Leu Phe Asn Tyr Arg Glu Gln Glu Glu Leu
            820                 825                 830

Lys Val Arg Val Glu Leu Leu His Asn Pro Ala Phe Cys Ser Met Ala
        835                 840                 845

Thr Ala Lys Asn Arg Tyr Phe Gln Thr Ile Lys Ile Pro Pro Lys Ser
    850                 855                 860

Ser Val Ala Val Pro Tyr Val Ile Val Pro Leu Lys Ile Gly Gln Gln
865                 870                 875                 880

Glu Val Glu Val Lys Ala Ala Val Phe Asn His Phe Ile Ser Asp Gly
                885                 890                 895

Val Lys Lys Thr Leu Lys Val Val Pro Glu Gly Met Arg Ile Asn Lys
            900                 905                 910

Thr Val Ala Ile His Thr Leu Asp Pro Glu Lys Leu Gly Gln Gly Gly
        915                 920                 925

Val Gln Lys Val Asp Val Pro Ala Ala Asp Leu Ser Asp Gln Val Pro
    930                 935                 940

Asp Thr Asp Ser Glu Thr Arg Ile Ile Leu Gln Gly Ser Pro Val Val

-continued

```
945                 950                 955                 960
Gln Met Ala Glu Asp Ala Val Asp Gly Glu Arg Leu Lys His Leu Ile
                965                 970                 975
Val Thr Pro Ala Gly Cys Gly Glu Gln Asn Met Ile Gly Met Thr Pro
                980                 985                 990
Thr Val Ile Ala Val His Tyr Leu Asp Gln Thr Glu Gln Trp Glu Lys
                995                 1000                1005
Phe Gly Ile Glu Lys Arg Gln Glu Ala Leu Glu Leu Ile Lys Lys
    1010                1015                1020
Gly Tyr Thr Gln Gln Leu Ala Phe Lys Gln Pro Ser Ser Ala Tyr
    1025                1030                1035
Ala Ala Phe Asn Asn Arg Pro Pro Ser Thr Trp Leu Thr Ala Tyr
    1040                1045                1050
Val Val Lys Val Phe Ser Leu Ala Ala Asn Leu Ile Ala Ile Asp
    1055                1060                1065
Ser His Val Leu Cys Gly Ala Val Lys Trp Leu Ile Leu Glu Lys
    1070                1075                1080
Gln Lys Pro Asp Gly Val Phe Gln Glu Asp Gly Pro Val Ile His
    1085                1090                1095
Gln Glu Met Ile Gly Gly Phe Arg Asn Ala Lys Glu Ala Asp Val
    1100                1105                1110
Ser Leu Thr Ala Phe Val Leu Ile Ala Leu Gln Glu Ala Arg Asp
    1115                1120                1125
Ile Cys Glu Gly Gln Val Asn Ser Leu Pro Gly Ser Ile Asn Lys
    1130                1135                1140
Ala Gly Glu Tyr Ile Glu Ala Ser Tyr Met Asn Leu Gln Arg Pro
    1145                1150                1155
Tyr Thr Val Ala Ile Ala Gly Tyr Ala Leu Ala Leu Met Asn Lys
    1160                1165                1170
Leu Glu Glu Pro Tyr Leu Gly Lys Phe Leu Asn Thr Ala Lys Asp
    1175                1180                1185
Arg Asn Arg Trp Glu Glu Pro Asp Gln Gln Leu Tyr Asn Val Glu
    1190                1195                1200
Ala Thr Ser Tyr Ala Leu Leu Ala Leu Leu Leu Lys Asp Phe
    1205                1210                1215
Asp Ser Val Pro Pro Val Val Arg Trp Leu Asn Glu Gln Arg Tyr
    1220                1225                1230
Tyr Gly Gly Gly Tyr Gly Ser Thr Gln Ala Thr Phe Met Val Phe
    1235                1240                1245
Gln Ala Leu Ala Gln Tyr Gln Thr Asp Val Pro Asp His Lys Asp
    1250                1255                1260
Leu Asn Met Asp Val Ser Phe His Leu Pro Ser Arg Ser Ser Ala
    1265                1270                1275
Thr Thr Phe Arg Leu Leu Trp Glu Asn Gly Asn Leu Leu Arg Ser
    1280                1285                1290
Glu Glu Thr Lys Gln Asn Glu Ala Phe Ser Leu Thr Ala Lys Gly
    1295                1300                1305
Lys Gly Arg Gly Thr Leu Ser Val Val Ala Val Tyr His Ala Lys
    1310                1315                1320
Leu Lys Ser Lys Val Thr Cys Lys Lys Phe Asp Leu Arg Val Ser
    1325                1330                1335
Ile Arg Pro Ala Pro Glu Thr Ala Lys Lys Pro Glu Glu Ala Lys
    1340                1345                1350
```

Asn Thr Met Phe Leu Glu Ile Cys Thr Lys Tyr Leu Gly Asp Val
1355                1360                1365

Asp Ala Thr Met Ser Ile Leu Asp Ile Ser Met Met Thr Gly Phe
1370                1375                1380

Ala Pro Asp Thr Lys Asp Leu Glu Leu Leu Ala Ser Gly Val Asp
1385                1390                1395

Arg Tyr Ile Ser Lys Tyr Glu Met Asn Lys Ala Phe Ser Asn Lys
1400                1405                1410

Asn Thr Leu Ile Ile Tyr Leu Glu Lys Ile Ser His Thr Glu Glu
1415                1420                1425

Asp Cys Leu Thr Phe Lys Val His Gln Tyr Phe Asn Val Gly Leu
1430                1435                1440

Ile Gln Pro Gly Ser Val Lys Val Tyr Ser Tyr Tyr Asn Leu Glu
1445                1450                1455

Glu Ser Cys Thr Arg Phe Tyr His Pro Glu Lys Asp Asp Gly Met
1460                1465                1470

Leu Ser Lys Leu Cys His Ser Glu Met Cys Arg Cys Ala Glu Glu
1475                1480                1485

Asn Cys Phe Met Gln Gln Ser Gln Glu Lys Ile Asn Leu Asn Val
1490                1495                1500

Arg Leu Asp Lys Ala Cys Glu Pro Gly Val Asp Tyr Val Tyr Lys
1505                1510                1515

Thr Glu Leu Thr Asn Ile Glu Leu Leu Asp Asp Phe Asp Glu Tyr
1520                1525                1530

Thr Met Thr Ile Gln Gln Val Ile Lys Ser Gly Ser Asp Glu Val
1535                1540                1545

Gln Ala Gly Gln Gln Arg Lys Phe Ile Ser His Ile Lys Cys Arg
1550                1555                1560

Asn Ala Leu Lys Leu Gln Lys Gly Lys Lys Tyr Leu Met Trp Gly
1565                1570                1575

Leu Ser Ser Asp Leu Trp Gly Glu Lys Pro Asn Thr Ser Tyr Ile
1580                1585                1590

Ile Gly Lys Asp Thr Trp Val Glu His Trp Pro Glu Ala Glu Glu
1595                1600                1605

Cys Gln Asp Gln Lys Tyr Gln Lys Gln Cys Glu Glu Leu Gly Ala
1610                1615                1620

Phe Thr Glu Ser Met Val Val Tyr Gly Cys Pro Asn
1625                1630                1635

<210> SEQ ID NO 3
<211> LENGTH: 223
<212> TYPE: PRT
<213> ORGANISM: Homo sapiens

<400> SEQUENCE: 3

Glu Asp Leu Cys Arg Ala Pro Asp Gly Lys Lys Gly Glu Ala Gly
1               5                   10                  15

Pro Gly Arg Arg Gly Arg Pro Gly Leu Lys Gly Glu Gln Gly Pro
                20                  25                  30

Gly Ala Pro Gly Ile Arg Thr Gly Ile Gln Gly Leu Lys Gly Asp Gln
                35                  40                  45

Gly Glu Pro Gly Pro Ser Gly Asn Pro Gly Lys Val Gly Tyr Pro Gly
                50                  55                  60

Pro Ser Gly Pro Leu Gly Ala Arg Gly Ile Pro Gly Ile Lys Gly Thr

```
                65                  70                  75                  80
Lys Gly Ser Pro Gly Asn Ile Lys Asp Gln Pro Arg Pro Ala Phe Ser
                    85                  90                  95

Ala Ile Arg Arg Asn Pro Pro Met Gly Gly Asn Val Val Ile Phe Asp
                100                 105                 110

Thr Val Ile Thr Asn Gln Glu Glu Pro Tyr Gln Asn His Ser Gly Arg
                115                 120                 125

Phe Val Cys Thr Val Pro Gly Tyr Tyr Tyr Phe Thr Phe Gln Val Leu
            130                 135                 140

Ser Gln Trp Glu Ile Cys Leu Ser Ile Val Ser Ser Arg Gly Gln
145                 150                 155                 160

Val Arg Arg Ser Leu Gly Phe Cys Asp Thr Thr Asn Lys Gly Leu Phe
                165                 170                 175

Gln Val Val Ser Gly Gly Met Val Leu Gln Leu Gln Gln Gly Asp Gln
            180                 185                 190

Val Trp Val Glu Lys Asp Pro Lys Lys Gly His Ile Tyr Gln Gly Ser
            195                 200                 205

Glu Ala Asp Ser Val Phe Ser Gly Phe Leu Ile Phe Pro Ser Ala
    210                 215                 220

<210> SEQ ID NO 4
<211> LENGTH: 226
<212> TYPE: PRT
<213> ORGANISM: Homo sapiens

<400> SEQUENCE: 4

Gln Leu Ser Cys Thr Gly Pro Pro Ala Ile Pro Gly Ile Pro Gly Ile
1               5                   10                  15

Pro Gly Thr Pro Gly Pro Asp Gly Gln Pro Gly Thr Pro Gly Ile Lys
            20                  25                  30

Gly Glu Lys Gly Leu Pro Gly Leu Ala Gly Asp His Gly Glu Phe Gly
        35                  40                  45

Glu Lys Gly Asp Pro Gly Ile Pro Gly Asn Pro Gly Lys Val Gly Pro
    50                  55                  60

Lys Gly Pro Met Gly Pro Lys Gly Gly Pro Gly Ala Pro Gly Ala Pro
65                  70                  75                  80

Gly Pro Lys Gly Glu Ser Gly Asp Tyr Lys Ala Thr Gln Lys Ile Ala
                85                  90                  95

Phe Ser Ala Thr Arg Thr Ile Asn Val Pro Leu Arg Arg Asp Gln Thr
                100                 105                 110

Ile Arg Phe Asp His Val Ile Thr Asn Met Asn Asn Asn Tyr Glu Pro
            115                 120                 125

Arg Ser Gly Lys Phe Thr Cys Lys Val Pro Gly Leu Tyr Tyr Phe Thr
    130                 135                 140

Tyr His Ala Ser Ser Arg Gly Asn Leu Cys Val Asn Leu Met Arg Gly
145                 150                 155                 160

Arg Glu Arg Ala Gln Lys Val Val Thr Phe Cys Asp Tyr Ala Tyr Asn
                165                 170                 175

Thr Phe Gln Val Thr Thr Gly Gly Met Val Leu Lys Leu Glu Gln Gly
            180                 185                 190

Glu Asn Val Phe Leu Gln Ala Thr Asp Lys Asn Ser Leu Leu Gly Met
        195                 200                 205

Glu Gly Ala Asn Ser Ile Phe Ser Gly Phe Leu Leu Phe Pro Asp Met
    210                 215                 220
```

```
Glu Ala
225
```

<210> SEQ ID NO 5
<211> LENGTH: 217
<212> TYPE: PRT
<213> ORGANISM: Homo sapiens

<400> SEQUENCE: 5

```
Asn Thr Gly Cys Tyr Gly Ile Pro Gly Met Pro Gly Leu Pro Gly Ala
1               5                   10                  15

Pro Gly Lys Asp Gly Tyr Asp Gly Leu Pro Gly Pro Lys Gly Glu Pro
            20                  25                  30

Gly Ile Pro Ala Ile Pro Gly Ile Arg Gly Pro Lys Gly Gln Lys Gly
        35                  40                  45

Glu Pro Gly Leu Pro Gly His Pro Gly Lys Asn Gly Pro Met Gly Pro
    50                  55                  60

Pro Gly Met Pro Gly Val Pro Gly Pro Met Gly Ile Pro Gly Glu Pro
65                  70                  75                  80

Gly Glu Glu Gly Arg Tyr Lys Gln Lys Phe Gln Ser Val Phe Thr Val
                85                  90                  95

Thr Arg Gln Thr His Gln Pro Pro Ala Pro Asn Ser Leu Ile Arg Phe
            100                 105                 110

Asn Ala Val Leu Thr Asn Pro Gln Gly Asp Tyr Asp Thr Ser Thr Gly
        115                 120                 125

Lys Phe Thr Cys Lys Val Pro Gly Leu Tyr Tyr Phe Val Tyr His Ala
    130                 135                 140

Ser His Thr Ala Asn Leu Cys Val Leu Leu Tyr Arg Ser Gly Val Lys
145                 150                 155                 160

Val Val Thr Phe Cys Gly His Thr Ser Lys Thr Asn Gln Val Asn Ser
                165                 170                 175

Gly Gly Val Leu Leu Arg Leu Gln Val Gly Glu Glu Val Trp Leu Ala
            180                 185                 190

Val Asn Asp Tyr Tyr Asp Met Val Gly Ile Gln Gly Ser Asp Ser Val
        195                 200                 205

Phe Ser Gly Phe Leu Leu Phe Pro Asp
    210                 215
```

<210> SEQ ID NO 6
<211> LENGTH: 767
<212> TYPE: PRT
<213> ORGANISM: Homo sapiens

<400> SEQUENCE: 6

```
Asn Val Asn Phe Gln Lys Ala Ile Asn Glu Lys Leu Gly Gln Tyr Ala
1               5                   10                  15

Ser Pro Thr Ala Lys Arg Cys Cys Gln Asp Gly Val Thr Arg Leu Pro
            20                  25                  30

Met Met Arg Ser Cys Glu Gln Arg Ala Ala Arg Val Gln Gln Pro Asp
        35                  40                  45

Cys Arg Glu Pro Phe Leu Ser Cys Cys Gln Phe Ala Glu Ser Leu Arg
    50                  55                  60

Lys Lys Ser Arg Asp Lys Gly Gln Ala Gly Leu Gln Arg Ala Leu Glu
65                  70                  75                  80

Ile Leu Gln Glu Glu Asp Leu Ile Asp Glu Asp Ile Pro Val Arg
                85                  90                  95
```

```
Ser Phe Phe Pro Glu Asn Trp Leu Trp Arg Val Glu Thr Val Asp Arg
            100                 105                 110

Phe Gln Ile Leu Thr Leu Trp Leu Pro Asp Ser Leu Thr Thr Trp Glu
        115                 120                 125

Ile His Gly Leu Ser Leu Ser Lys Thr Lys Gly Leu Cys Val Ala Thr
    130                 135                 140

Pro Val Gln Leu Arg Val Phe Arg Glu Phe His Leu His Leu Arg Leu
145                 150                 155                 160

Pro Met Ser Val Arg Arg Phe Glu Gln Leu Glu Leu Arg Pro Val Leu
                165                 170                 175

Tyr Asn Tyr Leu Asp Lys Asn Leu Thr Val Ser Val His Val Ser Pro
            180                 185                 190

Val Glu Gly Leu Cys Leu Ala Gly Gly Gly Leu Ala Gln Gln Val
        195                 200                 205

Leu Val Pro Ala Gly Ser Ala Arg Pro Val Ala Phe Ser Val Val Pro
    210                 215                 220

Thr Ala Ala Ala Val Ser Leu Lys Val Val Ala Arg Gly Ser Phe
225                 230                 235                 240

Glu Phe Pro Val Gly Asp Ala Val Ser Lys Val Leu Gln Ile Glu Lys
                245                 250                 255

Glu Gly Ala Ile His Arg Glu Glu Leu Val Tyr Glu Leu Asn Pro Leu
            260                 265                 270

Asp His Arg Gly Arg Thr Leu Glu Ile Pro Gly Asn Ser Asp Pro Asn
        275                 280                 285

Met Ile Pro Asp Gly Asp Phe Asn Ser Tyr Val Arg Val Thr Ala Ser
    290                 295                 300

Asp Pro Leu Asp Thr Leu Gly Ser Glu Gly Ala Leu Ser Pro Gly Gly
305                 310                 315                 320

Val Ala Ser Leu Leu Arg Leu Pro Arg Gly Cys Gly Glu Gln Thr Met
                325                 330                 335

Ile Tyr Leu Ala Pro Thr Leu Ala Ala Ser Arg Tyr Leu Asp Lys Thr
            340                 345                 350

Glu Gln Trp Ser Thr Leu Pro Pro Glu Thr Lys Asp His Ala Val Asp
        355                 360                 365

Leu Ile Gln Lys Gly Tyr Met Arg Ile Gln Gln Phe Arg Lys Ala Asp
    370                 375                 380

Gly Ser Tyr Ala Ala Trp Leu Ser Arg Asp Ser Ser Thr Trp Leu Thr
385                 390                 395                 400

Ala Phe Val Leu Lys Val Leu Ser Leu Ala Gln Glu Gln Val Gly Gly
                405                 410                 415

Ser Pro Glu Lys Leu Gln Glu Thr Ser Asn Trp Leu Leu Ser Gln Gln
            420                 425                 430

Gln Ala Asp Gly Ser Phe Gln Asp Pro Cys Pro Val Leu Asp Arg Ser
        435                 440                 445

Met Gln Gly Gly Leu Val Gly Asn Asp Glu Thr Val Ala Leu Thr Ala
    450                 455                 460

Phe Val Thr Ile Ala Leu His His Gly Leu Ala Val Phe Gln Asp Glu
465                 470                 475                 480

Gly Ala Glu Pro Leu Lys Gln Arg Val Glu Ala Ser Ile Ser Lys Ala
                485                 490                 495

Asn Ser Phe Leu Gly Glu Lys Ala Ser Ala Gly Leu Leu Gly Ala His
            500                 505                 510

Ala Ala Ala Ile Thr Ala Tyr Ala Leu Thr Leu Thr Lys Ala Pro Val
```

```
            515                 520                 525

Asp Leu Leu Gly Val Ala His Asn Asn Leu Met Ala Met Ala Gln Glu
            530                 535                 540

Thr Gly Asp Asn Leu Tyr Trp Gly Ser Val Thr Gly Ser Gln Ser Asn
545                 550                 555                 560

Ala Val Ser Pro Thr Pro Ala Pro Arg Asn Pro Ser Asp Pro Met Pro
                565                 570                 575

Gln Ala Pro Ala Leu Trp Ile Glu Thr Thr Ala Tyr Ala Leu Leu His
            580                 585                 590

Leu Leu Leu His Glu Gly Lys Ala Glu Met Ala Asp Gln Ala Ser Ala
            595                 600                 605

Trp Leu Thr Arg Gln Gly Ser Phe Gln Gly Gly Phe Arg Ser Thr Gln
            610                 615                 620

Asp Thr Val Ile Ala Leu Asp Ala Leu Ser Ala Tyr Trp Ile Ala Ser
625                 630                 635                 640

His Thr Thr Glu Glu Arg Gly Leu Asn Val Thr Leu Ser Ser Thr Gly
                645                 650                 655

Arg Asn Gly Phe Lys Ser His Ala Leu Gln Leu Asn Asn Arg Gln Ile
            660                 665                 670

Arg Gly Leu Glu Glu Glu Leu Gln Phe Ser Leu Gly Ser Lys Ile Asn
            675                 680                 685

Val Lys Val Gly Gly Asn Ser Lys Gly Thr Leu Lys Val Leu Arg Thr
690                 695                 700

Tyr Asn Val Leu Asp Met Lys Asn Thr Thr Cys Gln Asp Leu Gln Ile
705                 710                 715                 720

Glu Val Thr Val Lys Gly His Val Glu Tyr Thr Met Glu Ala Asn Glu
                725                 730                 735

Asp Tyr Glu Asp Tyr Glu Tyr Asp Glu Leu Pro Ala Lys Asp Asp Pro
            740                 745                 750

Asp Ala Pro Leu Gln Pro Val Thr Pro Leu Gln Leu Phe Glu Gly
            755                 760                 765

<210> SEQ ID NO 7
<211> LENGTH: 656
<212> TYPE: PRT
<213> ORGANISM: Homo sapiens

<400> SEQUENCE: 7

Lys Pro Arg Leu Leu Leu Phe Ser Pro Ser Val Val His Leu Gly Val
1               5                   10                  15

Pro Leu Ser Val Gly Val Gln Leu Gln Asp Val Pro Arg Gly Gln Val
            20                  25                  30

Val Lys Gly Ser Val Phe Leu Arg Asn Pro Ser Arg Asn Asn Val Pro
        35                  40                  45

Cys Ser Pro Lys Val Asp Phe Thr Leu Ser Ser Glu Arg Asp Phe Ala
    50                  55                  60

Leu Leu Ser Leu Gln Val Pro Leu Lys Asp Ala Lys Ser Cys Gly Leu
65                  70                  75                  80

His Gln Leu Leu Arg Gly Pro Glu Val Gln Leu Val Ala His Ser Pro
                85                  90                  95

Trp Leu Lys Asp Ser Leu Ser Arg Thr Thr Asn Ile Gln Gly Ile Asn
            100                 105                 110

Leu Leu Phe Ser Ser Arg Arg Gly His Leu Phe Leu Gln Thr Asp Gln
        115                 120                 125
```

-continued

Pro Ile Tyr Asn Pro Gly Gln Arg Val Arg Tyr Arg Val Phe Ala Leu
130                 135                 140

Asp Gln Lys Met Arg Pro Ser Thr Asp Thr Ile Thr Val Met Val Glu
145                 150                 155                 160

Asn Ser His Gly Leu Arg Val Arg Lys Lys Glu Val Tyr Met Pro Ser
                165                 170                 175

Ser Ile Phe Gln Asp Asp Phe Val Ile Pro Asp Ile Ser Glu Pro Gly
            180                 185                 190

Thr Trp Lys Ile Ser Ala Arg Phe Ser Asp Gly Leu Glu Ser Asn Ser
        195                 200                 205

Ser Thr Gln Phe Glu Val Lys Lys Tyr Val Leu Pro Asn Phe Glu Val
210                 215                 220

Lys Ile Thr Pro Gly Lys Pro Tyr Ile Leu Thr Val Pro Gly His Leu
225                 230                 235                 240

Asp Glu Met Gln Leu Asp Ile Gln Ala Arg Tyr Ile Tyr Gly Lys Pro
                245                 250                 255

Val Gln Gly Val Ala Tyr Val Arg Phe Gly Leu Leu Asp Glu Asp Gly
            260                 265                 270

Lys Lys Thr Phe Phe Arg Gly Leu Glu Ser Gln Thr Lys Leu Val Asn
        275                 280                 285

Gly Gln Ser His Ile Ser Leu Ser Lys Ala Glu Phe Gln Asp Ala Leu
290                 295                 300

Glu Lys Leu Asn Met Gly Ile Thr Asp Leu Gln Gly Leu Arg Leu Tyr
305                 310                 315                 320

Val Ala Ala Ile Ile Glu Ser Pro Gly Gly Glu Met Glu Glu Ala
                325                 330                 335

Glu Leu Thr Ser Trp Tyr Phe Val Ser Ser Pro Phe Ser Leu Asp Leu
            340                 345                 350

Ser Lys Thr Lys Arg His Leu Val Pro Gly Ala Pro Phe Leu Leu Gln
        355                 360                 365

Ala Leu Val Arg Glu Met Ser Gly Ser Pro Ala Ser Gly Ile Pro Val
370                 375                 380

Lys Val Ser Ala Thr Val Ser Ser Pro Gly Ser Val Pro Glu Val Gln
385                 390                 395                 400

Asp Ile Gln Gln Asn Thr Asp Gly Ser Gly Gln Val Ser Ile Pro Ile
                405                 410                 415

Ile Ile Pro Gln Thr Ile Ser Glu Leu Gln Leu Ser Val Ser Ala Gly
            420                 425                 430

Ser Pro His Pro Ala Ile Ala Arg Leu Thr Val Ala Ala Pro Pro Ser
        435                 440                 445

Gly Gly Pro Gly Phe Leu Ser Ile Glu Arg Pro Asp Ser Arg Pro Pro
450                 455                 460

Arg Val Gly Asp Thr Leu Asn Leu Asn Leu Arg Ala Val Gly Ser Gly
465                 470                 475                 480

Ala Thr Phe Ser His Tyr Tyr Tyr Met Ile Leu Ser Arg Gly Gln Ile
                485                 490                 495

Val Phe Met Asn Arg Glu Pro Lys Arg Thr Leu Thr Ser Val Ser Val
            500                 505                 510

Phe Val Asp His His Leu Ala Pro Ser Phe Tyr Phe Val Ala Phe Tyr
        515                 520                 525

Tyr His Gly Asp His Pro Val Ala Asn Ser Leu Arg Val Asp Val Gln
530                 535                 540

Ala Gly Ala Cys Glu Gly Lys Leu Glu Leu Ser Val Asp Gly Ala Lys

```
                545              550              555              560
        Gln Tyr Arg Asn Gly Glu Ser Val Lys Leu His Leu Glu Thr Asp Ser
                        565              570              575

Leu Ala Leu Val Ala Leu Gly Ala Leu Asp Thr Ala Leu Tyr Ala Ala
                        580              585              590

Gly Ser Lys Ser His Lys Pro Leu Asn Met Gly Lys Val Phe Glu Ala
                        595              600              605

Met Asn Ser Tyr Asp Leu Gly Cys Gly Pro Gly Gly Gly Asp Ser Ala
                        610              615              620

Leu Gln Val Phe Gln Ala Ala Gly Leu Ala Phe Ser Asp Gly Asp Gln
        625              630              635              640

Trp Thr Leu Ser Arg Lys Arg Leu Ser Cys Pro Lys Glu Lys Thr Thr
                        645              650              655

<210> SEQ ID NO 8
<211> LENGTH: 291
<212> TYPE: PRT
<213> ORGANISM: Homo sapiens

<400> SEQUENCE: 8

Glu Ala Pro Lys Val Val Glu Gln Glu Ser Arg Val His Tyr Thr
1               5                   10                  15

Val Cys Ile Trp Arg Asn Gly Lys Val Gly Leu Ser Gly Met Ala Ile
                20                  25                  30

Ala Asp Val Thr Leu Leu Ser Gly Phe His Ala Leu Arg Ala Asp Leu
            35                  40                  45

Glu Lys Leu Thr Ser Leu Ser Asp Arg Tyr Val Ser His Phe Glu Thr
50                  55                  60

Glu Gly Pro His Val Leu Leu Tyr Phe Asp Ser Val Pro Thr Ser Arg
65                  70                  75                  80

Glu Cys Val Gly Phe Glu Ala Val Gln Glu Val Pro Val Gly Leu Val
                85                  90                  95

Gln Pro Ala Ser Ala Thr Leu Tyr Asp Tyr Tyr Asn Pro Glu Arg Arg
            100                 105                 110

Cys Ser Val Phe Tyr Gly Ala Pro Ser Lys Ser Arg Leu Leu Ala Thr
            115                 120                 125

Leu Cys Ser Ala Glu Val Cys Gln Cys Ala Glu Gly Lys Cys Pro Arg
130                 135                 140

Gln Arg Arg Ala Leu Glu Arg Gly Leu Gln Asp Glu Asp Gly Tyr Arg
145                 150                 155                 160

Met Lys Phe Ala Cys Tyr Tyr Pro Arg Val Glu Tyr Gly Phe Gln Val
                165                 170                 175

Lys Val Leu Arg Glu Asp Ser Arg Ala Ala Phe Arg Leu Phe Glu Thr
            180                 185                 190

Lys Ile Thr Gln Val Leu His Phe Thr Lys Asp Val Lys Ala Ala Ala
            195                 200                 205

Asn Gln Met Arg Asn Phe Leu Val Arg Ala Ser Cys Arg Leu Arg Leu
210                 215                 220

Glu Pro Gly Lys Glu Tyr Leu Ile Met Gly Leu Asp Gly Ala Thr Tyr
225                 230                 235                 240

Asp Leu Glu Gly His Pro Gln Tyr Leu Leu Asp Ser Asn Ser Trp Ile
                245                 250                 255

Glu Glu Met Pro Ser Glu Arg Leu Cys Arg Ser Thr Arg Gln Arg Ala
            260                 265                 270
```

```
Ala Cys Ala Gln Leu Asn Asp Phe Leu Gln Glu Tyr Gly Thr Gln Gly
            275                 280                 285

Cys Gln Val
    290

<210> SEQ ID NO 9
<211> LENGTH: 129
<212> TYPE: PRT
<213> ORGANISM: Homo sapiens

<400> SEQUENCE: 9

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asn Gln Tyr
            20                  25                  30

Ala Ile Gly Trp Phe Arg Gln Ala Pro Gly Lys Glu Arg Glu Gly Val
            35                  40                  45

Ser Cys Ile Ser Asn Ser Asp Gly Gly Leu Tyr Tyr Ala Asp Ser Val
        50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Thr Asp Pro Gly Gly Pro Thr Met Tyr Gly Ser Arg Trp Cys Asp
            100                 105                 110

Ser Arg Leu Phe Tyr Ser Trp Gly Gln Gly Thr Gln Val Thr Val Ser
            115                 120                 125

Ser

<210> SEQ ID NO 10
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR1

<400> SEQUENCE: 10

Gly Phe Thr Leu Asn Gln Tyr Ala Ile Gly
1               5                   10

<210> SEQ ID NO 11
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR2

<400> SEQUENCE: 11

Cys Ile Ser Asn Ser Asp Gly Gly Leu Tyr
1               5                   10

<210> SEQ ID NO 12
<211> LENGTH: 20
<212> TYPE: PRT
<213> ORGANISM: Unknown
```

```
<220> FEATURE:
<223> OTHER INFORMATION: Artificial sequence/unknown
<220> FEATURE:
<221> NAME/KEY: MISC_FEATURE
<222> LOCATION: (1)..(20)
<223> OTHER INFORMATION: CDR3

<400> SEQUENCE: 12

Asp Pro Gly Gly Pro Thr Met Tyr Gly Ser Arg Trp Cys Asp Ser Arg
1               5                   10                  15

Leu Phe Tyr Ser
            20

<210> SEQ ID NO 13
<211> LENGTH: 125
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(125)
<223> OTHER INFORMATION: 1F75

<400> SEQUENCE: 13

Gln Val Gln Leu Val Glu Thr Gly Gly Gly Leu Val Gln Ala Gly Gly
1               5                   10                  15

Ser Leu Arg Leu Ser Cys Ala Ala Ser Gly Arg Thr Phe Asn Asn Asp
            20                  25                  30

Val Met Ala Trp Phe Arg Gln Ala Pro Gly Thr Glu Arg Glu Phe Val
        35                  40                  45

Ala Leu Ile Thr Ala Gly Gly Thr His Tyr Ala Asp Ser Val Lys
    50                  55                  60

Gly Arg Phe Val Ile Ser Arg Asp Asn Asp Lys Asn Met Ala Tyr Leu
65                  70                  75                  80

Gln Met Asn Ser Leu Lys Ser Glu Asp Thr Ala Ile Tyr Tyr Cys Gly
                85                  90                  95

Ala Asp Glu Asn Pro Pro Gly Trp Pro Ser Arg Trp Ser Ser Ala Tyr
            100                 105                 110

Asp Tyr Trp Gly Gln Gly Thr Gln Val Thr Val Ser Ser
        115                 120                 125

<210> SEQ ID NO 14
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR1

<400> SEQUENCE: 14

Gly Arg Thr Phe Asn Asn Asp Val Met Ala
1               5                   10

<210> SEQ ID NO 15
<211> LENGTH: 9
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
```

```
<222> LOCATION: (1)..(9)
<223> OTHER INFORMATION: CDR2

<400> SEQUENCE: 15

Leu Ile Thr Ala Gly Gly Gly Thr His
1               5

<210> SEQ ID NO 16
<211> LENGTH: 17
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(17)
<223> OTHER INFORMATION: CDR3

<400> SEQUENCE: 16

Asp Glu Asn Pro Pro Gly Trp Pro Ser Arg Trp Ser Ser Ala Tyr Asp
1               5                   10                  15
Tyr

<210> SEQ ID NO 17
<211> LENGTH: 128
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(128)
<223> OTHER INFORMATION: IF78

<400> SEQUENCE: 17

Gln Val Gln Leu Val Glu Ser Gly Gly Gly Leu Val Gln Asp Gly Asp
1               5                   10                  15

Ser Leu Arg Leu Ser Cys Ala Gly Ser Gly Trp Thr Phe Arg Asp Ser
            20                  25                  30

Met Tyr Asn Met Gly Trp Phe Arg Gln Ala Pro Gly Lys Glu Arg Glu
        35                  40                  45

Phe Val Ala Ala Ile Ser Trp Arg Gly Ser Thr Leu Tyr Ala Asp
    50                  55                  60

Ser Val Lys Gly Arg Phe Thr Ile Ser Arg Asp Asn Ala Lys Asn Thr
65                  70                  75                  80

Val Tyr Leu Gln Met Asn Ser Leu Lys Pro Glu Asp Thr Ala Val Tyr
                85                  90                  95

Gln Cys Ala Ala Asp Thr Ser Ala Arg Ala Ala Leu Tyr Ser Thr Gly
            100                 105                 110

Tyr Glu Tyr Asp His Trp Gly Gln Gly Thr Gln Val Thr Val Ser Ser
        115                 120                 125

<210> SEQ ID NO 18
<211> LENGTH: 12
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(12)
<223> OTHER INFORMATION: CDR1

<400> SEQUENCE: 18
```

```
Gly Trp Thr Phe Arg Asp Ser Met Tyr Asn Met Gly
1               5                   10
```

<210> SEQ ID NO 19
<211> LENGTH: 11
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(11)
<223> OTHER INFORMATION: CDR2

<400> SEQUENCE: 19

```
Ala Ile Ser Trp Arg Gly Gly Ser Thr Leu Tyr
1               5                   10
```

<210> SEQ ID NO 20
<211> LENGTH: 17
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(17)
<223> OTHER INFORMATION: CDR3

<400> SEQUENCE: 20

```
Asp Thr Ser Ala Arg Ala Ala Leu Tyr Ser Thr Gly Tyr Glu Tyr Asp
1               5                   10                  15

His
```

<210> SEQ ID NO 21
<211> LENGTH: 127
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(127)
<223> OTHER INFORMATION: IH31

<400> SEQUENCE: 21

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Ser Ser Asp His
            20                  25                  30

Ile Thr Ala Trp Phe Arg Gln Ala Pro Gly Lys Glu Arg Glu Phe Val
        35                  40                  45

Ala Ser Ile Asn Trp Ser Gly Ser Arg Ala Tyr Tyr Ala Asp Ser Asp
    50                  55                  60

Lys Arg Arg Phe Thr Ile Ser Arg Asp Asn Ala Lys Asn Thr Val Ser
65                  70                  75                  80

Leu Gln Thr Asn Ser Leu Lys Pro Glu Asp Thr Ala Val Tyr Tyr Cys
                85                  90                  95

Ala Val Lys Phe Ala Asp Ile Ser Asp Ala Tyr His His Gln Thr
            100                 105                 110

Asp Tyr Asp Tyr Trp Gly Gln Gly Thr Gln Val Thr Val Ser Ser
        115                 120                 125
```

<210> SEQ ID NO 22

```
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR1

<400> SEQUENCE: 22

Gly Arg Thr Ser Ser Asp His Ile Thr Ala
1               5                   10

<210> SEQ ID NO 23
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR2

<400> SEQUENCE: 23

Ser Ile Asn Trp Ser Gly Ser Arg Ala Tyr
1               5                   10

<210> SEQ ID NO 24
<211> LENGTH: 18
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(18)
<223> OTHER INFORMATION: CDR3

<400> SEQUENCE: 24

Lys Phe Ala Asp Ile Ser Asp Ala Tyr Tyr His His Gln Thr Asp Tyr
1               5                   10                  15

Asp Tyr

<210> SEQ ID NO 25
<211> LENGTH: 119
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(119)
<223> OTHER INFORMATION: IH33

<400> SEQUENCE: 25

Gln Val Gln Leu Val Glu Thr Gly Gly Gly Leu Val Gln Thr Gly Gly
1               5                   10                  15

Ser Leu Arg Leu Ser Cys Ala Ala Ser Gly Ser Thr Asp Ser Ile Ala
            20                  25                  30

Ala Ile Ile Trp Tyr Arg Gln Thr Pro Glu Asn Glu Arg Glu Phe Val
        35                  40                  45

Ala Gly Ile Thr Ser Gly Val Asn Thr Asn Tyr Ala Ala Pro Val Lys
    50                  55                  60

Gly Arg Phe Thr Ile Ser Arg Asp Asn Ala Lys Asn Thr Val Tyr Leu
65                  70                  75                  80
```

Gln Met Asn Ser Leu Lys Pro Glu Asp Thr Gly Val Tyr Tyr Cys Lys
                85                  90                  95

Ala Ala Val Val Met Gly Pro Ser Thr Thr Asp Tyr Trp Gly Gln Gly
            100                 105                 110

Thr Gln Val Thr Val Ser Ser
        115

<210> SEQ ID NO 26
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR1

<400> SEQUENCE: 26

Gly Ser Thr Asp Ser Ile Ala Ala Ile Ile
1               5                   10

<210> SEQ ID NO 27
<211> LENGTH: 7
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(7)
<223> OTHER INFORMATION: CDR2

<400> SEQUENCE: 27

Gly Ile Thr Ser Gly Val Asn
1               5

<210> SEQ ID NO 28
<211> LENGTH: 11
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(11)
<223> OTHER INFORMATION: CDR3

<400> SEQUENCE: 28

Ala Val Val Met Gly Pro Ser Thr Thr Asp Tyr
1               5                   10

<210> SEQ ID NO 29
<211> LENGTH: 124
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(124)
<223> OTHER INFORMATION: IH35

<400> SEQUENCE: 29

Gln Val Gln Leu Val Glu Thr Gly Gly Gly Val Ala Gln Ala Gly Gly
1               5                   10                  15

Ser Leu Arg Leu Ser Cys Ala Ala Ser Gly Phe Ser Phe Asp Asp Tyr

```
                    20                  25                  30
Ala Ile Gly Trp Leu Arg Gln Ala Pro Gly Lys Glu Arg Glu Gly Val
            35                  40                  45

Ser Cys Ile Ser Ala Gly Asp Gly Ser Pro Gln Tyr Ala Asp Ser Val
        50                  55                  60

Lys Gly Arg Phe Thr Ile Ser Ser Asp Asn Ala Lys Asn Thr Val Tyr
 65                  70                  75                  80

Leu Gln Met Asn Ser Leu Lys Pro Glu Asp Thr Ala Val Tyr Tyr Cys
                85                  90                  95

Ala Val Ser Arg Trp Ser Asn Cys Ala Trp Asp Tyr Tyr Gly Met Asp
            100                 105                 110

Pro Trp Gly Lys Gly Thr Leu Val Thr Val Ser Ser
        115                 120

<210> SEQ ID NO 30
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR1

<400> SEQUENCE: 30

Gly Phe Ser Phe Asp Asp Tyr Ala Ile Gly
1               5                   10

<210> SEQ ID NO 31
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR2

<400> SEQUENCE: 31

Cys Ile Ser Ala Gly Asp Gly Ser Pro Gln
1               5                   10

<210> SEQ ID NO 32
<211> LENGTH: 15
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(15)
<223> OTHER INFORMATION: CDR3

<400> SEQUENCE: 32

Ser Arg Trp Ser Asn Cys Ala Trp Asp Tyr Tyr Gly Met Asp Pro
1               5                   10                  15

<210> SEQ ID NO 33
<211> LENGTH: 125
<212> TYPE: PRT
<213> ORGANISM: Unknown
<220> FEATURE:
<223> OTHER INFORMATION: Artificial sequence/unknown
<220> FEATURE:
```

```
<221> NAME/KEY: MISC_FEATURE
<222> LOCATION: (1)..(125)
<223> OTHER INFORMATION: IH37

<400> SEQUENCE: 33
```

Gln Val Gln Leu Val Glu Ser Gly Gly Gly Leu Ala Gln Ala Gly Gly
1               5                   10                  15

Ser Leu Arg Leu Ser Cys Gln Gly Ser Gly Arg Thr Phe Asn Asn Asp
            20                  25                  30

Val Leu Ala Trp Phe Arg Gln Ala Pro Gly Lys Glu Arg Glu Tyr Val
        35                  40                  45

Ala Met Ile Thr Ser Gly Gly Asn Pro Phe Tyr Ala Asp Ser Val Lys
    50                  55                  60

Gly Arg Phe Val Ile Ser Arg Asp Asn Asp Lys Asn Thr Val Tyr Leu
65              70                  75                  80

Gln Met Asn Ser Leu Lys Ser Glu Asp Thr Ala Ile Tyr Tyr Cys Ala
                85                  90                  95

Ala Asp Glu Asn Pro Pro Gly Trp Pro Ser Arg Trp Ser Ser Ala Tyr
            100                 105                 110

Asp Tyr Trp Gly Gln Gly Thr Gln Val Thr Val Ser Ser
        115                 120                 125

```
<210> SEQ ID NO 34
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR1

<400> SEQUENCE: 34
```

Gly Arg Thr Phe Asn Asn Asp Val Leu Ala
1               5                   10

```
<210> SEQ ID NO 35
<211> LENGTH: 9
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(9)
<223> OTHER INFORMATION: CDR2

<400> SEQUENCE: 35
```

Met Ile Thr Ser Gly Gly Asn Pro Phe
1               5

```
<210> SEQ ID NO 36
<211> LENGTH: 17
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(17)
<223> OTHER INFORMATION: CDR3

<400> SEQUENCE: 36
```

Asp Glu Asn Pro Pro Gly Trp Pro Ser Arg Trp Ser Ser Ala Tyr Asp

Tyr

<210> SEQ ID NO 37
<211> LENGTH: 124
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(124)
<223> OTHER INFORMATION: IH39

<400> SEQUENCE: 37

Gln Val Gln Leu Val Glu Ser Gly Gly Gly Leu Val Gln Ala Gly Gly
1               5                   10                  15

Ser Leu Arg Leu Ser Cys Val Ala Tyr Gly Val Ala Ser Val Thr Thr
            20                  25                  30

Val Met Gly Trp Phe Arg Gln Ser Pro Gly Lys Glu Arg Glu Phe Val
        35                  40                  45

Ala Ala Ile Gly Pro Ser Gly Gly Thr His Tyr Gly Asp Ser Ala Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Asp Cys Ala
                85                  90                  95

Ala Asp Leu Arg Gly Gly Gly Met Trp Ala Ser Ser Gly Arg Tyr Glu
            100                 105                 110

Tyr Trp Gly Gln Gly Thr Gln Val Thr Val Ser Ser
        115                 120

<210> SEQ ID NO 38
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR1

<400> SEQUENCE: 38

Gly Val Ala Ser Val Thr Thr Val Met Gly
1               5                   10

<210> SEQ ID NO 39
<211> LENGTH: 9
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(9)
<223> OTHER INFORMATION: CDR2

<400> SEQUENCE: 39

Ala Ile Gly Pro Ser Gly Gly Thr His
1               5

<210> SEQ ID NO 40
<211> LENGTH: 16

```
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(16)
<223> OTHER INFORMATION: CDR3

<400> SEQUENCE: 40

Asp Leu Arg Gly Gly Gly Met Trp Ala Ser Ser Gly Arg Tyr Glu Tyr
1               5                   10                  15

<210> SEQ ID NO 41
<211> LENGTH: 124
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(124)
<223> OTHER INFORMATION: hC4bNb6

<400> SEQUENCE: 41

Gln Val Gln Leu Val Glu Thr Gly Gly Val Val Arg Ala Gly Gly
1               5                   10                  15

Ser Leu Arg Leu Ser Cys Ala Ala Ser Gly Arg Thr Leu Gly Arg Tyr
            20                  25                  30

Ser Met Ala Trp Phe Arg Gln Ala Pro Gly Lys Glu Arg Gln Phe Val
        35                  40                  45

Ala Ala Ile Asn Trp Ser Gly Ser Thr Tyr Tyr Pro Asp Phe Ala
    50                  55                  60

Lys Asp Arg Phe Thr Ile Ser Arg Asp Ser Ala Lys Asn Met Val Tyr
65                  70                  75                  80

Leu Gln Met Asn Ser Leu Lys Pro Glu Asp Thr Ala Val Tyr Tyr Cys
                85                  90                  95

Ala Ala Gly Gly Met Asp Ile Glu Ile Thr Arg Ala Asn Glu Tyr Asp
            100                 105                 110

Tyr Trp Gly Gln Gly Thr Gln Val Thr Val Ser Ser
        115                 120

<210> SEQ ID NO 42
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR1

<400> SEQUENCE: 42

Gly Arg Thr Leu Gly Arg Tyr Ser Met Ala
1               5                   10

<210> SEQ ID NO 43
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
```

```
<223> OTHER INFORMATION: CDR2

<400> SEQUENCE: 43

Ala Ile Asn Trp Ser Gly Gly Ser Thr Tyr
1               5                   10

<210> SEQ ID NO 44
<211> LENGTH: 15
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(15)
<223> OTHER INFORMATION: CDR3

<400> SEQUENCE: 44

Gly Gly Met Asp Ile Glu Ile Thr Arg Ala Asn Glu Tyr Asp Tyr
1               5                   10                  15

<210> SEQ ID NO 45
<211> LENGTH: 124
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(124)
<223> OTHER INFORMATION: hC4Nb8

<400> SEQUENCE: 45

Gln Val Gln Leu Val Glu Ser Gly Gly Gly Leu Val Gln Thr Gly Asp
1               5                   10                  15

Ser Leu Arg Leu Ser Cys Ala Ala Ser Gly Arg Thr Phe Ser Arg Tyr
            20                  25                  30

Ala Met Gly Trp Phe Arg Gln Ala Pro Gly Lys Glu Arg Glu Leu Val
        35                  40                  45

Ala Ala Ile Asn Trp Ser Gly Gly Ser Thr Tyr Tyr Ala Asp Phe Ala
    50                  55                  60

Lys Gly Arg Phe Thr Ile Ser Arg Asp Asn Ala Lys Asn Met Leu Tyr
65                  70                  75                  80

Leu Arg Met Ser Ser Leu Lys Pro Glu Asp Thr Ala Val Tyr Tyr Cys
                85                  90                  95

Ala Ala Gly Gly Pro Glu Val Glu Ile Thr Arg Ala Asn Glu Tyr Asp
            100                 105                 110

Tyr Trp Gly Gln Gly Thr Gln Val Thr Val Ser Ser
        115                 120

<210> SEQ ID NO 46
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR1

<400> SEQUENCE: 46

Gly Arg Thr Phe Ser Arg Tyr Ala Met Gly
1               5                   10
```

```
<210> SEQ ID NO 47
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR2

<400> SEQUENCE: 47

Ala Ile Asn Trp Ser Gly Gly Ser Thr Tyr
1               5                   10

<210> SEQ ID NO 48
<211> LENGTH: 15
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(15)
<223> OTHER INFORMATION: CDR3

<400> SEQUENCE: 48

Gly Gly Pro Glu Val Glu Ile Thr Arg Ala Asn Glu Tyr Asp Tyr
1               5                   10                  15

<210> SEQ ID NO 49
<211> LENGTH: 118
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(118)
<223> OTHER INFORMATION: D121

<400> SEQUENCE: 49

Gln Val Gln Leu Val Glu Ser Gly Gly Gly Leu Val Gln Ala Gly Gly
1               5                   10                  15

Ser Leu Arg Leu Ser Cys Val Val Ser Gly Ser Thr Phe Ser Asp Tyr
            20                  25                  30

Ala Met Gly Trp Tyr Arg Gln Ala Ala Gly Glu Gln Arg Glu Leu Val
        35                  40                  45

Ala Ala Ile Tyr Ser Thr Gly Arg Thr Asn Tyr Ile Asp Ser Val Lys
    50                  55                  60

Gly Arg Phe Thr Ile Ser Arg Asp Asn Ala Lys Thr Thr Val Tyr Leu
65                  70                  75                  80

Gln Met Asn Ser Leu Lys Pro Glu Asp Thr Ala Val Tyr Tyr Cys Asn
                85                  90                  95

Leu Leu Gly Ala Thr Thr Met Ile Asn Thr Lys Trp Gly Gln Gly Thr
            100                 105                 110

Gln Val Thr Val Ser Ser
        115

<210> SEQ ID NO 50
<211> LENGTH: 11
<212> TYPE: PRT
<213> ORGANISM: Unknown
<220> FEATURE:
<223> OTHER INFORMATION: Artificial sequence/unknown
```

```
<220> FEATURE:
<221> NAME/KEY: MISC_FEATURE
<222> LOCATION: (1)..(11)
<223> OTHER INFORMATION: CDR1

<400> SEQUENCE: 50

Ser Gly Ser Thr Phe Ser Asp Tyr Ala Met Gly
1               5                   10

<210> SEQ ID NO 51
<211> LENGTH: 9
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(9)
<223> OTHER INFORMATION: CDR2

<400> SEQUENCE: 51

Ala Ile Tyr Ser Thr Gly Arg Thr Asn
1               5

<210> SEQ ID NO 52
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR3

<400> SEQUENCE: 52

Leu Gly Ala Thr Thr Met Ile Asn Thr Lys
1               5                   10

<210> SEQ ID NO 53
<211> LENGTH: 128
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(128)
<223> OTHER INFORMATION: DI62

<400> SEQUENCE: 53

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asp Tyr
            20                  25                  30

Thr Met Gly Trp Phe Arg Gln Ala Pro Gly Lys Glu Arg Glu Phe Val
        35                  40                  45

Ala Gly Leu Ser Thr Gly Gly Ser Phe Thr Arg Tyr Ala Ala Ser Val
    50                  55                  60

Glu Gly Arg Phe Thr Ile Ser Arg Asp Asn Ala Lys Thr Thr Val Tyr
65                  70                  75                  80

Leu Gln Met Asn Asn Leu Gln Pro Glu Asp Thr Ala Val Tyr Tyr Cys
                85                  90                  95

Ala Ala Asp Phe Thr Pro Tyr Gly Thr Asn Trp Ser Arg Phe Arg Glu
            100                 105                 110
```

Ala Arg Asp His Tyr Trp Gly Gln Gly Thr Gln Val Thr Val Ser Ser
            115                 120                 125

<210> SEQ ID NO 54
<211> LENGTH: 11
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(11)
<223> OTHER INFORMATION: CDR1

<400> SEQUENCE: 54

Ser Gly Arg Thr Phe Ser Asp Tyr Thr Met Gly
1               5                   10

<210> SEQ ID NO 55
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR2

<400> SEQUENCE: 55

Gly Leu Ser Thr Gly Gly Ser Phe Thr Arg
1               5                   10

<210> SEQ ID NO 56
<211> LENGTH: 19
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(19)
<223> OTHER INFORMATION: CDR3

<400> SEQUENCE: 56

Asp Phe Thr Pro Tyr Gly Thr Asn Trp Ser Arg Phe Arg Glu Ala Arg
1               5                   10                  15

Asp His Tyr

<210> SEQ ID NO 57
<211> LENGTH: 127
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(127)
<223> OTHER INFORMATION: EWE-hC3Nb1

<400> SEQUENCE: 57

Met Glu Trp Glu Gln Val Gln Leu Val Glu Thr Gly Gly Leu Val
1               5                   10                  15

Gln Ala Gly Gly Ser Leu Arg Leu Ser Cys Ala Ala Ser Gly Ser Ile
                20                  25                  30

Phe Ser Ile Asn Ala Met Gly Trp Phe Arg Gln Ala Pro Gly Lys Glu
        35                  40                  45

Arg Glu Phe Val Ala Thr Ile Asn Arg Ser Gly Gly Arg Thr Tyr Tyr
50                  55                  60

Ala Asp Ser Val Lys Gly Arg Phe Thr Ile Ser Arg Asp Asn Gly Lys
65                  70                  75                  80

Asn Met Val Tyr Leu Gln Met His Ser Leu Lys Pro Glu Asp Thr Ala
                85                  90                  95

Ile Tyr Tyr Cys Ala Ala Gly Thr Gly Trp Ser Pro Gln Thr Asp Asn
                100                 105                 110

Glu Tyr Asn Tyr Trp Gly Gln Gly Thr Gln Val Thr Val Ser Ser
                115                 120                 125

<210> SEQ ID NO 58
<211> LENGTH: 11
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(11)
<223> OTHER INFORMATION: CDR1

<400> SEQUENCE: 58

Ser Gly Ser Ile Phe Ser Ile Asn Ala Met Gly
1               5                   10

<210> SEQ ID NO 59
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR2

<400> SEQUENCE: 59

Thr Ile Asn Arg Ser Gly Gly Arg Thr Tyr
1               5                   10

<210> SEQ ID NO 60
<211> LENGTH: 14
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(14)
<223> OTHER INFORMATION: CDR3

<400> SEQUENCE: 60

Gly Thr Gly Trp Ser Pro Gln Thr Asp Asn Glu Tyr Asn Tyr
1               5                   10

<210> SEQ ID NO 61
<211> LENGTH: 358
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(358)
<223> OTHER INFORMATION: IgG-Fc-hC3Nb1

<400> SEQUENCE: 61

```
Ala Pro Leu Glu Pro Lys Ser Ser Asp Lys Thr His Thr Cys Pro Pro
1               5                   10                  15

Cys Pro Ala Pro Glu Leu Leu Gly Gly Pro Ser Val Phe Leu Phe Pro
            20                  25                  30

Pro Lys Pro Lys Asp Thr Leu Met Ile Ser Arg Thr Pro Glu Val Thr
        35                  40                  45

Cys Val Val Val Asp Val Ser His Glu Asp Pro Glu Val Lys Phe Asn
50                  55                  60

Trp Tyr Val Asp Gly Val Glu Val His Asn Ala Lys Thr Lys Pro Arg
65                  70                  75                  80

Glu Glu Gln Tyr Asn Ser Thr Tyr Arg Val Val Ser Val Leu Thr Val
                85                  90                  95

Leu His Gln Asp Trp Leu Asn Gly Lys Glu Tyr Lys Cys Lys Val Ser
            100                 105                 110

Asn Lys Ala Leu Pro Ala Pro Ile Glu Lys Thr Ile Ser Lys Ala Lys
        115                 120                 125

Gly Gln Pro Arg Glu Pro Gln Val Tyr Thr Leu Pro Pro Ser Arg Glu
130                 135                 140

Glu Met Thr Lys Asn Gln Val Ser Leu Thr Cys Leu Val Lys Gly Phe
145                 150                 155                 160

Tyr Pro Ser Asp Ile Ala Val Glu Trp Glu Ser Asn Gly Gln Pro Glu
                165                 170                 175

Asn Asn Tyr Lys Thr Thr Pro Pro Val Leu Asp Ser Asp Gly Ser Phe
            180                 185                 190

Phe Leu Tyr Ser Lys Leu Thr Val Asp Lys Ser Arg Trp Gln Gln Gly
        195                 200                 205

Asn Val Phe Ser Cys Ser Val Met His Glu Ala Leu His Asn His Tyr
210                 215                 220

Thr Gln Lys Ser Leu Ser Leu Ser Pro Gly Ala Gln Val Gln Leu Val
225                 230                 235                 240

Glu Thr Gly Gly Gly Leu Val Gln Ala Gly Gly Ser Leu Arg Leu Ser
                245                 250                 255

Cys Ala Ala Ser Gly Ser Ile Phe Ser Ile Asn Ala Met Gly Trp Phe
            260                 265                 270

Arg Gln Ala Pro Gly Lys Glu Arg Glu Phe Val Ala Thr Ile Asn Arg
        275                 280                 285

Ser Gly Gly Arg Thr Tyr Tyr Ala Asp Ser Val Lys Gly Arg Phe Thr
290                 295                 300

Ile Ser Arg Asp Asn Gly Lys Asn Met Val Tyr Leu Gln Met His Ser
305                 310                 315                 320

Leu Lys Pro Glu Asp Thr Ala Ile Tyr Tyr Cys Ala Ala Gly Thr Gly
                325                 330                 335

Trp Ser Pro Gln Thr Asp Asn Glu Tyr Asn Tyr Trp Gly Gln Gly Thr
            340                 345                 350

Gln Val Thr Val Ser Ser
        355

<210> SEQ ID NO 62
<211> LENGTH: 11
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
```

```
<222> LOCATION: (1)..(11)
<223> OTHER INFORMATION: CDR1

<400> SEQUENCE: 62

Ser Gly Ser Ile Phe Ser Ile Asn Ala Met Gly
1               5                   10

<210> SEQ ID NO 63
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR2

<400> SEQUENCE: 63

Thr Ile Asn Arg Ser Gly Gly Arg Thr Tyr
1               5                   10

<210> SEQ ID NO 64
<211> LENGTH: 14
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(14)
<223> OTHER INFORMATION: CDR3

<400> SEQUENCE: 64

Gly Thr Gly Trp Ser Pro Gln Thr Asp Asn Glu Tyr Asn Tyr
1               5                   10

<210> SEQ ID NO 65
<211> LENGTH: 10
<212> TYPE: PRT
<213> ORGANISM: Artificial sequence
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: polypeptide linker

<400> SEQUENCE: 65

Gly Gly Gly Gly Ser Gly Gly Gly Gly Ser
1               5                   10

<210> SEQ ID NO 66
<211> LENGTH: 129
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(129)
<223> OTHER INFORMATION: hC4Nb5

<400> SEQUENCE: 66

Gln Val Gln Leu Val Glu Thr Gly Gly Gly Leu Val Gln Pro Gly Gly
1               5                   10                  15

Ser Leu Arg Leu Ser Cys Ala Ala Ser Gly Arg Thr Phe Asn Lys Asn
            20                  25                  30
```

```
Pro Met Ala Trp Phe Arg Gln Pro Gly Gln Glu Arg Asp Leu Val
         35                  40                  45

Ala Ala Ile Ser Trp Ser Gly Asp Ser Thr Asn Tyr Ala Asn Ser Val
 50                  55                  60

Gln Gly Arg Phe Thr Ile Ser Arg Asn Asn Ala Gln Arg Thr Val Ser
 65                  70                  75                  80

Leu Ser Met Asn Asn Leu Lys Pro Glu Asp Thr Ala Val Tyr Tyr Cys
             85                  90                  95

Ala Ala Val Gly Arg Thr Asp Tyr Ser Pro Asn Ser Leu Ala Leu Thr
            100                 105                 110

Ala Gln Asn Tyr Asp Tyr Trp Gly Gln Gly Thr Gln Val Thr Val Ser
            115                 120                 125

Ser

<210> SEQ ID NO 67
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR1

<400> SEQUENCE: 67

Gly Arg Thr Phe Asn Lys Asn Pro Met Ala
1               5                   10

<210> SEQ ID NO 68
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR2

<400> SEQUENCE: 68

Ala Ile Ser Trp Ser Gly Asp Ser Thr Asn
1               5                   10

<210> SEQ ID NO 69
<211> LENGTH: 19
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(19)
<223> OTHER INFORMATION: CDR3

<400> SEQUENCE: 69

Val Gly Arg Thr Asp Tyr Ser Pro Asn Ser Leu Ala Leu Thr Ala Gln
1               5                   10                  15

Asn Tyr Asp

<210> SEQ ID NO 70
<211> LENGTH: 124
<212> TYPE: PRT
<213> ORGANISM: Unknown
<220> FEATURE:
```

```
<223> OTHER INFORMATION: Artificial sequence/unknown
<220> FEATURE:
<221> NAME/KEY: MISC_FEATURE
<222> LOCATION: (1)..(124)
<223> OTHER INFORMATION: hC4Nb4

<400> SEQUENCE: 70

Gln Val Gln Leu Val Glu Thr Gly Gly Gly Leu Val Glu Ala Gly Gly
1               5                   10                  15

Ser Leu Arg Ile Ser Cys Ala Ala Ser Gly Arg Tyr Ala Met Gly Trp
            20                  25                  30

Phe Arg Gln Ala Pro Gly Asn Glu Arg Asp Phe Val Ala Ala Ile Ser
        35                  40                  45

Arg Ser Gly Asp Ser Ala Asn Tyr Ala Asp Thr Ala Trp Gly Arg Phe
    50                  55                  60

Thr Ile Ser Arg Asp Asn Ala Gln Asn Thr Met Thr Leu Gln Met Asn
65                  70                  75                  80

Ser Leu Lys Pro Glu Asp Thr Ala Val Tyr Tyr Cys Ala Ala Lys Ala
                85                  90                  95

Gly Leu Tyr Ser Leu Asn Ser Leu Phe Leu Arg Ser Gln Glu Tyr Thr
            100                 105                 110

Tyr Trp Gly Gln Gly Thr Gln Val Thr Val Ser Ser
        115                 120

<210> SEQ ID NO 71
<211> LENGTH: 6
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(6)
<223> OTHER INFORMATION: CDR1

<400> SEQUENCE: 71

Gly Arg Tyr Ala Met Gly
1               5

<210> SEQ ID NO 72
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR2

<400> SEQUENCE: 72

Ala Ile Ser Arg Ser Gly Asp Ser Ala Asn
1               5                   10

<210> SEQ ID NO 73
<211> LENGTH: 19
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(19)
<223> OTHER INFORMATION: CDR3

<400> SEQUENCE: 73
```

```
Lys Ala Gly Leu Tyr Ser Leu Asn Ser Leu Phe Leu Arg Ser Gln Glu
1               5                   10                  15

Tyr Thr Tyr

<210> SEQ ID NO 74
<211> LENGTH: 148
<212> TYPE: PRT
<213> ORGANISM: Mus musculus

<400> SEQUENCE: 74

Glu Asn Cys Phe Met Gln Gln Ser Gln Glu Lys Ile Asn Leu Asn Val
1               5                   10                  15

Arg Leu Asp Lys Ala Cys Glu Pro Gly Val Asp Tyr Val Tyr Lys Thr
                20                  25                  30

Glu Leu Thr Asn Ile Glu Leu Leu Asp Asp Phe Asp Glu Tyr Thr Met
            35                  40                  45

Thr Ile Gln Gln Val Ile Lys Ser Gly Ser Asp Glu Val Gln Ala Gly
        50                  55                  60

Gln Gln Arg Lys Phe Ile Ser His Ile Lys Cys Arg Asn Ala Leu Lys
65                  70                  75                  80

Leu Gln Lys Gly Lys Lys Tyr Leu Met Trp Gly Leu Ser Ser Asp Leu
                85                  90                  95

Trp Gly Glu Lys Pro Asn Thr Ser Tyr Ile Ile Gly Lys Asp Thr Trp
            100                 105                 110

Val Glu His Trp Pro Glu Ala Glu Cys Gln Asp Gln Lys Tyr Gln
        115                 120                 125

Lys Gln Cys Glu Glu Leu Gly Ala Phe Thr Glu Ser Met Val Val Tyr
130                 135                 140

Gly Cys Pro Asn
145

<210> SEQ ID NO 75
<211> LENGTH: 45
<212> TYPE: PRT
<213> ORGANISM: Mus musculus

<400> SEQUENCE: 75

Glu Lys Ile Asn Leu Asn Val Arg Leu Asp Lys Ala Cys Pro Glu Ala
1               5                   10                  15

Glu Glu Cys Gln Asp Gln Lys Tyr Gln Lys Gln Cys Glu Glu Leu Gly
                20                  25                  30

Ala Phe Thr Glu Ser Met Val Val Tyr Gly Cys Pro Asn
            35                  40                  45

<210> SEQ ID NO 76
<211> LENGTH: 126
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(126)
<223> OTHER INFORMATION: pNSL270

<400> SEQUENCE: 76

Gln Val Gln Leu Val Glu Ser Gly Gly Gly Leu Val Gln Ala Gly Gly
1               5                   10                  15

Ser Leu Arg Leu Ser Cys Val Ala Ser Ala Ser Thr Leu Asp Ile Tyr
```

```
                 20                  25                  30

Thr Tyr Ala Met Ala Trp Phe Arg Gln Ala Pro Gly Lys Arg Glu
             35                  40                  45

Phe Val Ala Ala Ile Ser Arg Asn Gly Tyr Ser Thr Tyr Tyr Ala Asp
         50                  55                  60

Ser Val Lys Gly Arg Phe Thr Ile Ser Lys Leu Asn Ala Lys Asn Thr
65                  70                  75                  80

Leu Tyr Leu Gln Met Asn Ser Leu Glu Pro Glu Asp Thr Ala Ala Tyr
                 85                  90                  95

Tyr Cys Ala Ala Asp Arg Thr Thr Glu Val Val Asp Arg Glu Asp Asp
             100                 105                 110

Tyr Gly Tyr Trp Gly Gln Gly Thr Gln Val Thr Val Ser Ser
         115                 120                 125

<210> SEQ ID NO 77
<211> LENGTH: 12
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(12)
<223> OTHER INFORMATION: CDR1

<400> SEQUENCE: 77

Ala Ser Thr Leu Asp Ile Tyr Thr Tyr Ala Met Ala
1               5                   10

<210> SEQ ID NO 78
<211> LENGTH: 10
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(10)
<223> OTHER INFORMATION: CDR2

<400> SEQUENCE: 78

Ala Ile Ser Arg Asn Gly Tyr Ser Thr Tyr
1               5                   10

<210> SEQ ID NO 79
<211> LENGTH: 15
<212> TYPE: PRT
<213> ORGANISM: Unknown
<220> FEATURE:
<223> OTHER INFORMATION: Artificial sequence/unknown
<220> FEATURE:
<221> NAME/KEY: MISC_FEATURE
<222> LOCATION: (1)..(15)
<223> OTHER INFORMATION: CDR3

<400> SEQUENCE: 79

Asp Arg Thr Thr Glu Val Val Asp Arg Glu Asp Asp Tyr Gly Tyr
1               5                   10                  15

<210> SEQ ID NO 80
<211> LENGTH: 767
<212> TYPE: PRT
<213> ORGANISM: Homo sapiens

<400> SEQUENCE: 80
```

-continued

```
Asn Val Asn Phe Gln Lys Ala Ile Asn Glu Lys Leu Gly Gln Tyr Ala
1               5                   10                  15

Ser Pro Thr Ala Lys Arg Cys Cys Gln Asp Gly Val Thr Arg Leu Pro
            20                  25                  30

Met Met Arg Ser Cys Glu Gln Arg Ala Ala Arg Val Gln Gln Pro Asp
            35                  40                  45

Cys Arg Glu Pro Phe Leu Ser Cys Cys Gln Phe Ala Glu Ser Leu Arg
50                      55                  60

Lys Lys Ser Arg Asp Lys Gly Gln Ala Gly Leu Gln Arg Ala Leu Glu
65                  70                  75                  80

Ile Leu Gln Glu Glu Asp Leu Ile Asp Glu Asp Ile Pro Val Arg
                85                  90                  95

Ser Phe Phe Pro Glu Asn Trp Leu Trp Arg Val Glu Thr Val Asp Arg
            100                 105                 110

Phe Gln Ile Leu Thr Leu Trp Leu Pro Asp Ser Leu Thr Thr Trp Glu
            115                 120                 125

Ile His Gly Leu Ser Leu Ser Lys Thr Lys Gly Leu Cys Val Ala Thr
            130                 135                 140

Pro Val Gln Leu Arg Val Phe Arg Glu Phe His Leu His Leu Arg Leu
145                 150                 155                 160

Pro Met Ser Val Arg Arg Phe Glu Gln Leu Glu Leu Arg Pro Val Leu
            165                 170                 175

Tyr Asn Tyr Leu Asp Lys Asn Leu Thr Val Ser Val His Val Ser Pro
            180                 185                 190

Val Glu Gly Leu Cys Leu Ala Gly Gly Gly Leu Ala Gln Gln Val
            195                 200                 205

Leu Val Pro Ala Gly Ser Ala Arg Pro Val Ala Phe Ser Val Val Pro
210                 215                 220

Thr Ala Ala Thr Ala Val Ser Leu Lys Val Val Ala Arg Gly Ser Phe
225                 230                 235                 240

Glu Phe Pro Val Gly Asp Ala Val Ser Lys Val Leu Gln Ile Glu Lys
            245                 250                 255

Glu Gly Ala Ile His Arg Glu Glu Leu Val Tyr Glu Leu Asn Pro Leu
            260                 265                 270

Asp His Arg Gly Arg Thr Leu Glu Ile Pro Gly Asn Ser Asp Pro Asn
            275                 280                 285

Met Ile Pro Asp Gly Asp Phe Asn Ser Tyr Val Arg Val Thr Ala Ser
            290                 295                 300

Asp Pro Leu Asp Thr Leu Gly Ser Glu Gly Ala Leu Ser Pro Gly Gly
305                 310                 315                 320

Val Ala Ser Leu Leu Arg Leu Pro Arg Gly Cys Gly Glu Gln Thr Met
            325                 330                 335

Ile Tyr Leu Ala Pro Thr Leu Ala Ala Ser Arg Tyr Leu Asp Lys Thr
            340                 345                 350

Glu Gln Trp Ser Thr Leu Pro Pro Glu Thr Lys Asp His Ala Val Asp
            355                 360                 365

Leu Ile Gln Lys Gly Tyr Met Arg Ile Gln Gln Phe Arg Lys Ala Asp
            370                 375                 380

Gly Ser Tyr Ala Ala Trp Leu Ser Arg Gly Ser Ser Thr Trp Leu Thr
385                 390                 395                 400

Ala Phe Val Leu Lys Val Leu Ser Leu Ala Gln Glu Gln Val Gly Gly
            405                 410                 415

Ser Pro Glu Lys Leu Gln Glu Thr Ser Asn Trp Leu Leu Ser Gln Gln
```

```
                420                 425                 430
Gln Ala Asp Gly Ser Phe Gln Asp Leu Ser Pro Val Ile His Arg Ser
            435                 440                 445

Met Gln Gly Gly Leu Val Gly Asn Asp Glu Thr Val Ala Leu Thr Ala
        450                 455                 460

Phe Val Thr Ile Ala Leu His His Gly Leu Ala Val Phe Gln Asp Glu
465                 470                 475                 480

Gly Ala Glu Pro Leu Lys Gln Arg Val Glu Ala Ser Ile Ser Lys Ala
                485                 490                 495

Ser Ser Phe Leu Gly Glu Lys Ala Ser Ala Gly Leu Leu Gly Ala His
            500                 505                 510

Ala Ala Ala Ile Thr Ala Tyr Ala Leu Thr Leu Thr Lys Ala Pro Ala
        515                 520                 525

Asp Leu Arg Gly Val Ala His Asn Asn Leu Met Ala Met Ala Gln Glu
    530                 535                 540

Thr Gly Asp Asn Leu Tyr Trp Gly Ser Val Thr Gly Ser Gln Ser Asn
545                 550                 555                 560

Ala Val Ser Pro Thr Pro Ala Pro Arg Asn Pro Ser Asp Pro Met Pro
                565                 570                 575

Gln Ala Pro Ala Leu Trp Ile Glu Thr Thr Ala Tyr Ala Leu Leu His
            580                 585                 590

Leu Leu Leu His Glu Gly Lys Ala Glu Met Ala Asp Gln Ala Ala Ala
        595                 600                 605

Trp Leu Thr Arg Gln Gly Ser Phe Gln Gly Gly Phe Arg Ser Thr Gln
    610                 615                 620

Asp Thr Val Ile Ala Leu Asp Ala Leu Ser Ala Tyr Trp Ile Ala Ser
625                 630                 635                 640

His Thr Thr Glu Glu Arg Gly Leu Asn Val Thr Leu Ser Ser Thr Gly
                645                 650                 655

Arg Asn Gly Phe Lys Ser His Ala Leu Gln Leu Asn Asn Arg Gln Ile
            660                 665                 670

Arg Gly Leu Glu Glu Glu Leu Gln Phe Ser Leu Gly Ser Lys Ile Asn
        675                 680                 685

Val Lys Val Gly Gly Asn Ser Lys Gly Thr Leu Lys Val Leu Arg Thr
    690                 695                 700

Tyr Asn Val Leu Asp Met Lys Asn Thr Thr Cys Gln Asp Leu Gln Ile
705                 710                 715                 720

Glu Val Thr Val Lys Gly His Val Glu Tyr Thr Met Glu Ala Asn Glu
                725                 730                 735

Asp Tyr Glu Asp Tyr Glu Tyr Asp Glu Leu Pro Ala Lys Asp Asp Pro
            740                 745                 750

Asp Ala Pro Leu Gln Pro Val Thr Pro Leu Gln Leu Phe Glu Gly
        755                 760                 765

<210> SEQ ID NO 81
<211> LENGTH: 690
<212> TYPE: PRT
<213> ORGANISM: Homo sapiens

<400> SEQUENCE: 81

Ala Leu Glu Ile Leu Gln Glu Glu Asp Leu Ile Asp Glu Asp Asp Ile
1               5                   10                  15

Pro Val Arg Ser Phe Phe Pro Glu Asn Trp Leu Trp Arg Val Glu Thr
            20                  25                  30
```

```
Val Asp Arg Phe Gln Ile Leu Thr Leu Trp Leu Pro Asp Ser Leu Thr
     35                  40                  45

Thr Trp Glu Ile His Gly Leu Ser Leu Ser Lys Thr Lys Gly Leu Cys
 50                  55                  60

Val Ala Thr Pro Val Gln Leu Arg Val Phe Arg Glu Phe His Leu His
 65                  70                  75                  80

Leu Arg Leu Pro Met Ser Val Arg Arg Phe Glu Gln Leu Glu Leu Arg
                 85                  90                  95

Pro Val Leu Tyr Asn Tyr Leu Asp Lys Asn Leu Thr Val Ser Val His
             100                 105                 110

Val Ser Pro Val Glu Gly Leu Cys Leu Ala Gly Gly Gly Leu Ala
             115                 120                 125

Gln Gln Val Leu Val Pro Ala Gly Ser Ala Arg Pro Val Ala Phe Ser
130                 135                 140

Val Val Pro Thr Ala Ala Ala Val Ser Leu Lys Val Val Ala Arg
145                 150                 155                 160

Gly Ser Phe Glu Phe Pro Val Gly Asp Ala Val Ser Lys Val Leu Gln
                 165                 170                 175

Ile Glu Lys Glu Gly Ala Ile His Arg Glu Glu Leu Val Tyr Glu Leu
             180                 185                 190

Asn Pro Leu Asp His Arg Gly Arg Thr Leu Glu Ile Pro Gly Asn Ser
             195                 200                 205

Asp Pro Asn Met Ile Pro Asp Gly Asp Phe Asn Ser Tyr Val Arg Val
             210                 215                 220

Thr Ala Ser Asp Pro Leu Asp Thr Leu Gly Ser Glu Gly Ala Leu Ser
225                 230                 235                 240

Pro Gly Gly Val Ala Ser Leu Leu Arg Leu Pro Arg Gly Cys Gly Glu
                 245                 250                 255

Gln Thr Met Ile Tyr Leu Ala Pro Thr Leu Ala Ala Ser Arg Tyr Leu
             260                 265                 270

Asp Lys Thr Glu Gln Trp Ser Thr Leu Pro Pro Glu Thr Lys Asp His
             275                 280                 285

Ala Val Asp Leu Ile Gln Lys Gly Tyr Met Arg Ile Gln Gln Phe Arg
             290                 295                 300

Lys Ala Asp Gly Ser Tyr Ala Ala Trp Leu Ser Arg Asp Ser Ser Thr
305                 310                 315                 320

Trp Leu Thr Ala Phe Val Leu Lys Val Leu Ser Leu Ala Gln Glu Gln
                 325                 330                 335

Val Gly Gly Ser Pro Glu Lys Leu Gln Glu Thr Ser Asn Trp Leu Leu
             340                 345                 350

Ser Gln Gln Gln Ala Asp Gly Ser Phe Gln Asp Pro Cys Pro Val Leu
             355                 360                 365

Asp Arg Ser Met Gln Gly Gly Leu Val Gly Asn Asp Glu Thr Val Ala
             370                 375                 380

Leu Thr Ala Phe Val Thr Ile Ala Leu His His Gly Leu Ala Val Phe
385                 390                 395                 400

Gln Asp Glu Gly Ala Glu Pro Leu Lys Gln Arg Val Glu Ala Ser Ile
                 405                 410                 415

Ser Lys Ala Asn Ser Phe Leu Gly Glu Lys Ala Ser Ala Gly Leu Leu
             420                 425                 430

Gly Ala His Ala Ala Ala Ile Thr Ala Tyr Ala Leu Thr Leu Thr Lys
             435                 440                 445

Ala Pro Val Asp Leu Leu Gly Val Ala His Asn Asn Leu Met Ala Met
```

```
                    450             455             460
Ala Gln Glu Thr Gly Asp Asn Leu Tyr Trp Gly Ser Val Thr Gly Ser
465                 470                 475                 480

Gln Ser Asn Ala Val Ser Pro Thr Pro Ala Pro Arg Asn Pro Ser Asp
                    485                 490                 495

Pro Met Pro Gln Ala Pro Ala Leu Trp Ile Glu Thr Thr Ala Tyr Ala
                500                 505                 510

Leu Leu His Leu Leu His Glu Gly Lys Ala Glu Met Ala Asp Gln
            515                 520                 525

Ala Ser Ala Trp Leu Thr Arg Gln Gly Ser Phe Gln Gly Gly Phe Arg
530                 535                 540

Ser Thr Gln Asp Thr Val Ile Ala Leu Asp Ala Leu Ser Ala Tyr Trp
545                 550                 555                 560

Ile Ala Ser His Thr Thr Glu Glu Arg Gly Leu Asn Val Thr Leu Ser
                565                 570                 575

Ser Thr Gly Arg Asn Gly Phe Lys Ser His Ala Leu Gln Leu Asn Asn
                580                 585                 590

Arg Gln Ile Arg Gly Leu Glu Glu Leu Gln Phe Ser Leu Gly Ser
            595                 600                 605

Lys Ile Asn Val Lys Val Gly Gly Asn Ser Lys Gly Thr Leu Lys Val
            610                 615                 620

Leu Arg Thr Tyr Asn Val Leu Asp Met Lys Asn Thr Thr Cys Gln Asp
625                 630                 635                 640

Leu Gln Ile Glu Val Thr Val Lys Gly His Val Glu Tyr Thr Met Glu
                645                 650                 655

Ala Asn Glu Asp Tyr Glu Asp Tyr Glu Tyr Asp Glu Leu Pro Ala Lys
                660                 665                 670

Asp Asp Pro Asp Ala Pro Leu Gln Pro Val Thr Pro Leu Gln Leu Phe
            675                 680                 685

Glu Gly
    690

<210> SEQ ID NO 82
<211> LENGTH: 690
<212> TYPE: PRT
<213> ORGANISM: Homo sapiens

<400> SEQUENCE: 82

Ala Leu Glu Ile Leu Gln Glu Asp Leu Ile Asp Glu Asp Ile
1               5                   10                  15

Pro Val Arg Ser Phe Phe Pro Glu Asn Trp Leu Trp Arg Val Glu Thr
                20                  25                  30

Val Asp Arg Phe Gln Ile Leu Thr Leu Trp Leu Pro Asp Ser Leu Thr
            35                  40                  45

Thr Trp Glu Ile His Gly Leu Ser Leu Ser Lys Thr Lys Gly Leu Cys
50                  55                  60

Val Ala Thr Pro Val Gln Leu Arg Val Phe Arg Glu Phe His Leu His
65                  70                  75                  80

Leu Arg Leu Pro Met Ser Val Arg Arg Phe Glu Gln Leu Glu Leu Arg
                85                  90                  95

Pro Val Leu Tyr Asn Tyr Leu Asp Lys Asn Leu Thr Val Ser Val His
            100                 105                 110

Val Ser Pro Val Glu Gly Leu Cys Leu Ala Gly Gly Gly Leu Ala
            115                 120                 125
```

-continued

Gln Gln Val Leu Val Pro Ala Gly Ser Ala Arg Pro Val Ala Phe Ser
    130                 135                 140

Val Val Pro Thr Ala Ala Thr Ala Val Ser Leu Lys Val Ala Arg
145                 150                 155                 160

Gly Ser Phe Glu Phe Pro Val Gly Asp Ala Val Ser Lys Val Leu Gln
                165                 170                 175

Ile Glu Lys Glu Gly Ala Ile His Arg Glu Leu Val Tyr Glu Leu
            180                 185                 190

Asn Pro Leu Asp His Arg Gly Arg Thr Leu Glu Ile Pro Gly Asn Ser
        195                 200                 205

Asp Pro Asn Met Ile Pro Asp Gly Asp Phe Asn Ser Tyr Val Arg Val
    210                 215                 220

Thr Ala Ser Asp Pro Leu Asp Thr Leu Gly Ser Glu Gly Ala Leu Ser
225                 230                 235                 240

Pro Gly Gly Val Ala Ser Leu Leu Arg Leu Pro Arg Gly Cys Gly Glu
                245                 250                 255

Gln Thr Met Ile Tyr Leu Ala Pro Thr Leu Ala Ala Ser Arg Tyr Leu
            260                 265                 270

Asp Lys Thr Glu Gln Trp Ser Thr Leu Pro Pro Glu Thr Lys Asp His
        275                 280                 285

Ala Val Asp Leu Ile Gln Lys Gly Tyr Met Arg Ile Gln Gln Phe Arg
    290                 295                 300

Lys Ala Asp Gly Ser Tyr Ala Ala Trp Leu Ser Arg Gly Ser Ser Thr
305                 310                 315                 320

Trp Leu Thr Ala Phe Val Leu Lys Val Leu Ser Leu Ala Gln Glu Gln
                325                 330                 335

Val Gly Gly Ser Pro Glu Lys Leu Gln Glu Thr Ser Asn Trp Leu Leu
            340                 345                 350

Ser Gln Gln Gln Ala Asp Gly Ser Phe Gln Asp Leu Ser Pro Val Ile
        355                 360                 365

His Arg Ser Met Gln Gly Gly Leu Val Gly Asn Asp Glu Thr Val Ala
    370                 375                 380

Leu Thr Ala Phe Val Thr Ile Ala Leu His His Gly Leu Ala Val Phe
385                 390                 395                 400

Gln Asp Glu Gly Ala Glu Pro Leu Lys Gln Arg Val Glu Ala Ser Ile
                405                 410                 415

Ser Lys Ala Ser Ser Phe Leu Gly Glu Lys Ala Ser Ala Gly Leu Leu
            420                 425                 430

Gly Ala His Ala Ala Ile Thr Ala Tyr Ala Leu Thr Leu Thr Lys
        435                 440                 445

Ala Pro Ala Asp Leu Arg Gly Val Ala His Asn Asn Leu Met Ala Met
450                 455                 460

Ala Gln Glu Thr Gly Asp Asn Leu Tyr Trp Gly Ser Val Thr Gly Ser
465                 470                 475                 480

Gln Ser Asn Ala Val Ser Pro Thr Pro Ala Pro Arg Asn Pro Ser Asp
                485                 490                 495

Pro Met Pro Gln Ala Pro Ala Leu Trp Ile Glu Thr Thr Ala Tyr Ala
            500                 505                 510

Leu Leu His Leu Leu Leu His Glu Gly Lys Ala Glu Met Ala Asp Gln
        515                 520                 525

Ala Ala Ala Trp Leu Thr Arg Gln Gly Ser Phe Gln Gly Gly Phe Arg
    530                 535                 540

Ser Thr Gln Asp Thr Val Ile Ala Leu Asp Ala Leu Ser Ala Tyr Trp

```
                545                 550                 555                 560
        Ile Ala Ser His Thr Thr Glu Glu Arg Gly Leu Asn Val Thr Leu Ser
                        565                 570                 575

Ser Thr Gly Arg Asn Gly Phe Lys Ser His Ala Leu Gln Leu Asn Asn
                        580                 585                 590

Arg Gln Ile Arg Gly Leu Glu Glu Leu Gln Phe Ser Leu Gly Ser
                        595                 600                 605

Lys Ile Asn Val Lys Val Gly Gly Asn Ser Lys Gly Thr Leu Lys Val
                        610                 615                 620

Leu Arg Thr Tyr Asn Val Leu Asp Met Lys Asn Thr Thr Cys Gln Asp
        625                 630                 635                 640

Leu Gln Ile Glu Val Thr Val Lys Gly His Val Glu Tyr Thr Met Glu
                        645                 650                 655

Ala Asn Glu Asp Tyr Glu Asp Tyr Glu Tyr Asp Glu Leu Pro Ala Lys
                        660                 665                 670

Asp Asp Pro Asp Ala Pro Leu Gln Pro Val Thr Pro Leu Gln Leu Phe
                        675                 680                 685

Glu Gly
                690

<210> SEQ ID NO 83
<211> LENGTH: 654
<212> TYPE: PRT
<213> ORGANISM: Mus musculus

<400> SEQUENCE: 83

Lys Pro Arg Leu Leu Phe Ser Pro Ser Val Val Asn Leu Gly Thr
        1               5                   10                  15

Pro Leu Ser Val Gly Val Gln Leu Leu Asp Ala Pro Gly Gln Glu
                        20                  25                  30

Val Lys Gly Ser Val Phe Leu Arg Asn Pro Lys Gly Gly Ser Cys Ser
                        35                  40                  45

Pro Lys Lys Asp Phe Lys Leu Ser Ser Gly Asp Asp Phe Val Leu Leu
        50                  55                  60

Ser Leu Glu Val Pro Leu Glu Asp Val Arg Ser Cys Gly Leu Phe Asp
        65                  70                  75                  80

Leu Arg Arg Ala Pro His Ile Gln Leu Val Ala Gln Ser Pro Trp Leu
                        85                  90                  95

Arg Asn Thr Ala Phe Lys Ala Thr Glu Thr Gln Gly Val Asn Leu Leu
                        100                 105                 110

Phe Ser Ser Arg Arg Gly His Ile Phe Val Gln Thr Asp Gln Pro Ile
                        115                 120                 125

Tyr Asn Pro Gly Gln Arg Val Arg Tyr Arg Val Phe Ala Leu Asp Gln
                        130                 135                 140

Lys Met Arg Pro Ser Thr Asp Phe Leu Thr Ile Thr Val Glu Asn Ser
        145                 150                 155                 160

His Gly Leu Arg Val Leu Lys Lys Glu Ile Phe Thr Ser Thr Ser Ile
                        165                 170                 175

Phe Gln Asp Ala Phe Thr Ile Pro Asp Ile Ser Glu Pro Gly Thr Trp
                        180                 185                 190

Lys Ile Ser Ala Arg Phe Ser Asp Gly Leu Glu Ser Asn Arg Ser Thr
                        195                 200                 205

His Phe Glu Val Lys Lys Tyr Val Leu Pro Asn Phe Glu Val Lys Ile
                        210                 215                 220
```

```
Thr Pro Trp Lys Pro Tyr Ile Leu Met Val Pro Ser Asn Ser Asp Glu
225                 230                 235                 240

Ile Gln Leu Asp Ile Gln Ala Arg Tyr Ile Tyr Gly Lys Pro Val Gln
                245                 250                 255

Gly Val Ala Tyr Thr Arg Phe Ala Leu Met Asp Glu Gln Gly Lys Arg
            260                 265                 270

Thr Phe Leu Arg Gly Leu Glu Thr Gln Ala Lys Leu Val Glu Gly Arg
        275                 280                 285

Thr His Ile Ser Ile Ser Lys Asp Gln Phe Gln Ala Ala Leu Asp Lys
    290                 295                 300

Ile Asn Ile Gly Val Arg Asp Leu Glu Gly Leu Arg Leu Tyr Ala Ala
305                 310                 315                 320

Thr Ala Val Ile Glu Ser Pro Gly Gly Glu Met Glu Glu Ala Glu Leu
                325                 330                 335

Thr Ser Trp Arg Phe Val Ser Ser Ala Phe Ser Leu Asp Leu Ser Arg
            340                 345                 350

Thr Lys Arg His Leu Val Pro Gly Ala His Phe Leu Leu Gln Ala Leu
        355                 360                 365

Val Gln Glu Met Ser Gly Ser Glu Ala Ser Asn Val Pro Val Lys Val
    370                 375                 380

Ser Ala Thr Leu Val Ser Gly Ser Asp Ser Gln Val Leu Asp Ile Gln
385                 390                 395                 400

Gln Ser Thr Asn Gly Ile Gly Gln Val Ser Ile Ser Phe Pro Ile Pro
                405                 410                 415

Pro Thr Val Thr Glu Leu Arg Leu Leu Val Ser Ala Gly Ser Leu Tyr
            420                 425                 430

Pro Ala Ile Ala Arg Leu Thr Val Gln Ala Pro Pro Ser Arg Gly Thr
        435                 440                 445

Gly Phe Leu Ser Ile Glu Pro Leu Asp Pro Arg Ser Pro Ser Val Gly
    450                 455                 460

Asp Thr Phe Ile Leu Asn Leu Gln Pro Val Gly Ile Pro Ala Pro Thr
465                 470                 475                 480

Phe Ser His Tyr Tyr Tyr Met Ile Ile Ser Arg Gly Gln Ile Met Ala
                485                 490                 495

Met Gly Arg Glu Pro Arg Lys Thr Val Thr Ser Val Ser Val Leu Val
            500                 505                 510

Asp His Gln Leu Ala Pro Ser Phe Tyr Phe Val Ala Tyr Phe Tyr His
        515                 520                 525

Gln Gly His Pro Val Ala Asn Ser Leu Leu Ile Asn Ile Gln Ser Arg
    530                 535                 540

Asp Cys Glu Gly Lys Leu Gln Leu Lys Val Asp Gly Ala Lys Glu Tyr
545                 550                 555                 560

Arg Asn Ala Asp Met Met Lys Leu Arg Ile Gln Thr Asp Ser Lys Ala
                565                 570                 575

Leu Val Ala Leu Gly Ala Val Asp Met Ala Leu Tyr Ala Val Gly Gly
            580                 585                 590

Arg Ser His Lys Pro Leu Asp Met Ser Lys Val Phe Glu Val Ile Asn
        595                 600                 605

Ser Tyr Asn Val Gly Cys Gly Pro Gly Gly Gly Asp Asp Ala Leu Gln
    610                 615                 620

Val Phe Gln Asp Ala Gly Leu Ala Phe Ser Asp Gly Asp Arg Leu Thr
625                 630                 635                 640

Gln Thr Arg Glu Asp Leu Ser Cys Pro Lys Glu Lys Lys Ser
```

-continued

```
                645                 650

<210> SEQ ID NO 84
<211> LENGTH: 766
<212> TYPE: PRT
<213> ORGANISM: Mus musculus

<400> SEQUENCE: 84

Asn Val Asn Phe Gln Lys Ala Val Ser Glu Lys Leu Gly Gln Tyr Ser
 1               5                  10                  15

Ser Pro Asp Ala Lys Arg Cys Cys Gln Asp Gly Met Thr Lys Leu Pro
                20                  25                  30

Met Lys Arg Thr Cys Glu Gln Arg Ala Ala Arg Val Pro Gln Gln Ala
            35                  40                  45

Cys Arg Glu Pro Phe Leu Ser Cys Cys Lys Phe Ala Glu Asp Leu Arg
        50                  55                  60

Arg Asn Gln Thr Arg Ser Gln Ala His Leu Ala Arg Asn Asn His Asn
 65                  70                  75                  80

Met Leu Gln Glu Glu Asp Leu Ile Asp Glu Asp Ile Leu Val Arg
                85                  90                  95

Thr Ser Phe Pro Glu Asn Trp Leu Trp Arg Val Glu Pro Val Asp Ser
                100                 105                 110

Ser Lys Leu Leu Thr Val Trp Leu Pro Asp Ser Met Thr Thr Trp Glu
            115                 120                 125

Ile His Gly Val Ser Leu Ser Lys Ser Lys Gly Leu Cys Val Ala Lys
        130                 135                 140

Pro Thr Arg Val Arg Val Phe Arg Lys Phe His Leu His Leu Arg Leu
145                 150                 155                 160

Pro Ile Ser Ile Arg Arg Phe Glu Gln Phe Glu Leu Arg Pro Val Leu
                165                 170                 175

Tyr Asn Tyr Leu Asn Asp Asp Val Ala Val Ser Val His Val Thr Pro
                180                 185                 190

Val Glu Gly Leu Cys Leu Ala Gly Gly Met Met Ala Gln Gln Val
            195                 200                 205

Thr Val Pro Ala Gly Ser Ala Arg Pro Val Ala Phe Ser Val Val Pro
        210                 215                 220

Thr Ala Ala Ala Asn Val Pro Leu Lys Val Val Ala Arg Gly Val Phe
225                 230                 235                 240

Asp Leu Gly Asp Ala Val Ser Lys Ile Leu Gln Ile Glu Lys Glu Gly
                245                 250                 255

Ala Ile His Arg Glu Glu Leu Val Tyr Asn Leu Asp Pro Leu Asn Asn
                260                 265                 270

Leu Gly Arg Thr Leu Glu Ile Pro Gly Ser Ser Asp Pro Asn Ile Val
            275                 280                 285

Pro Asp Gly Asp Phe Ser Ser Leu Val Arg Val Thr Ala Ser Glu Pro
        290                 295                 300

Leu Glu Thr Met Gly Ser Glu Gly Ala Leu Ser Pro Gly Gly Val Ala
305                 310                 315                 320

Ser Leu Leu Arg Leu Pro Gln Gly Cys Ala Glu Gln Thr Met Ile Tyr
                325                 330                 335

Leu Ala Pro Thr Leu Thr Ala Ser Asn Tyr Leu Asp Arg Thr Glu Gln
                340                 345                 350

Trp Ser Lys Leu Ser Pro Glu Thr Lys Asp His Ala Val Asp Leu Ile
            355                 360                 365
```

```
Gln Lys Gly Tyr Met Arg Ile Gln Gln Phe Arg Lys Asn Asp Gly Ser
    370                 375                 380

Phe Gly Ala Trp Leu His Arg Asp Ser Ser Thr Trp Leu Thr Ala Phe
385                 390                 395                 400

Val Leu Lys Ile Leu Ser Leu Ala Gln Glu Gln Val Gly Asn Ser Pro
                405                 410                 415

Glu Lys Leu Gln Glu Thr Ala Ser Trp Leu Leu Ala Gln Gln Leu Gly
                420                 425                 430

Asp Gly Ser Phe His Asp Pro Cys Pro Val Ile His Arg Ala Met Gln
            435                 440                 445

Gly Gly Leu Val Gly Ser Asp Glu Thr Val Ala Leu Thr Ala Phe Val
    450                 455                 460

Val Ile Ala Leu His His Gly Leu Asp Val Phe Gln Asp Asp Asp Ala
465                 470                 475                 480

Lys Gln Leu Lys Asn Arg Val Glu Ala Ser Ile Thr Lys Ala Asn Ser
                485                 490                 495

Phe Leu Gly Gln Lys Ala Ser Ala Gly Leu Leu Gly Ala His Ala Ala
                500                 505                 510

Ala Ile Thr Ala Tyr Ala Leu Thr Leu Thr Lys Ala Ser Glu Asp Leu
        515                 520                 525

Arg Asn Val Ala His Asn Ser Leu Met Ala Met Ala Glu Thr Gly
    530                 535                 540

Glu His Leu Tyr Trp Gly Leu Val Leu Gly Ser Gln Asp Lys Val Val
545                 550                 555                 560

Leu Arg Pro Thr Ala Pro Arg Ser Pro Thr Glu Pro Val Pro Gln Ala
                565                 570                 575

Pro Ala Leu Trp Ile Glu Thr Thr Ala Tyr Ala Leu Leu His Leu Leu
            580                 585                 590

Leu Arg Glu Gly Lys Gly Lys Met Ala Asp Lys Ala Ala Ser Trp Leu
    595                 600                 605

Thr His Gln Gly Ser Phe His Gly Ala Phe Arg Ser Thr Gln Asp Thr
    610                 615                 620

Val Val Thr Leu Asp Ala Leu Ser Ala Tyr Trp Ile Ala Ser His Thr
625                 630                 635                 640

Thr Glu Glu Lys Ala Leu Asn Val Thr Leu Ser Ser Met Gly Arg Asn
                645                 650                 655

Gly Leu Lys Thr His Gly Leu His Leu Asn Asn His Gln Val Lys Gly
                660                 665                 670

Leu Glu Glu Glu Leu Lys Phe Ser Leu Gly Ser Thr Ile Ser Val Lys
                675                 680                 685

Val Glu Gly Asn Ser Lys Gly Thr Leu Lys Ile Leu Arg Thr Tyr Asn
            690                 695                 700

Val Leu Asp Met Lys Asn Thr Thr Cys Gln Asp Leu Gln Ile Glu Val
705                 710                 715                 720

Lys Val Thr Gly Ala Val Glu Tyr Ala Trp Asp Ala Asn Glu Asp Tyr
                725                 730                 735

Glu Asp Tyr Tyr Asp Met Pro Ala Ala Asp Asp Pro Ser Val Pro Leu
            740                 745                 750

Gln Pro Val Thr Pro Leu Gln Leu Phe Glu Gly Arg Arg Ser
        755                 760                 765

<210> SEQ ID NO 85
<211> LENGTH: 291
<212> TYPE: PRT
```

```
<213> ORGANISM: Mus musculus

<400> SEQUENCE: 85

Glu Ala Pro Lys Val Glu Glu Gln Glu Ser Arg Val Gln Tyr Thr
1               5                   10                  15

Val Cys Ile Trp Arg Asn Gly Lys Leu Gly Leu Ser Gly Met Ala Ile
            20                  25                  30

Ala Asp Ile Thr Leu Leu Ser Gly Phe His Ala Leu Arg Ala Asp Leu
            35                  40                  45

Glu Lys Leu Thr Ser Leu Ser Asp Arg Tyr Val Ser His Phe Glu Thr
            50                  55                  60

Asp Gly Pro His Val Leu Leu Tyr Phe Asp Ser Val Pro Thr Thr Arg
65                      70                  75                  80

Glu Cys Val Gly Phe Gly Ala Ser Gln Glu Val Val Val Gly Leu Val
                    85                  90                  95

Gln Pro Ser Ser Ala Val Leu Tyr Asp Tyr Tyr Ser Pro Asp His Lys
                100                 105                 110

Cys Ser Val Phe Tyr Ala Ala Pro Thr Lys Ser Gln Leu Leu Ala Thr
            115                 120                 125

Leu Cys Ser Gly Asp Val Cys Gln Cys Ala Glu Gly Lys Cys Pro Arg
130                 135                 140

Leu Leu Arg Ser Leu Glu Arg Val Glu Asp Lys Asp Gly Tyr Arg
145                 150                 155                 160

Met Arg Phe Ala Cys Tyr Tyr Pro Arg Val Glu Tyr Gly Phe Thr Val
                165                 170                 175

Lys Val Leu Arg Glu Asp Gly Arg Ala Ala Phe Arg Leu Phe Glu Ser
            180                 185                 190

Lys Ile Thr Gln Val Leu His Phe Arg Lys Asp Thr Met Ala Ser Ile
            195                 200                 205

Gly Gln Thr Arg Asn Phe Leu Ser Arg Ala Ser Cys Arg Leu Arg Leu
            210                 215                 220

Glu Pro Asn Lys Glu Tyr Leu Ile Met Gly Met Asp Gly Glu Thr Ser
225                 230                 235                 240

Asp Asn Lys Gly Asp Pro Gln Tyr Leu Leu Asp Ser Asn Thr Trp Ile
                245                 250                 255

Glu Glu Met Pro Ser Glu Gln Met Cys Lys Ser Thr Arg His Arg Ala
                260                 265                 270

Ala Cys Phe Gln Leu Lys Asp Phe Leu Met Glu Phe Ser Ser Arg Gly
            275                 280                 285

Cys Gln Val
            290
```

SINGLE DOMAIN ANTIBODIES FOR COMPLEMENT REGULATION

TECHNICAL FIELD

The present invention relates to macromolecules containing single domain antibodies capable of regulating one or more complement pathways by specific binding to human complement factors.

BACKGROUND

The complement system is part of the innate immune system and plays an important role in protection against invading microorganisms and in maintenance of homoeostasis. Uncontrolled activation or lack of proper regulation of complement is involved in a range of diseases and pharmacological inhibition of complement is believed to represent an attractive strategy to ameliorate disease outcome. This is exemplified by the clinical use of the monoclonal antibody eculizumab which reacts with complement factor C5.

The complement system is activated by three different proteolytic pathways: The classical pathway (CP), the lectin pathway (LP) and the alternative pathway (AP) (FIG. 1).

Therapeutic antibodies used in cancer treatment often rely on activating different parts of the immune system for optimal efficiency. However, only a subset of currently licensed antibodies activates the complement system and complement thus represents a severely underexploited mechanism for clearance of cancer cells but also pathogenic microorganisms.

A new single domain antibody based technology is therefore provided herein below, which potently and specifically modulate the complement system on target cells.

SUMMARY

The main object of the present disclosure is to describe single domain antibodies, also termed nanobodies, which are capable of modulating complement activity by specifically targeting epitopes of human complement factors.

In one aspect, single domain antibodies are provided, which are capable of specifically binding to an epitope of a human complement factor selected from the group consisting of C1q, C3, C4 and/or the proteolytic derivatives C3b and C4b.

In another aspect, a composition is provided, in particular a pharmaceutical composition, comprising a single domain antibody as defined above.

In a third aspect, a single domain antibody or a composition as defined above is provided for use as a medicament.

Another aspect provides a method of modulating the activity of the complement system, said method comprising
a) providing a composition comprising a human complement factor selected from the group consisting of C1q, C3, C4 and/or the proteolytic derivatives C3b and C4b,
b) contacting said composition with a single domain antibody as defined above.

In yet another aspect, a method is provided of treating a disorder associated with complement activation, said method comprising administering a therapeutically effective amount of a single domain antibody or composition as defined above.

In a further aspect, a method is provided of producing a single domain antibody, said method comprising immunizing a camelid with polypeptide comprising an epitope of a human complement factor selected from the group consisting of the human C1q, C3, C4 and/or the proteolytic derivatives C3b and C4b.

In a final aspect, a method is provided of detecting the presence of a complement factor selected from the group consisting of the human C1q, C3, C4 and/or the proteolytic derivatives C3b and C4b, wherein a single domain antibody as defined in any of the preceding claims is used as a detection agent.

DESCRIPTION OF DRAWINGS

FIGS. 2A-2D. (FIG. 2A) Binding of C1q to IgG immune complexes in the presence of different Nbs. (FIG. 2B) A subset of these Nbs prevent C4b deposition, and thus CP activation, in a concentration dependent manner. The assay measures C4b deposition in serial dilutions of normal human serum (NHS). (FIG. 2C) Updated comprehensive version of FIG. 2A. (FIG. 2D) Updated comprehensive version of FIG. 2B.

(FIG. 3A) Reconstruction based on electron microscopy, of the complex formed between C3b and the Nb D121, asterix marks the position of D121, and the epitope is the C3b C345c domain. (FIG. 3B) The crystal structure of the C-terminal domain of C3b in complex with D121 confirms this epitope mapping. (FIG. 3C) Size exclusion chromatography (SEC) analysis of the binding of C3b to FB in the presence of D121. (FIG. 3D) SDS-PAGE of fractions from SEC analysis of C3b+FB+D121. (FIG. 3E) Updated comprehensive version of FIG. 3C.

FIGS. 4A-4F. (FIG. 4A) SEC shows that DI62 does not prevent binding of C3b to FB suggesting that it acts by preventing binding of the substrate C3 to both the CP and the AP C3 convertases. Panels B-E compare the ability of DI62 and hC3Nb1 to inhibit the AP (FIG. 4B+FIG. 4C), LP (FIG. 4D) and CP (FIG. 4E). DI62 is able to inhibit both AP, LP and CP. (FIG. 4F) Updated comprehensive version of FIG. 4A.

FIGS. 5A-5E. (FIG. 5A) SEC analysis of the binding of EWE-hC3Nb1 to C3b. (FIG. 5B) SEC analysis of C3b. (FIG. 5C) SEC analysis of the binding of EWE-hC3Nb1 to C3. (FIG. 5D) SEC analysis of C3. (FIG. 5E) SDS-PAGE analysis of peak fractions from the indicated chromatograms shown in A and C.

FIGS. 6A-6E. (FIG. 6A) SEC analysis of the binding of IgG-Fc-hC3Nb1 to C3b. (FIG. 6B) SEC analysis of IgG-Fc-hC3Nb1. (FIG. 6C) SEC analysis of the binding of IgG-Fc-hC3Nb1 to C3. (FIG. 6D) SEC analysis of C3. (FIG. 6E) SDS-PAGE analysis of peak fractions from the indicated chromatograms shown in A and C.

FIGS. 7A-7B. The inhibitory effects of the nanobodies on AP C3 cleavage. hC3Nb1 (W102A) is a mutant of hC3Nb1 that does not bind to C3 or C3b. (FIG. 7A) Inhibition of C3 deposition using NHS diluted 1:9. (FIG. 7BB) Inhibition of erythrocyte lysis using NHS diluted 1:6. The analysis includes measurement of the effect of Nbs on deposition of C3b on a surface of zymosan (FIG. 7A) or measurement of the effect of the Nbs on the lysis of rabbit erythrocytes (FIG. 8B) and is performed in a buffer eliminating the influence of CP and LP.

FIGS. 8A-8E: (FIG. 8A) SEC analysis of the interaction between C4 and hC4bNb6. (FIG. 8B) SEC analysis of the interaction between C4b and hC4bNb6. (FIG. 8C) SPR sensogram for apparent dissociation constant determination of C4:hC4bNb6. Full lines represent measured signal, dashed lines represent curve fit. (FIG. 8D) SPR sensogram for apparent dissociation constant determination of C4b:hC4bNb6. Full lines represent measured signal, dashed lines represent curve fit. (FIG. 8E) ka, kd and $K_D$ values±S.E.

FISG. 9A-9C: (FIG. 9A) SEC analysis of the interaction between C4 and hC4Nb8. (FIG. 9B) SEC analysis of the interaction between C4b and hC4bNb8.

(FIG. 10A) SEC analysis of the interaction between C4b and C2 in the presence of hC4bNb6 and SDS-PAGE of fractions. (FIG. 10B) SEC analysis of the interaction between C4b and C2 in the presence of hC4Nb8 and SDS-PAGE of fractions.

(FIG. 11A) Inhibitory action of hC4bNb6 and hC4Nb8 on deposition of C4b in a CP activation assay on a surface of deposited IgG. 59IF75 is C1q inhibitor IF75 described above. None of the nanobodies inhibits C4 deposition. (FIG. 11B) Inhibitory action of hC4bNb6 and hC4Nb8 on deposition of C3b in a CP activation assay on a surface of deposited IgG. 59IF75 is C1q inhibitor IF75 described above. Two additional C4/C4b specific Nbs, hC4bNb4 and hC4bNb5 are also inhibitory, but with lower efficacy as compared to hC4bNb6 and hC4Nb8. The C2 specific hC2NbG5 used here has little effect on CP C3 deposition FIGS. 12A-12E. Bispecific C1q nanobodies and their ability to recruitment C1q and activate complement. (FIG. 12A) Constructs used in experiments. (FIG. 12B) Flow cytometry measurement of recruitment of C1q from human serum to Raji cells by BiCE161 (left). Incubation with BiCE161 results in complement activation and C3 deposition (right). Data are normalized. (FIG. 12C) Complement activation and C3 deposition by indicated bispecific nanobodies on EGFR expressing MDA-MB-468 cells. (FIG. 12D) Updated comprehensive version of FIG. 12B. (FIG. 12E) Updated comprehensive version of FIG. 12C.

FIGS. 13A-13H. Ability of DF85 and BiCE128 to recruit C1q and activate complement on different tumor cell lines. (FIG. 13A) Recruitment of C1q from human serum to MDA-MB-468, A431 and A1207 cells by DF85. (FIG. 13B) C3 deposition on MDA-MB-468, A431 and A1207 cells by DF85. (FIG. 13C) Recruitment of C1q from human serum to A431 and A1207 cells by BiCE161. (FIG. 13D) C3 deposition on A431 and A1207 cells by BiCE161. (FIG. 13E) Updated comprehensive version of FIG. 13A. (FIG. 13F) Updated comprehensive version of FIG. 13B. (FIG. 13G) Updated comprehensive version of FIG. 13C. (FIG. 13H) Updated comprehensive version of FIG. 13D.

(FIG. 23A) C3d deposition in the presence of control nb, D121 and hC3nb2 upon activation of the alternative pathway. D121 inhibits C3d deposition in a concentration dependent manner and DI62 inhibits at 10 µg/ml. (FIG. 23B) C3d deposition in the presence of control nb, D121 and hC3nb2 upon activation of the classical pathway. DI62 inhibit C3d deposition upon activation of the classical pathway while D121 and control nanobody have no effect on C3d deposition.

DETAILED DESCRIPTION

Figure 1:
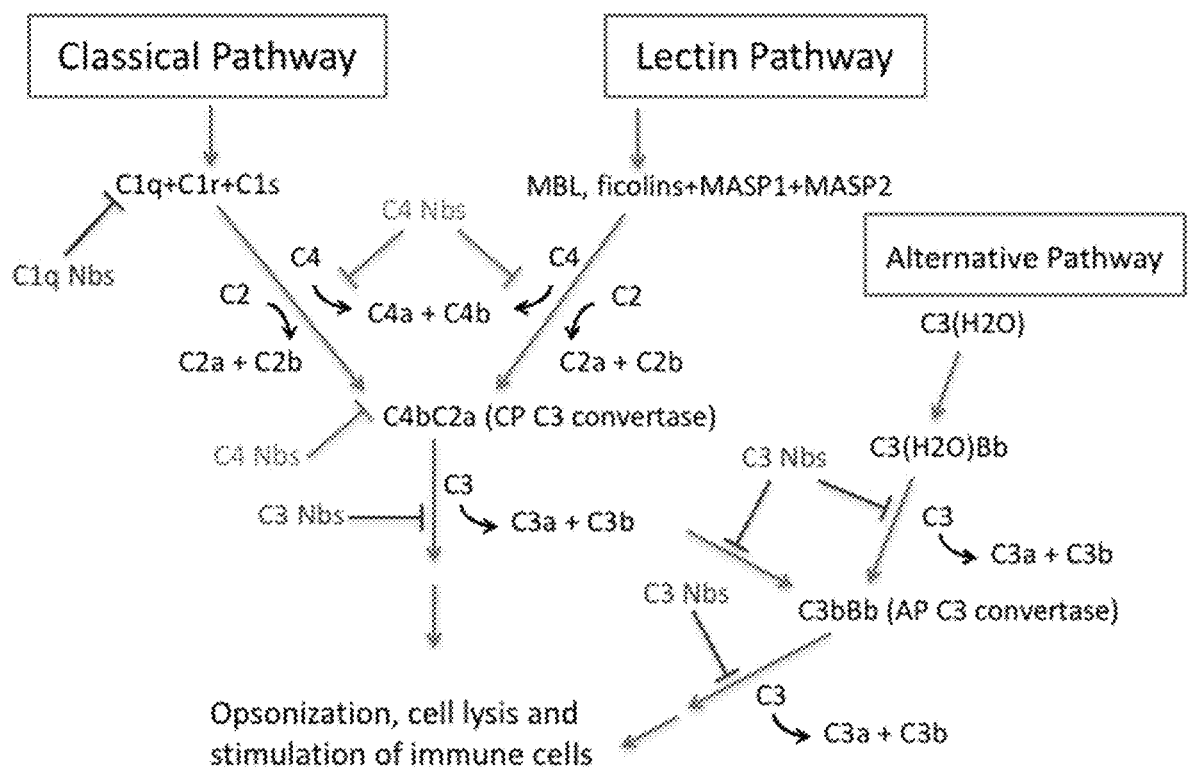
FIG. 1. Activation of the complement system and indications of where the identified Nbs (Nanobodies) inhibit complement.

Here, single domain antibodies, also called nanobodies (Nbs), are provided, which are derived from heavy-chain only camelid antibodies. The single domain antibodies disclosed herein are able to inhibit one or more complement pathways by specific binding to complement proteins. In order to facilitate the understanding of the invention, a number of important concepts are defined below.

Definitions

An "antibody" is a polypeptide or protein capable of recognising and binding an antigen comprising at least one antigen binding site. Said antigen binding site preferably comprises at least one complementarity determining region (CDR). The present disclosure relates primarily to single domain antibodies.

The "single domain antibodies", as referred to herein, comprises only one single domain or fragment of a domain of a whole antibody. The single domain may be a heavy chain constant region ($C_H$), a heavy chain variable region ($V_H$), a light chain constant region ($C_L$) or a light chain variable region ($V_L$) or a fragment thereof. In a preferred embodiment the single domain is a heavy chain variable region ($V_H$). The single domain antibody is preferably derived from llama.

An "antigen" is a molecule comprising at least one epitope. The antigen may for example be a polypeptide, nucleic acid, polysaccharide, protein, lipoprotein or glycoprotein.

A "complementarity determining region" or "CDR" is a hypervariable region of the antigen-binding region of an antibody. The CDRs are interspersed between regions that are more conserved, termed framework regions (FRs). The antigen-binding region of an antibody may thus comprise one or more CDRs and FRs, usually in each variable domain three CDRs and four FRs arranged from amino-terminus to carboxy-terminus in the following order: FR1, CDR1, FR2, CDR2, FR3, CDR3, FR4.

An "epitope" is a determinant capable of specific binding to an antibody. Epitopes may for example be comprised within polypeptides or proteins. Epitopes may be continuous or discontinuous, wherein a discontinuous epitope is a conformational epitope on an antigen which is formed from at least two separate regions in the primary sequence of the protein, nucleic acid or polysaccharide.

Affinity: The strength of binding between receptors and their ligands, for example between an antibody and its antigen. The affinity of an antibody can be defined in terms of the dissociation constant, $K_D$, which is an equilibrium constant that measures the propensity of a molecular complex to separate (dissociate) reversibly into the molecules forming the complex. In one aspect, $K_D$ is defined as the ratio $k_{off}/k_{on}$, where $k_{off}$ and $k_{on}$ are the rate constants for association and dissociation of the molecular complex. Preferably affinity is determined by calculating the dissociation constant $K_D$ based on $IC_{50}$ values. Thus, the affinity is measured as an apparent affinity.

The term "residues", as used herein, generally refers to single monomers collectively making one polymer. More specifically, the monomers combined in making the single-domain antibodies provided herein, consist of amino acids making up a polypeptide or protein.

The term "linker", as used herein, refers to a molecular moiety used to covalently bind two molecules to one another. The linker may be of varying length and structure and may comprise different anchoring groups. In one embodiment, the anchoring group may be selected from the group consisting of amine, carboxylic acid, acid chloride, N-hydroxysuccinimide ester, maleimide, thiol or a polypeptide.

The term "treatment", as used herein, refers to any process, action, application, therapy, or the like, wherein a subject, including a human being, is subject to medical aid with the object of improving the animal's condition, directly or indirectly. Thus, a treatment may involve curative treatment, ameliorating treatment and/or prophylactic treatment, where prophylactic treatment can result in complete prevention of a clinical and/or physiological condition or reduce the severity, such as reducing the number of and severity of any symptom associated with the clinical and/or physiological condition.

The Complement System

The present invention relates to single domain antibodies targeting one or more human complement factors and thereby being able to modulate activation of the complement system.

The complement system is part of the innate immune system and plays an important role in protection against invading microorganisms and in maintenance of homoeostasis. The innate immune system is not adaptable and does not change over the course of an individual's lifetime. More than 50 proteins and protein fragments make up the complement system, including serum proteins, serosal proteins, and cell membrane bound receptors and regulatory proteins. A subset of the complement proteins circulates as inactive precursors (pro-proteins). When stimulated by one of several triggers, proteases in the system cleave specific proteins to initiate an amplifying cascade of further cleavages. The end-result of this activation cascade includes massive amplification of the response, enhanced phagocytosis and pathogen lysis, clearance of immune complexes and apoptotic cells, inflammation, stimulation of adaptive immune responses and assembly of the cell-killing membrane attack complex.

Uncontrolled activation or lack of proper regulation of complement is involved in a range of diseases and the present invention therefore provides means for pharmacological regulation of the complement cascade in order to ameliorate disease outcome.

More specifically, the complement system is activated by three different proteolytic pathways: The classical pathway (CP), the lectin pathway (LP) and the alternative pathway (AP) (FIG. 1). Activation of the complement system results in cleavage of the complement proteins C3 (all pathways) and C4 (the classical and lectin pathway) into C3a and C3b, and C4a and C4b, respectively. After a certain threshold of C3b density is reached on the complement activating surface activation of the terminal pathway (TP) results in cleavage of complement C5.

The CP is activated by the C1 complex formed by the pattern recognition molecule C1q and the serine proteases C1r and C1s. C1 recognizes several different ligands including antigen bound antibodies, which leads to activation of the C1 complex, but may also directly recognize danger-associated molecular patterns (DAMPs) and pathogen associated molecular patterns (PAMPs). C1 cleaves C4 into C4a and C4b, and C2 can now bind to C4b, and C2 is then cleaved by the C1 complex into C2a and C2b. C4bC2a is the CP C3 convertase that cleaves C3 into C3a and C3b.

The LP is initiated by recognition of carbohydrate or acetylated pathogen-associated molecular patterns (PAMPs) by mannose binding lectin (MBL), the collectin CL-LK and three ficolins, respectively. MBL. CL-LK and the ficolins are associated with MBL-associated serine proteases (MASP)-1 and -2 that are activated upon binding of MBL, CL-LK and ficolins to DAMPs and PAMPs. MASP-1 and MASP-2 activation triggers the same proteolytic cascade as the classical pathway and also leads to assembly of the CP C3 convertase.

The AP may be activated by a spontaneous hydrolysis of an internal thioester in C3, resulting in formation of $C3(H_2O)$. $C3(H_2O)$ associates with the protease factor B (FB), which is cleaved by factor D into Bb and Ba. The complex between $C3(H_2O)$ and Bb is the fluid phase AP C3 convertase that cleaves C3 into C3a and C3b. C3b reacts with nearby nucleophiles on surfaces and become covalently attached to these resulting in activator bound C3b. Such C3b associates with FB that is cleaved and the AP C3 convertase, C3bBb is formed. The AP C3 convertase cleaves C3 into C3b and C3a and more AP convertase is formed in an amplification loop (FIG. 1). The activator bound C3b may also originate from C3 cleavage conducted by the CP C3 convertase, and indeed the AP C3 convertase strongly amplifies the initial C3 cleavage taking place in the CP and LP.

The single domain antibodies provided herein target human complement factors, in particular a human complement factor selected from the group consisting of C1q, C3, C4 and/or the proteolytic derivatives C3b and C4b.

Binding of one or more of the single domain antibodies to any of the complement factors affects the activity of the complement system. In a preferred embodiment, the single domain antibody is capable of inhibiting activation of the complement system.

For example, antibodies targeting C1q are capable of inhibiting interaction with C1r and/or C1s or prevent C1q interaction with a CP activator and thereby inhibit assembly and/or activation of the C1 complex in the classical pathway.

Antibodies targeting C3 and/or C3b are capable of inhibiting interaction between C3b and the zymogen FB or the active Bb and thereby inhibit assembly of the C3bBb convertase complex and/or the activity of the C3bBb convertase, and/or are able to prevent binding of C3 to the C3 convertases of the alternative pathway and the classical pathway which in turn inhibits C3 cleavage.

Antibodies targeting C4 and/or C4b are capable of inhibiting interaction between the zymogen C2 or the active C2a with C4b and thereby inhibit assembly of the C4bC2a complex and/or the activity of the C4bC2a complex, which in turn inhibits activation of the classical and lectin pathways.

In the context of the present disclosure, it is understood that complement factor C4 includes both native allotypes, C4A and C4B; cf. SEQ ID NO: 6 and 80.

Single-Domain Antibodies

Naturally occurring human antibodies are heterotetramers. The antibodies provided herein in one aspect comprise an antigen binding site in a single polypeptide. The antibodies are therefore herein referred to as "single domain antibodies". Single domain antibodies are also known as nanobodies. The single antibodies disclosed herein may, though, in certain embodiment be bispecific or multispecific single domain antibodies as described elsewhere herein, where to single domain antibodies are coupled.

A single domain antibody is an antibody fragment consisting of a single monomeric variable antibody domain. Like a whole antibody, it is able to bind selectively to a specific antigen. Single domain antibodies typically have molecular weights in the range of 12-15 kDa, i.e. much lower than common antibodies, ranging typically from 150 to 160 kDa. Single domain antibodies are also smaller than Fab fragments (~50 kDa) of heterotetrameric antibodies comprising one light chain and half a heavy chain.

Single domain antibodies can derive from antibodies found in nature, for example in camelids ($V_HH$) and cartilaginous fishes ($V_{NAR}$). New or Nurse Shark Antigen Receptor (NAR) protein exists as a dimer of two heavy chains with no associated light chains. Each chain is composed of one variable (V) and five constant domains. The NAR proteins thus constitute a single immunoglobulin variable-like domain. Single heavy-chain antibodies are also found in camelids, such as such as dromedaries, camels, llamas and alpacas, where the heavy chain has lost one of its constant domains and underwent modifications in the variable domain, both of which are structural elements necessary for the binding of light chains.

However, single domain antibodies can also be engineered by recombinant methods. One approach is to split the dimeric variable domains from common immunoglobulin G (IgG) from humans or mice into monomers. Single domains, which are derived from light chains, also bind specifically to target epitopes. Thus, the single domain antibody may be derived from any suitable organism.

Single domain camelid antibodies are equal to regular antibodies in terms of specificity. Single domain antibodies are easily isolated, for example by using phage panning procedures. The smaller size and single domain architecture make these antibodies easier to express as proteins in bacterial cells for large scale production, making them ideal for commercial exploitation. The antibodies of the present invention are therefore single domain antibodies, preferably derived from camelid antibodies, preferably llama antibodies, including functional homologs, fragments thereof and fusion macromolecules containing VHH covalently linked to glycan, nucleic acid, protein, or chemical groups not being a macromolecule.

The single domain VHH antibodies of the present invention preferably comprise one or more CRDs. In particular, the CDRs may identify the specificity of the antibody and accordingly it is preferred that the antigen binding site comprises one or more CDRs, preferably at least 1, more preferably at least 2, yet more preferably 3 or more CDRs. In one specific embodiment, the single domain antibody comprises 3 CDRs.

Thus, the single-domain antibodies provided herein are preferably derived from natural antibodies, such as camelid antibodies, most preferred llama antibodies. The single-domain antibodies provided herein also include functional variants thereof. The term "functional variant" is meant to include those variants, which retain some or essentially all the ability of an antibody to selectively binding its antigen or ligand, such as any of the ligands mentioned herein below. Functional variants include any variant, which is at least 75% identical to a single-domain antibodies provided herein, such as at least 80, 81, 82, 83, 84, 85, 86, 87, 88, 89, such as 90, 91, 92, 93, 94, 95, 96, such as 97, such as 98, such as 99, such as at least 99.5% identical to a single-domain antibody provided herein, such as any of those identified by SEQ ID NOs: 9, 13, 17, 21, 25, 29, 33, 37, 41, 45, 49, 53, 57 and 61.

In particular, functional variants include any variant antibody comprising one or more CDR, which is at least 75% identical to a CDR of a single-domain antibodies provided herein, such as at least 80, 81, 82, 83, 84, 85, 86, 87, 88, 89, such as 90, 91, 92, 93, 94, 95, 96, such as 97, such as 98, such as 99, such as at least 99.5% identical to said CDR. The CDRs of the respective antibodies identified by SEQ ID NOs: 9, 13, 17, 21, 25, 29, 33, 37, 41, 45, 49, 53, 57 and 61 are indicated below as SEQ ID Nos: 10-12, 14-16, 18-20, 22-24, 26-28, 30-32, 34-36, 38-40, 42-44, 46-48, 50-52, 54-56, 58-60, and 62-64, respectively. Thus, single domain antibodies are provided, which comprise one or more region having at least 75%, such as at least 80, 81, 82, 83, 84, 85, 86, 87, 88, 89, such as 90, 91, 92, 93, 94, 95, 96, such as 97, such as 98, such as 99, such as at least 99.5% identity to one or more regions identified by any one of SEQ ID Nos: 10-12, 14-16, 18-20, 22-24, 26-28, 30-32, 34-36, 38-40, 42-44, 46-48, 50-52, 54-56, 58-60, and 62-64.

Any amino acid substitutions preferably do not include conservative amino acid substitutions, which refer to substitution of one amino acid with another amino acid residue having a side chain with similar properties. For example, a group of amino acids having aliphatic side chains is glycine, alanine, valine, leucine, and isoleucine; a group of amino acids having aliphatic-hydroxyl side chains is serine and threonine, a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Within the meaning of the term "conservative amino acid substitution" as applied herein, one amino acid may be substituted for another within the groups of amino acids indicated herein below:
  i) Amino acids having polar side chains (Asp, Glu, Lys, Arg, His, Asn, Gln, Ser, Thr, Tyr, and Cys,)
  ii) Amino acids having non-polar side chains (Gly, Ala, Val, Leu, Ile, Phe, Trp, Pro, and Met)
  iii) Amino acids having aliphatic side chains (Gly, Ala Val, Leu, Ile)
  iv) Amino acids having cyclic side chains (Phe, Tyr, Trp, His, Pro)
  v) Amino acids having aromatic side chains (Phe, Tyr, Trp)
  vi) Amino acids having acidic side chains (Asp, Glu)
  vii) Amino acids having basic side chains (Lys, Arg, His)
  viii) Amino acids having amide side chains (Asn, Gln)
  ix) Amino acids having hydroxy side chains (Ser, Thr)
  x) Amino acids having sulphur-containing side chains (Cys, Met),
  xi) Neutral, weakly hydrophobic amino acids (Pro, Ala, Gly, Ser, Thr)
  xii) Hydrophilic, acidic amino acids (Gln, Asn, Glu, Asp), and
  xiii) Hydrophobic amino acids (Leu, Ile, Val)

Functional variants of antibodies may in one preferred embodiment be a fragment of an antibody, preferably an antigen-binding fragment or a variable region. Examples of antibody fragments useful with the present invention include fragments of $V_HH$ and $V_{NAR}$.

The single-domain antibodies may thus be obtained by immunization of any suitable organism, in particular camelids, sharks or the like.

However, the single domain antibodies could also be generated from a synthetic library with randomized or designed CDR's In one embodiment, a single domain antibody capable of specifically binding to an epitope of a human complement factor selected from the group consisting of C1q, C4 and/or the proteolytic derivative C4b, C3 and/or the proteolytic derivative C3b is provided.

In a preferred embodiment, the single-domain antibody comprises a variable region including a polypeptide consisting of the amino acid sequence represented by SEQ ID Nos: 10-12, 14-16, 18-20, 22-24, 26-28, 30-32, 34-36, 38-40, 42-44, 46-48, 50-52, 54-56, 58-60, and 62-64.

In addition, the single domain antibodies provided herein may be coupled to a tag, such as any purification tag or detectable label. In one embodiment, the single domain antibody is coupled to a histidine tag, such as a his6 tag at the N- or C-terminus of the polypeptide. In another embodiment, the single domain is coupled to an Fc-fragment at the N-terminal. N-terminal additions are particularly preferred, and in a preferred embodiment, the single domain antibody provided herein comprises an additional N-terminal region. The additional N-terminal region can be selected from any relevant additional moieties, depending on the contemplated application of the antibody and the desired functionalities to the final antibody product. Albumin may be added for increasing circulation time and protect the product from degradation. Other antigen binding fragments, single domain antibodies or fragments thereof may be added for introducing a second affinity/binding specificity to the antibody product.

In one embodiment, the single domain antibody is selected from the group consisting of EA57, IF75, IF78, IH31, IH33, IH35, IH37, IH39, hC4bNb6, hC4Nb8, D121, DI62, EWE-hC3Nb1 and IgG-Fc-hC3Nb1, identified by SEQ ID Nos: 9, 13, 17, 21, 25, 29, 33, 37, 41, 45, 49, 53, 57 and 61, respectively. In a preferred embodiment, the single domain antibody is selected from the group consisting of IF75, IH37 and EA57. In another preferred embodiment, the single domain antibody is EWE-hC3Nb1 or IgG-Fc-hC3Nb1. In another embodiment, the single domain antibody is selected from the group consisting of hC4bNb6, hC4Nb8, D121 and DI62.

Epitope

The single domain antibodies provided herein are capable of specifically binding to an epitope of a human complement factor. In a preferred embodiment, the antibody is capable of specifically binding to an epitope of a human complement factor selected from the group consisting of C1q, C3, C4 and/or the proteolytic derivatives C3b and C4b. Thus, the single domain antibody is capable of specifically binding to an epitope in a region in any of the polypeptide sequence identified by SEQ ID Nos: 1-8, 74-75 and 80-82.

In a preferred embodiment, the antibody is capable of specifically binding an epitope selected from
  an epitope, wherein at least a part of the epitope is situated in the region of
    i) human C1q chain a identified by SEQ ID NO: 3,
    ii) human C1q chain b identified by SEQ ID NO: 4,
    iii) human C1q chain c identified by SEQ ID NO: 5 and/or an epitope, wherein at least a part of the epitope is situated in the region of
  i) human C3 identified by SEQ ID NO: 1,
  ii) mouse C3 identified by SEQ ID NO: 2,
  iii) mouse C3 identified by SEQ ID NO: 74,
  iv) mouse C3 identified by SEQ ID NO: 75.
an epitope, wherein at least a part of the epitope is situated in the region of
  i) human C4A or C4B alpha chain,
  ii) human C4A or C4B beta chain and/or
  iii) human C4A or C4B gamma chain.
an epitope, wherein at least a part of the epitope is situated in the region of
  i) mouse C4 alpha chain identified by SEQ ID NO: 84,
  ii) mouse C4 beta chain identified by SEQ ID NO: 83, and/or
  iii) mouse C4 gamma chain identified by SEQ ID NO: 85.

The term "situated" as used in this context, means that the epitope is located or positioned in the specified region of the human C1q, C3, C3b, C4 or C4b.

It is preferred that the single domain antibodies as described herein binds their target complement factor with an affinity corresponding to a $K_D$ of about $10^{-4}$ M or less, such as about $10^{-5}$ M or less, such as about $10^{-6}$ M or less, $10^{-7}$ M or less, such as about $10^{-8}$ M or less, such as about $10^{-9}$ M or less, about $10^{-10}$ M or less, or about $10^{-11}$ M or even less, when measured based on apparent affinities based on EC50 values (the effective concentration achieving 50% of maximal binding) in an ELISA assay. In one embodiment, the antibody binds said complement factor with an affinity corresponding to a $K_D$ of about $10^{-6}$ M or less, such as $10^{-6}$ to $10^{-18}$ M.

The antibody may also or alternatively bind their target complement factor with an affinity corresponding to a $K_D$ that is at least ten-fold lower, such as at least 100-fold lower, such as at least 1000-fold lower than its affinity for binding to a non-specific antigen (e.g., BSA or casein).

The single domain antibody (or nanobody) may in some embodiment be cross-reactive. By cross-reactive is herein understood that the antibody reacts with an antigen from two or more species. Thus, it is an embodiment of the present invention that a single domain antibody binds one or more complement factors from one or more species. By way of example, the antibody may bind the human and mouse C4. Preferably the cross reactivity is between human and another mammalian species such as but not limited to mouse, rabbit, sheep, goat, pig, llama and horse. It is an object of the present invention to provide a single domain antibody, optionally an antibody which is bispecific, which binds human and mouse C3, human and mouse C3b, human and mouse C1q, human and mouse C4, and/or human and mouse C4b. The antibody may bind complement factors and/or their (proteolytic) derivatives from one or more species, preferably human and mouse.

TABLE 1

Overview of single domain antibodies and their antigens.

| | Antigen | | | | | | | | |
|---|---|---|---|---|---|---|---|---|---|
| | hC3 | hC3b | mC3 | mC3b | hC4 | hC4b | mC4 | mC4b | hC1q |
| Antibody | | | | | | | | | |
| DI62 | + | + | + | + | | | | | |
| D121 | + | + | + | + | | | | | |

TABLE 1 -continued

Overview of single domain antibodies and their antigens.

| | Antigen | | | | | | | | |
|---|---|---|---|---|---|---|---|---|---|
| | hC3 | hC3b | mC3 | mC3b | hC4 | hC4b | mC4 | mC4b | hC1q |
| EWE-hC3Nb1 | + | + | | | | | | | |
| IgG-Fc-hC3Nb1 | + | + | | | | | | | |
| hC4bNb6 | | | | | | + | + | | |
| hC4Nb8 | | | | | | + | | | |
| hC4Nb4 | | | | | | + | + | | |
| hC4Nb5 | | | | | | + | + | | |
| pNSL270 | | | | | | | + | + | |
| EA57 | | | | | | | | | + |
| IF75 | | | | | | | | | + |
| IF78 | | | | | | | | | + |
| IH31 | | | | | | | | | + |
| IH33 | | | | | | | | | + |
| IH35 | | | | | | | | | + |
| IH39 | | | | | | | | | + |

+ indicates binding.

All the antibodies listed in Table 1 are object of the present invention.

TABLE 2

Binding Constants - DI62.

| | KD | ka (1/Ms) | Ka (1/s) |
|---|---|---|---|
| Nat C3 | 5.5 nM | $1.0*10^5$ | $5.7*10^{-4}$ |
| C3b | 4.7 nM | $6.2*10^4$ | $2.9*10^{-4}$ |
| C3MA | 3.2 nM | $8*10^4$ | $2.6*10^{-4}$ |

Table 2 depicts the binding constants of the interaction between DI62 and native C3, C3b and C3MA.

Bispecific Single Domain Antibodies and Fusion Macromolecules

The single domain antibody may also be a bispecific antibody, e.g. a single peptide chain comprising two antigen-binding regions, which may each be separated by a linker sequence. The single domain antibody may also be a multivalent antibody, e.g. a single peptide chain comprising multiple antigen-binding regions, which may each be separated by linkers. The antigen-binding regions may be identical or different, yielding monospecific or heterospecific antibodies, respectively.

Thus, in one embodiment, a single domain antibody provided herein is coupled to another single domain antibody, yielding a bispecific antibody, which consists of or comprises
  i) one single domain antibody capable of specifically binding to an epitope of a human complement factor selected from the group consisting of C1q, C3, C4 and/or the proteolytic derivatives C3b and C4b and
  ii) one single domain antibody capable of specifically binding to an epitope of a second target.

The two or more single domain antibodies are coupled by a linker region. The linker can be chosen from any suitable linkers, such as polypeptide linkers. In one embodiment, the peptide linker comprises 5-50 amino acids, such as 5-30 amino acids, such as 5-20 amino acids, such as 5-10 amino acids. In one specific embodiment, the linker comprises 10 amino acids, for example GGGGSGGGGS.

In one embodiment, the second target is another complement factor. However, in preferred embodiments, the second target is a cancer-specific marker, such as any marker that is differentially expressed in cancer cells compared to non-malignant cells, where the marker is over-expressed on cancer cells. The second target is in another embodiment a pathogenic marker, in particular a microbial pathogen. In another embodiment, the second marker is a tissue-specific marker, an organ-specific marker, such as a marker specific for lung, eye, brain or kidney.

Single domain antibodies, which are capable of specifically binding to an epitope of a human complement factor selected from the group consisting of C1q, C3, C4 and/or the proteolytic derivatives C3b and C4b, are described elsewhere herein.

Single domain antibodies, which are capable of specifically binding to an epitope of a of a second target, include antibodies binding any target, for which the recruitment of a complement factor selected from C1q, C3, C4 and/or the proteolytic derivatives C3b and C4b is relevant.

For example, the coupling a single domain antibody specifically binding a complement factor to a cancer-specific target enables recruitment of complement factors and complement activation to the cancer target and consequently a targeted immunological response directed towards the cancer cells.

Similarly by coupling a single domain antibody specifically binding a complement factor to a single domain antibody specifically binding a pathogenic marker enables recruitment of complement factors and complement activation to the pathogen and consequently a targeted immunological response directed towards the pathogen. Coupling to the single domain antibody to another single domain antibody targeting specific tissues or organs could also be used to recruit complement factors to those specific tissues or organs leading to either activation or inhibition of the complement system at these tissues or organs.

Cancer-specific markers are for example EGFR and/or CD38, both cell bound receptors, which are upregulated in several cancer forms. Another group comprises cell specific marker proteins for example CD19 and CD20 both membrane proteins presented by B lymphocytes and validated targets for treatment of B cell lymphomas. Other examples of suitable markers are cMET, CD33, CD22, CD52, VEGF, PSMA, EpCam, HER, GD3, Erb2 and CD30.

Pathogenic markers include markers of bacterial, viral and fungal infections. These include for example the structures making up the membrane of gram negative bacteria like LPS or conserved proteins and structures in the membrane. Relevant markers could be part of the peptidoglycan cell wall of Gram positive bacteria like teichoic acid lipoteichoic acid. Suitable markers for viral infections include surface proteins on viral particles like influenza hemagglutinin or HIV-1 envelope trimer. Fungal infections can be targeted via conserved fungal surface antigens Bispecific single domain antibodies can be used to recruit and activate the complement cascade to specific targets, such as cancer sites or sites of infections, and thereby specifically activate an innate immune response at a specific target.

Such bispecific antibodies are therefore particularly useful in medicine for use as a medicament, and particularly for use in treatment of cancer and/or microbial infections.

In one aspect, the single domain antibodies provided herein, which are capable of specifically binding to an epitope of a human complement factor selected from the group consisting of C1q, C3, C4 and/or the proteolytic derivatives C3b and C4b are fused to another entity or moiety, For example, the single domain antibody may be covalently linked to a glycan, PEG, nucleic acid, protein, such as albumin, Fc-fusion or linked other chemical groups, such as small chemical molecules.

Antibody Modifications

The single domain antibodies disclosed herein above, may in preferred embodiments comprise modifications, which improve the function of the antibody.

For example, it is not always desirable to use non-human antibodies for human therapy, and accordingly the single domain antibodies provided herein may be a humanized antibody.

The antibody according to the invention may be a humanized antibody. A human antibody as used herein is an antibody, which is obtained from a system using human immunoglobulin sequences. Human antibodies may for example be antibodies isolated from an animal (e.g., a mouse) that is transgenic or transchromosomal for human immunoglobulin genes or a hybridoma prepared therefrom. Human antibodies may also be isolated from a host cell transformed to express the antibody, e.g., from a transfectoma. Human antibodies may also be isolated from a recombinant, combinatorial human antibody library or directly cloned from human B cells.

Human antibodies have variable and constant regions derived from human germline immunoglobulin sequences. In certain embodiments, however, such recombinant human antibodies can be subjected to in vitro mutagenesis or in vivo somatic mutagenesis and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

A human antibody is preferably at least 90%, more preferably at least 95%, even more preferably at least 96%, 97%, 98%, or 99% identical in amino acid sequence to the amino acid sequence encoded by a wild type human immunoglobulin gene.

Said transgenic of transchromosomal animal may contain a human immunoglobulin gene miniloci that encodes unrearranged human heavy (u and/or y) and K light chain immunoglobulin sequences. Furthermore, the animal may contain one or more mutations that inactivate the endogenous heavy and light chain loci.

The single domain antibody of the invention may be a chimeric antibody, i.e. an antibody comprising regions derived from different species. The chimeric antibody may for example comprise variable regions from one species of animal and constant regions from another species of animal. For example, a chimeric antibody can be an antibody having variable regions which derive from a lama monoclonal antibody and constant regions which are human. Such antibodies may also be referred to as humanized antibodies. The single domain antibodies can advantageously be humanized in order to prevent immunological reactions of the human organism against the antibody.

Thus, the single domain antibodies provided herein may be a humanized antibody, which is encoded partly by sequences obtained from human germline immunoglobulin sequences and partly from other sequences. Said other sequences are preferably germline immunoglobulines from other species, which produce single domain antibodes, most preferably from camelidae species, such as llama. In particular a humanized antibody may be an antibody in which the antigen binding site is derived from an immunoglobulin from lama, whereas some or all of the remaining immunoglobulin-derived parts of the molecule is derived from a human immunoglobulin. The antigen binding site from said lama may for example consist of a complete $V_HH$ or one or more CDRs grafted onto appropriate human framework regions. Thus, in a humanized antibody, the CDRs can be from camelids or cartilaginous fishes, preferably lama, and the other regions of the antibody are of human origin.

In other embodiments, the single domain antibodies are modified by codon optimization or other modifications introduced in order to enhance the function of the antibody.

Composition

One aspect of the present invention relates to a composition comprising one or more of the single domain antibodies provided herein. In one preferred embodiment, the composition is a pharmaceutical composition.

A pharmaceutical composition is a composition comprising one or more substances that have medicinal properties, together with a pharmaceutical acceptable carrier. Details of pharmaceutical compositions are provided herein below.

The single domain antibodies can be formulated as pharmaceutical compositions and administered to a mammalian host, such as a human patient in a variety of forms adapted to the chosen route of administration. Routes for administration include, for example, intravenous, intra-arterial, subcutaneous, intramuscular, intraperitoneal, intravitreal and other routes selected by one of skill in the art. Administration can also be achieved by nebulization. In another approach, the single domain antibodies may be administered as DNA by AAV and then expressed from the vector Administration forms are described elsewhere herein.

Solutions of the antibodies can for example be prepared in water or saline, and optionally mixed with a nontoxic surfactant. Composition for intravenous or intra-arterial administration may include sterile aqueous solutions that may also contain buffers, liposomes, diluents and other suitable additives. The pharmaceutical composition may also comprise or include serum.

The pharmaceutical dosage forms suitable for injection or infusion can include sterile aqueous solutions or dispersions comprising the active ingredient that are adapted for administration by encapsulation in liposomes. In all cases, the ultimate dosage form must be sterile, fluid and stable under the conditions of manufacture and storage.

Sterile injectable solutions are prepared by incorporating the antibodies in the required amount in the appropriate solvent with various of the other ingredients enumerated above, as required, followed by filter sterilization.

Methods and Uses of the Antibody

The single domain antibodies and compositions provided herein can be used for both in vivo and in vitro methods as well as medical and non-medical procedures.

In one aspect, the single domain antibodies and compositions provided herein are provided for use as a medicament. In a preferred embodiment the single domain antibodies and compositions are provided for treatment of a disorder, a clinical or physiological condition associated with complement activity. The single domain antibodies and compositions can also be applied for use in the preparation of a medicament, for example for the treatment of a disorder, a clinical or physiological condition associated with complement activity.

Another aspect relates to a method of treating a disorder, a clinical or physiological condition associated with complement regulation, such as complement activation, said method comprising administering a therapeutically effective amount of a single domain antibody or composition as defined in any of the preceding claims to s subject in need thereof.

The antibodies can be used alone or coupled to, or combined with, therapeutically useful agents. Antibodies can be administered to mammals suffering from any disease caused by dysregulation or over activation of the complement system or any of the diseases or clinical conditions mentioned herein. Such administration can provide therapeutic and curative treatments, as well as prophylactic, preventative and/or ameliorating measures.

One aspect of the present invention relates to a method of modulating the activity of the complement system using the antibody according to the present invention. Thus, a method is provided of modulating the activity of the complement system, said method comprising
  a) providing a composition comprising a human complement factor selected from the group consisting of C1q, C3, C4 and/or the proteolytic derivatives C3b and C4b,
  b) contacting said composition with single domain antibody capable of specifically binding to an epitope of a human complement factor selected from the group consisting of C1q, C3, C4 and/or the proteolytic derivatives C3b and C4b, as defined elsewhere herein.

Thus, the methods and uses provided herein may involve the provision of a single domain antibody of the present invention for modulating the activity of the complement system, which means that some of the single domain antibodies are capable of inhibiting the activity of the complement system and other single domain antibodies are capable of activating or increasing the activity of the complement system. In particular, where the single domain antibody is administered locally or is coupled to an agent, which promotes a localized accumulation, the complement system can be targeted to a specific region of interest, for example a tumour site or a site of microbial infection.

The methods and uses provided herein are in certain embodiments capable of inhibiting the initiation of the classical pathway, the lectin pathway, and/or the alternative pathway.

In other embodiments, the methods and uses provided herein are capable of activating the classical pathway and thereby the alternative pathway.

For example, the single domain antibodies EA57, IF75 and IH37 are capable of specifically binding to an epitope of the human C1q thereby inhibiting C1q interaction with IgG. However, the same antibodies may be capable of activating the C1 complex when the antibody is bound to a surface.

Single domain antibodies D121, EWE-hC3Nb1 and IgG-Fc-hC3Nb1 bind C3b and C3(H2O) thereby being capable of inhibiting assembly and/or the activity of the C3bBb convertase and the $C_3$(H2O) convertase, which in turn inhibits the alternative pathway For this purpose, the single domain antibody hC3Nb1 comprising an additional N-terminal region is generally capable of specifically binding C3b and prevents binding of C3 to the C3 convertases. While any N-terminal addition is contemplated, specifically relevant additions include albumin, antigen-binding regions, such as other single domain antibodies and fragments thereof.

In particular, EWE-hC3Nb1 and IgG-Fc-hC3Nb1 specifically binds C3b and not C3. These antibodies are particularly useful in vivo setting, since C3 is present in high concentrations (>4 µM in serum) while C3b is only located locally at sites of complement activation. Furthermore, single domain antibodies also binding C3 may in certain in vivo applications lead to formation of large immune complexes, if formulated into a dimeric format such as an N-terminal Fc-fusion protein. The C3b specific antibodies therefore allow a highly specific targeting of C3b as compared to C3 and have fewer adverse effects during in vivo applications.

Single domain antibody DI62 binds C3 and C3b and prevents binding of C3 and C3b to the C3 convertases.

In one aspect, a method is provided of modulating the activity of the complement system. This method comprises a composition comprising a human complement factor selected from the group consisting of C1q, C3, C4 and/or the proteolytic derivatives C3b and C4b, and contacting the composition with a single domain antibody capable of specifically binding to an epitope of a human complement factor selected from the group consisting of C1q, C3, C4 and/or the proteolytic derivatives C3b and C4b, i.e. a single domain antibody as defined herein above.

The composition is typically a bodily fluid or a cell culture. In preferred embodiments, the composition is serum, plasma, blood or cerebrospinal fluid.

In one embodiment, the method is an in vitro method. An in vitro method, as referred to herein, is a method performed outside a living organism or outside the body of a living organism or an individual. The method may for example be performed in laboratory containers, such as in a test tube, an incubation vessel, petri dishes, flasks or the like. The single domain antibodies can thus be used in vitro for modulation of complement activation in cell cultures of any kind.

The in vitro method may comprise the steps of i) providing a composition comprising a human complement factor selected from the group consisting of C1q, C3, C4 and/or the proteolytic derivatives C3b and C4b; and ii) contacting said composition with said single domain antibody, thereby modulating the activity of the complement factors.

When contacting the composition with the single domain antibody, the antibody will bind and either block or stimulate the functional activity of the complement factor. The composition may comprise any protein or one or more proteins involved in the complement system, including serum proteins, serosal proteins, and cell membrane receptors. Proteins involved in the complement system include for example C2, C4, C5, C3b, C3a, C4a, C4bC2a, C5a, C3bBb, factor B, factor D, germline-encoded pattern recognition receptors (PRR's) (such as mannose-binding lectin (MBL) or ficolins), MBL-associated serine proteases (MASPs)-1 or -2, properdin, C1q, C1r or C1s, The composition may also comprise other proteins with a function equivalent to the function of one or more complement proteins, e.g. CVF.

PRRs bind to conserved structures present in large groups of microorganisms popularly referred to as pathogen-associated molecular patterns (PAMPs). Thus, the composition as described above may also comprise PAMPs. Examples of PAMPs include endotoxin or lipopolysaccharide of Gram-negative bacteria, lipoteichoic acid of Gram-positive bacteria and beta-glucan of fungi.

The composition may also comprise pathogenic and/or cancer-specific markers.

The composition may comprise components such as therapeutically useful agents as described elsewhere herein.

In an alternative embodiment the method is an in vivo method.

The in vivo method may comprise the steps of administering to an individual the single domain antibody and thereby modulating the activity of the complement system in said individual.

Preferably, the single domain antibody at least partially inhibits the activity of the complement system in said individual. However, in other embodiments, specific activating or recruiting antibodies can activate the complement system or stimulate the activity of the complement system, either in general (systemically) or by recruiting the relevant complement factor to which it binds to a specific target region, e.g. where the single domain antibody is a bispecific antibody, as described above.

In particular, the in vivo method may comprise the steps of administering to an individual the single domain antibody according to the invention in an amount sufficient to modulate, i.e. inhibit or increase the activity of the classical pathway, the lectin pathway and/or the alternative pathway in said individual.

The in vivo method may comprise the steps of administering to an individual suffering from a disorder or clinical or physiological associated with increased activity of the complement system a therapeutically effective amount of one or more of the single domain antibodies provided herein.

In another embodiment, the in vivo method comprises the steps of administering to an individual suffering from a disorder or clinical or physiological condition, which is treatable by increasing and/or recruiting the activity of the complement system, a therapeutically effective amount of one or more of the single domain antibodies provided herein, including bispecific antibodies.

The in vivo method may be any of the method of treating any of the clinical or physiological conditions mentioned herein.

Disorder, Clinical and Physiological Conditions

The composition or the single domain antibodies according to the invention may be used as a medicament for treatment of disorders, clinical or physiological conditions caused by a defect in the complement system or more specifically an increased activity of the complement system or lack of (sufficient) complement activation. Such disorders, clinical or physiological conditions that involve the complement system are described below. The pharmaceutical composition may be used for the treatment of any of those.

The single domain antibodies and compositions provided herein can be provided for treatment of any disorder selected from the group consisting of ocular diseases, neurological diseases, autoimmune and inflammatory disorders, cancers and infectious diseases.

Thus, in one preferred embodiment, the composition or the single domain antibodies are provided for use in treatment of ocular diseases. Ocular diseases may be selected from the group consisting of Occular, acute closed angle glaucoma, all stages of age-related macular degeneration (wet and dry), Behcet's retinopathy, Central Retinal Vein Occlusion (CRVO), choroidal neovascularization (CNV), Chronic open-angle glaucoma, corneal neovascularization, diabetic and other ischemia-related retinopathies, diabetic macular edema, diabetic retinopathy, endophthalmitis, Geographic atrophy, histoplasmosis of the eye, ischemia-related retinopathy, ischemic optic neuropathy, Leber's hereditary optic neuropathy, macular degenerative diseases, Neuromyelitis Optica (NMO), pathological myopia, Purtscher retinopathy, retinal neovascularization, Sjogren's dry eye disease Uveitis.

In another preferred embodiment, the composition or the single domain antibodies are provided for use in treatment of neurological diseases, such as diseases selected from the group consisting of Alzheimer's disease, schizophrenia, amyotrophic lateral sclerosis, Guillain-Barre syndrome, Huntington's disease, multiple sclerosis and Parkinson's disease.

In yet another preferred embodiment, the composition or the single domain antibodies are provided for use in treatment of autoimmune and inflammatory disorders, such as disorders selected from ANCA vasculitis, anti-nuclear cytoplasmic antigen-associated pauci-immune vasculitis (Wegener's syndrome), anti-phospholipid syndrome (APS), astma, atypical hemolytic uremic syndrome (aHUS), autoimmune hemolytic anemias, Bullous Pemphigoid, C3 glomerulonephritis, Coeliac disease, Cold agglutinin disease, Crohn's disease, cryogulbulemia, dense deposit disease, dermatomyositis, diabetes, Diabetes mellitus type 1, epidermolysis bullosa, Hashimoto's thyroiditis, hyperacute rejection. hypocomplementemic urticarial vasculitis (HUV), IgA nephropathy, intestinal and renal ischemia-reperfusion (IR) injury, lupus nephritis and resultant glomerulonephritis and vasculitis, Myasthenia Gravis, myositis, optic neuritis, paraneoplastic syndromes, paroxysomal nocturnal hemoglobinuria (PNH), pemphigus including Pemphigus vulgaris, polyarteritis nodosa, polymyalgia rheumatic, post-traumatic shock, acute renal failure, remote tissue injury after ischemia and reperfusion retinal vasculitis, rheumatoid arthritis (RA), sarcoidosis, sepsis, stroke, systemic lupus erythematosus (SLE), temporal arteritis, traumatic brain and spinal cord injury, type II membranoproliferative glomerulonephritis, vasculitis disease, vitiligo, acute respiratory distress syndrome (ARDS), chronic occlusive pulmonary distress syndrome (COPD), atherosclerosis, cardioplegia-induced coronary endothelial dysfunction, spontaneous and recurrent pregnancy loss, Addison's disease.

In another preferred embodiment, the composition or the single domain antibodies are provided for use in treatment of cancers such as carcinomas, sarcomas, lymphomas, leukaemia's, germ cell tumor, blastoma.

In another preferred embodiment, the composition or the single domain antibodies are provided for use in treatment of infectious diseases such as infections with bacteria, viruses, parasites or fungi.

Administration Forms

As described herein above, the single domain antibodies and/or compositions provided herein can be used for medical/therapeutic treatment. In these aspects, the single domain antibodies and/or compositions are administered to a subject in need of treatment, and any suitable route of administration may be chosen, depending on the circumstances. Preferred routes of administration are described herein below.

Systemic Treatment

The main route of administration is parenteral in order to introduce single domain antibodies according to the invention into the blood stream to ultimately target the sites of desired action.

Appropriate dosage forms for such administration may be prepared by conventional techniques.

Parenteral Administration

Parenteral administration is any administration route not being the oral/enteral route whereby the medicament avoids first-pass degradation in the liver. Accordingly, parenteral administration includes any injections and infusions, for example bolus injection or continuous infusion, such as intravenous administration, intramuscular administration, subcutaneous administration. Furthermore, parenteral administration includes inhalations and topical administration.

Accordingly, the single domain antibodies or compositions may be administered topically to cross any mucosal membrane of an animal to which the biologically active substance is to be given, e.g. in the nose, vagina, eye, mouth, genital tract, lungs, gastrointestinal tract, or rectum, preferably the mucosa of the nose, or mouth, and accordingly, parenteral administration may also include buccal, sublingual, nasal, rectal, vaginal and intraperitoneal administration as well as pulmonal and bronchial administration by inhalation or installation. Also, the agent or antibody may be administered topically to cross the skin.

The subcutaneous and intramuscular forms of parenteral administration are generally preferred.

Pharmaceutical Composition

Whilst it is possible for the single domain antibodies provided herein to be administered in raw form, it is preferred to present them in the form of a pharmaceutical composition. Accordingly, the present invention further provides a pharmaceutical composition, which comprises a single domain antibody of the present invention and a pharmaceutically acceptable carrier therefore. The pharmaceutical compositions may be prepared by conventional techniques, e.g. as described in Remington: The Science and Practice of Pharmacy 2005, Lippincott, Williams & Wilkins.

The pharmaceutically acceptable carriers can be either solid or liquid. Solid form preparations include powders, tablets, pills, capsules, cachets, suppositories, and dispersible granules. A solid carrier can be one or more excipients which may also act as diluents, flavoring agents, solubilizers, lubricants, suspending agents, binders, preservatives, wetting agents, tablet disintegrating agents, or an encapsulating material.

The single domain antibodies of the present invention may be formulated for parenteral administration and may be presented in unit dose form in ampoules, pre-filled syringes, small volume infusion or in multi-dose containers, optionally with an added preservative. The compositions may take such forms as suspensions, solutions, or emulsions in oily or aqueous vehicles, for example solutions in aqueous polyethylene glycol. Examples of oily or non-aqueous carriers, diluents, solvents or vehicles include propylene glycol, polyethylene glycol, vegetable oils (e.g., olive oil), and injectable organic esters (e.g., ethyl oleate), and may contain agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The single domain antibodies of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by rectal or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

Dosages and Dosing Regimes

The dosage requirements will vary with particular composition employed, the route of administration and the subject being treated. It will also be recognized by one of skill in the art that the optimal quantity and spacing of individual dosages of the single domain antibody will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of the antibody given per day for a defined number of days, may be ascertained using conventional course of treatment determination tests.

The daily oral dosage regimen may range from about 0.01 to about 80 mg/kg of total body weight. The daily parenteral dosage regimen may range from about 0.001 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day.

The single domain antibodies may be provided and/or administered as a unit dosage form. The term "unit dosage form" as used herein refers to physically discrete units suitable as unitary dosages for human and animal subjects, each unit containing a predetermined quantity of the single domain antibody, alone or in combination with other agents, calculated in an amount sufficient to produce the desired effect in association with a pharmaceutically acceptable diluent, carrier, or vehicle. The specifications for the unit dosage forms of the present invention depend on the particular antibody or antibodies employed and the effect to be achieved, as well as the pharmacodynamics associated with each antibody in the host. The dose administered should be an "effective amount" or an amount necessary to achieve an "effective level" in the individual patient.

When the "effective level" is used as the preferred endpoint for dosing, the actual dose and schedule can vary, depending on inter-individual differences in pharmacokinetics, drug distribution, and metabolism. The "effective level" can be defined, for example, as the blood or tissue level desired in the patient that corresponds to a concentration of one or more antibodies according to the invention.

The antibodies of the present invention may be formulated in a wide variety of compositions for parenteral administration.

For injections and infusions the compositions may take such forms as suspensions, solutions, or emulsions in oily or aqueous vehicles, for example solutions in aqueous polyethylene glycol. Alternatively, the single domain antibodies may be in powder form, obtained by aseptic isolation of sterile solid or by lyophilisation from solution for constitution before use with a suitable vehicle, e.g., sterile, pyrogen-free water. The compositions can be presented in unit dosage form or multi-dose sealed containers, such as ampoules, vials, pre-filled syringes, infusion bags, or can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Examples of oily or non-aqueous carriers, diluents, solvents or vehicles include propylene glycol, polyethylene glycol, vegetable oils, and injectable organic esters, and may contain formulatory agents such as preserving, wetting, emulsifying or suspending, stabilizing and/or dispersing agents.

The compositions for injection will typically contain from about 0.5 to about 25% by weight of the active ingredient in solution.

The compositions of the present embodiment may also include other agents useful for pH maintenance, solution stabilization, or for the regulation of osmotic pressure.

The compositions of the present embodiment may also include other agents useful for pH maintenance, solution stabilization, or for the regulation of osmotic pressure.

Method of Producing a Single Domain Antibody

One aspect of the present disclosure relates to methods of producing single domain antibodies as defined herein, i.e. single domain antibodies capable of specifically binding to an epitope of a human complement factor selected from the group consisting of C1q, C3, C4 and/or the proteolytic derivatives C3b and C4b. The single-domain antibodies may be obtained by immunization of any suitable organism. In particular, single-domain antibodies provided herein may be derived by immunization of any organism known to naturally possess immunoglobulins consisting of heavy chain only, such as camelids, sharks or the like.

Thus, one aspect relates to a method of producing a single domain antibody, said method comprising immunizing a camelid, such as such as a dromedary, camel, llama or an alpaca, with peptide comprising an epitope of a human complement factor selected from the group consisting of the human C1q, C3, C4 and/or the proteolytic derivatives C3b and C4b. The camelid is preferably a llama The relevant epitopes are epitopes are described herein above, and includes for example
  an epitope, wherein at least a part of the epitope is situated in the region of
    iv) human C1q chain a identified by SEQ ID NO: 3,
    v) human C1q chain b identified by SEQ ID NO: 4,
    vi) human C1q chain c identified by SEQ ID NO: 5 and/or
  an epitope, wherein at least a part of the epitope is situated in the region of human C3 identified by SEQ ID NO: 1.
  an epitope, wherein at least a part of the epitope is situated in the region of
    i) human C4A or C4B alpha chain identified by SEQ ID NO: 6 or 80,
    ii) human C4A or C4B beta chain identified by SEQ ID NO: 7 and/or
    iii) human C4A or C4B gamma chain identified by SEQ ID NO: 8.

The method preferably involves immunization of the animal, such as camelid, such as lama, with the desired epitope/antigen, is followed by isolating the mRNA encoding heavy-chain antibodies. Subsequently, the mRNA can be reverse transcribed and amplified by polymerase chain reaction (PCR), thereby producing a gene library of single-domain antibodies clones. Specific clones, which are capable of specifically binding to an epitope of a human complement factor selected from the group consisting of C1q, C3, C4 and/or the proteolytic derivatives C3b and C4b, can then be identified using screening techniques, such as phage display or ribosome display.

Upon identification of the most specific and high affinity single domain antibodies, their protein sequence can be optimized, for example to improve their stability towards enzymes. The relevant antibodies may also be humanized as described herein above to prevent immunological reactions of the human organism against the antibody. Camelid antibodies are easily humanized due to a large degrees of the homology between camelid $V_HH$ and human $V_H$ fragments. The single-domain antibody may be produced in cells of host organisms such as *Escherichia coli, Saccharomyces cerevisiae, Pichia pastoris, Spodoptera frugiperda, Trichoplusia ni, Homo sapiens*, CHO, or other suitable organisms by transferring the gene encoding the single domain antibody to said host organism and allowing the gene to be expressed in sufficient amounts for the resulting single domain antibody to be isolated. Such methods of heterologous gene expression are generally known in the art.

Method of Detecting the Presence of a Complement Factor

A number of highly specific and high affinity single domain antibodies are provided herein, which are capable of specifically binding to an epitope of a human complement factor selected from the group consisting of C1q, C3, C4 and/or the proteolytic derivatives C3b and C4b. Such antibodies can be used for detection of said complement factors as well as their interaction partners. Thus, in one aspect, a method is provided for detecting the presence of a complement factor, preferably a complement factor selected from the group consisting of the human C1q, C3, C4 and/or the proteolytic derivatives C3b and C4b. In this method, a single domain antibody as defined herein above is used as a detection agent. The single domain antibody is therefore preferably coupled to a detectable label.

The method for detecting the presence of a complement factor is in one embodiment an in vitro method. For example, such as in vitro method comprise the steps of
a. Providing a biological sample,
b. Providing a single domain antibody as defined herein above,
c. Bringing said single domain antibody into contact with said biological sample, and
d. Detecting the binding of said single domain antibody to one or more complement factors in said biological sample.

The method may preferably involve additional steps of washing away unbound single domain antibody from the sample and/or addition of secondary antibodies or other detection agents followed by detection of bound secondary antibodies or other detection agents.

In another embodiment, the method is an in vivo method, wherein said single domain antibody is administered to a subject followed by detection of the presence of the antibody in said subject.

The method for detecting the presence of a complement factor is in one preferred embodiment a diagnostic method, comprising administering the single domain antibody to a subject suffering or at risk of suffering of a disorder associated with complement activation and detecting the presence of the antibody in said subject.

The method may be applied for detecting concentration of complement factors in specific tissues of a subject.

In one embodiment, the diagnostic method is applied for determining the presence or risk of a disorder selected from the group consisting of Autoimmune and inflammatory disorders, such as disorders selected from ANCA vasculitis, anti-nuclear cytoplasmic antigen-associated pauci-immune vasculitis (Wegener's syndrome), anti-phospholipid syndrome (APS), astma, atypical hemolytic uremic syndrome (aHUS), autoimmune hemolytic anemias, Bullous Pemphigoid, C3 glomerulonephritis, Coeliac disease, Cold agglutinin disease, Crohn's disease, cryoglobulemia, dense deposit disease, dermatomyositis, diabetes, Diabetes mellitus type 1, epidermolysis bullosa, Hashimoto's thyroiditis, hyperacute rejection. hypocomplementemic urticarial vasculitis (HUV), IgA nephropathy, intestinal and renal ischemia-reperfusion (IR) injury, lupus nephritis and resultant glomerulonephritis and vasculitis, Myasthenia Gravis, myositis, optic neuritis, paraneoplastic syndromes, paroxysomal nocturnal hemoglobinuria (PNH), pemphigus including Pemphigus vulgaris, polyarteritis nodosa, polymyalgia rheumatic, post-traumatic shock, acute renal failure, remote tissue injury after ischemia and reperfusion retinal vasculitis, rheumatoid arthritis (RA), sarcoidosis, sepsis, stroke, systemic lupus erythematosus (SLE), temporal arteritis, traumatic brain and spinal cord injury, type II membranoproliferative glomerulonephritis, vasculitis disease, vitiligo, acute respiratory distress syndrome (ARDS), chronic occlusive pulmonary distress syndrome (COPD), atherosclerosis, cardioplegia-induced coronary endothelial dysfunction, spontaneous and recurrent pregnancy loss, Addison's disease.

In another embodiment, the diagnostic method is applied for determining the presence of complement activation during or after transplantation.

In another embodiment, the diagnostic method is applied for in-body/in vivo detection of activated C3b or C4b.

EXAMPLES

Example 1

Single Domain Antibodies Against C1q that Inhibit C1 Activation.

For selection of single domain C1q was purified by the protocol described by Tenner et al., 1981. Immunization and selection was performed using 0.4 mg of human C1q essentially as described by Jensen et al., 2018 for C3. Nanobodies were expressed in *E. coli* using 2×TY media overnight. Pelleted cells were resuspended in 20 mM Tris pH 8.0, 500 mM NaCl, 0.5 mM EDTA, 20 mM imidazole, sonicated and subjected to HisTrap crude FF (GE Healthcare) column. The nanobody was eluted by imidazole supplemented resuspension buffer. The eluted protein was dialyzed overnight against 20 mM acetic acid (pH 5.5), 50 mM NaCl, then applied to 1 mL Source 15S (GE Healthcare) column and eluted by a linear gradient from 50-500 NaCl. The eluted protein was subjected to size exclusion chromatography using Superdex 75 (GE Healthcare) column.

For CP deposition assays, 96-well Optical Bottom Microwell® Plates were coated with normal human IgG (nhIgG) diluted in carbonate buffer pH=9.6 (AmpliqON) to 15 µg/mL. The plates were incubated in humidity box at room temperature overnight, after which they were blocked by addition of human serum albumin (HSA) at 1 mg/ml diluted in TBS, 0.05% w/w Tween 20, 5 mM Ca2+(TBS/Tween/Ca2+) and incubated at room temperature for 1 hour. The plates were washed three times with TBS/Tween/Ca2+ (wash step). The samples containing the desired nanobody were added to the wells in duplicates and incubated for 1 hour at 37° C. in humidity box, followed by a wash step. The assay was developed by adding biotin kahC4c (Dako 0.78 mg/mL) at 0.5 g/mL concentration, diluted in TBS/Tween/Ca2+. The plates were incubated at 4° C. in humidity box overnight, followed by a wash step. Europium3+-streptavidin (1244-360; PerkinElmer, Waltham, MA) diluted to 0.1 mg/ml in TBS/Tween/25 µM EDTA was added to each well and protein deposition levels were quantified as the fluorescent signal from Eu3+, after addition of 200 µl enhancement buffer (AmpliqON) to each well. The signals were measured by time-resolved fluorometry using a VICTOR X5 plate reader (PerkinElmer), with an excitation and an emission wavelength of 350 nm and 610 nm, respectively.

The globular head of C1q (hC1gGH) was generated as described by Moreau et al. 2016, but now including a C-terminal his-tag. The protein was expressed by stably transfected HEK293F cells and loaded on a 1 ml HisTrap excel column. The column was washed in 50 ml PBS and eluted with PBS supplemented with 250 mM imidazole pH 8.0. The eluted protein was diluted in PBS containing 500 mM NaCl and loaded on a 1 ml HisTrap crude column. The column was washed with PBS containing 500 mM NaCl and 20 mM imidazole pH 8.0 and eluted with PBS supplemented with 250 mM imidazole pH 8.0. The eluted protein was concentrated and loaded on a Superdex 200 Increase column equilibrated in 20 mM hepes, 150 mM NaCl pH 7.5. To analyse complex formation between C1qGH and IF75, IF75 was mixed with C1qGH in a two-fold molar excess and loaded on an ENrich70 SEC 70 10×300 column equilibrated in 20 mM hepes, 150 mM NaCl pH 7.5. The eluted protein was analysed by SDS-PAGE.

Figure 2A:
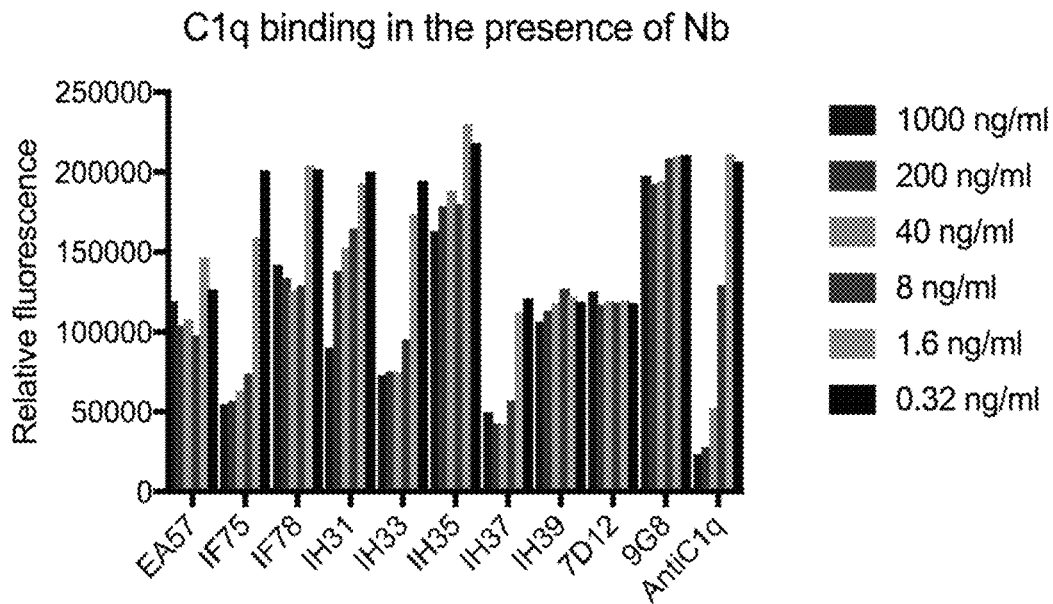
Figure 2B:
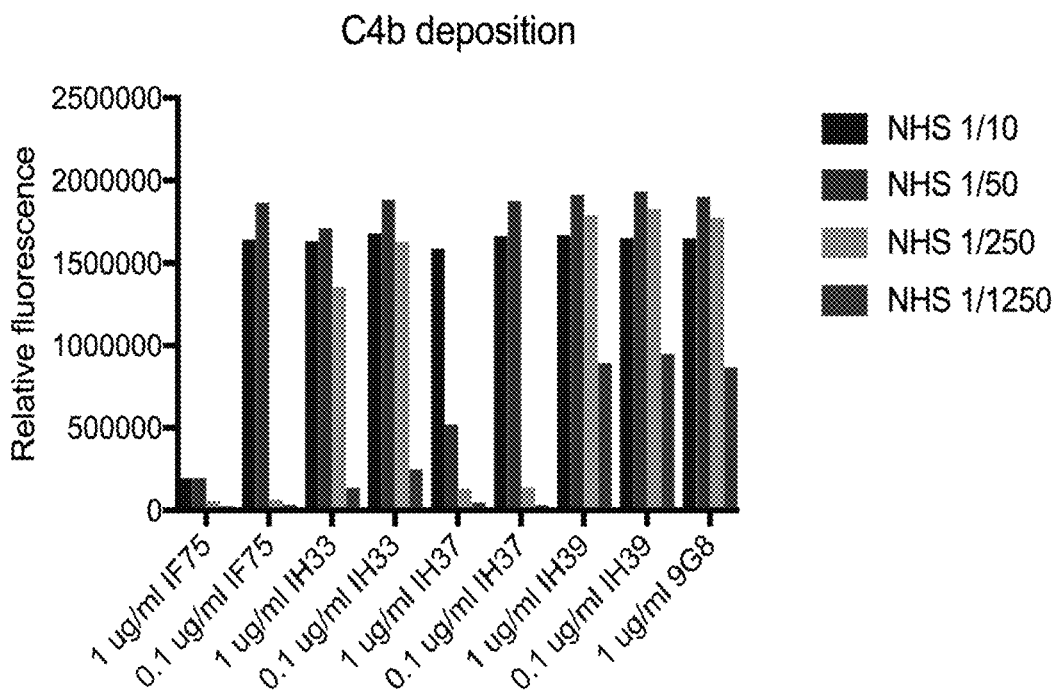

FIGS. 2A-2B shows binding of C1q to wells coated with IgG in the presence of increasing amount of C1q nanobodies (FIG. 2A) and the inhibitory effects of nanobodies on CP activation (FIG. 2B). As observed in FIG. 2A, IF75, IH33 and IH37 potently prevents the interaction with IgG while EA57, IF78, IH31 are less potent. IH35 and IH39 do not inhibit binding of C1q to IgG. As demonstrated in FIG. 2B, IH75, IH33 and IH37 inhibits C1 activation by IgG in a dose dependent manner.

Figure 17:
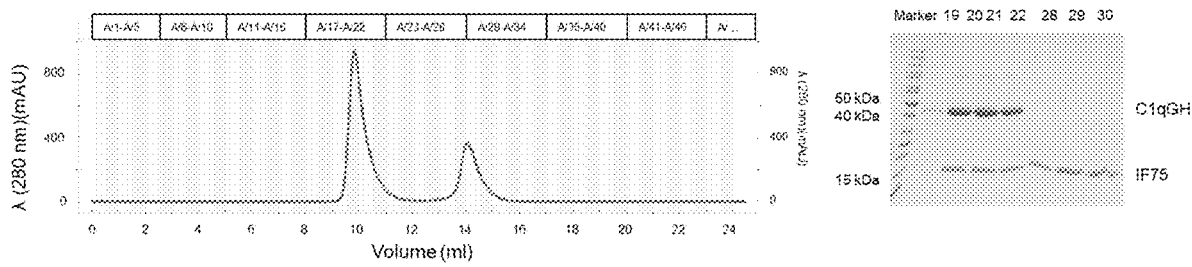
FIG. 17. SEC of the complex between the globular head of human C1q (hC1qGH) and IF75 on a ENrich 70 10/300 column (left). SDS-PAGE of indicated fractions (right). As seen from the SDS-PAGE IF75 interacts specifically with the head region of hC1q.
Figure 18:
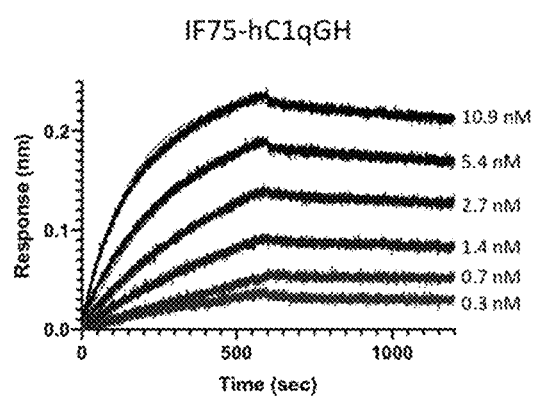
FIG. 18. Bio-layer interferometry (BLI) measurements of the interaction between hC1qGH and IF75. IF75 was immobilized on the sensors and numbers are concentrations of hC1qGH. Global fitting to the data shows that hC1qGH binds to IF75 with a dissociation constant of 0.5 nM.
Figure 19:
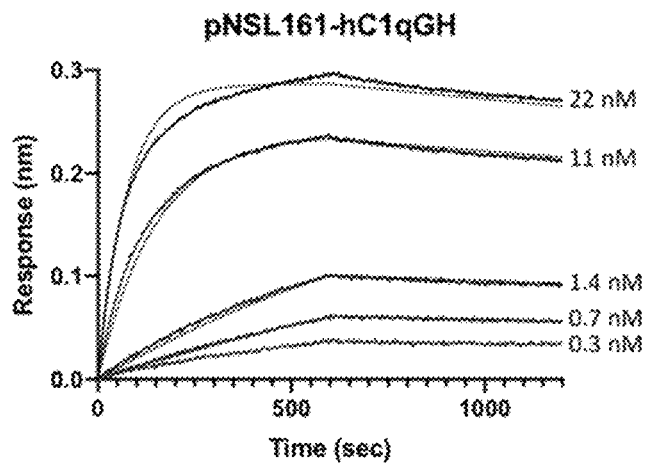
FIG. 19. Bio-layer interferometry (BLI) measurements of the interaction between hC1qGH and the bispecific nanobody pNSL161 composed IF75 linked to a CD38 specific nanobody. pNSL161 was immobilized on the sensors and numbers are concentrations of hC1qGH. Global fitting to the data shows that hC1qGH binds to pNSL161 with a dissociation constant of approximately 0.5 nM.

FIG. 17 shows that IF75 binds specifically to the globular head of C1q in SEC. The interaction was also measured by Bio-layer interferometry (BLI) as shown in FIG. 18. IF75 binds to hC1qGH with a dissociation constant (Kd) of 0.5 nM.

Example 2

Inhibitory Nanobodies Against C3 and C3b.

Native C3 was purified from outdated human plasma as descried elsewhere (Jensen et al., 2018). Similarly, C3b was generated from the purified native C3 as described elsewhere (Jensen et al., 2018). Immunization and selection of nanobodies D121 and DI62 were performed essentially as described by Jensen et al., 2018. Nanobodies were purified as described in Example 1. For negative stain electron microscopy, D121 was added in two fold molar excess to C3b followed by 5 min incubation on ice. The complex was purified using a Superdex 200 increase (GE Healthcare) size exclusion column equilibrated in 20 mM HEPES (pH 7.5), 150 mM NaCl. 3 µL complex from the early peak fractions were applied to glow-discharged carbon coated copper grid, followed by staining with 2% (w/v) uranyl formate. Image acquisition was performed on FEI Tecnai G2 Spirit transmission electron microscope operated at 120 kV. Automated image acquisition was performed using Leginon (Suloway et al., 2005), automated particle picking was performed using DoG picker (Voss et al., 2009). 2D and 3D classification was performed using RELION (Scheres, 2012).

For crystallization, D121 was added in 10% molar excess to mC3 C345c and subjected to size exclusion chromatography using a Superdex 75 (GE Healthcare) column equilibrated in 20 mM HEPES (pH 7.5), 150 mM NaCl. The complex was concentrated to 10 mg/mL and mixed in a 1:1 ratio with reservoir solution containing 17.5% PEG 4K, 33 mM NaOAc (pH 4.3), 66 mM NaOAc (pH 5.3), 0.2 M AmSO4 in a sitting drop crystallization setup at 19° C. Crystals were soaked in reservoir solution supplemented with 20% glycerol before being flash frozen in liquid nitrogen. Data was processed with XDS (Kabsch, 2010) and the structure was determined using the C345c and hC3nb1 for molecular replacement in Phaser (McCoy et al., 2007). The model was iteratively manually rebuilt in Coot (Emsley, 2007) and refined using Phenix.refine (Afonine, 2007). To assay inhibition of assembly of the AP C3 proconvertase, 50 µg C3b was added a 1.2-fold molar excess of FB (D279G S/A) and subjected to size exclusion chromatography either alone or in presence of a twofold molar excess of the indicated nanobody. The complexes were incubated for 5 min at 4° C. before being subjected to the size exclusion chromatography (SEC), which was performed at 4° C. on a Superdex 200 increase (GE Healthcare) equilibrated in 20 mM HEPES (pH 7.5), 150 mM NaCl, 3 mM MgCl2.

To assay cleavage by factor I, Factor H and Factor I was added to C3b and incubated 5 min on ice with a 1.2-fold molar excess of the nanobody. The reaction buffer was 150 mM NaCl, 20 mM HEPES (pH 7.5) and the Factor H and Factor I ratio was 1/500 and 1/100 mass ratio to C3b, respectively. The reaction mix was incubated at 37° C. Samples were obtained after 1, 2, 4, and 8 h, mixed with reducing SDS loading dye and boiled to prevent further cleavage.

To analyse cleavage by the CVFBb convertase, the CVFB proconvertase was prepared by mixing FB (D279A mutant) with a two-fold molar excess of CVF in 150 mM NaCl, 20 mM HEPES (pH 7.5), 2 mM $MgCl_2$. 10% (w/w) FD was added to activate the convertase, and the mix was incubated for 15 min at RT, then 10 min on ice. For EWE-hC3nb1 and D121, a 10-fold molar excess of C3 to FB was added and the reaction was incubated on ice, either in presence or absence of a two-fold molar excess (to C3) of the nanobody. For hC3nb2, a 10-fold molar excess of C3 to FB was added and the reaction was incubated at 37° C. in either the presence or absence of a two-fold molar excess (to C3) of the nanobody. Samples were obtained after 0.5, 1, 2, 4, 8, and 24 h, mixed with reducing SDS loading dye and boiled to prevent further cleavage.

To measure the interaction between nanobodies and C3 or C3b Bio-layer interferometry (BLI) experiments were performed in 20 mM HEPES (pH 7.5), 150 mM NaCl, 0.05% (v/v) Tween 20 on an Octet RED96 instrument (FORTÉBIO Pall Corporation). Biotinylated nanobody, at 5 µg/mL, was immobilized on streptavidin biosensor (FORTEBIO Pall Corporation). Nanobody coated biosensors were transferred to native C3 or C3b at concentration 6.25, 12.5, 25, and 50 nM with an association time of 600 sec. Upon association, a 1400 sec dissociation step was performed.

For the D121/FP/miniFH competition assay, miniFH was immobilized on amine reactive sensors (AR2G, ForteBio). The sensors were equilibrated in $H_2O$ for 5 min before being activated in a mixture of 20 mM 1-ethyl-3-(3-dimethylaminopropyl)-carbodiimide) and 10 mM N-hydroxysuccinimide for 5 min. MiniFH was then loaded at 20 µg/mL in 10 mM sodium acetate, 100 mM NaCl pH 5.0 for 10 min before the sensors were quenched with 1 M ethanolamine for 5 min. The sensors were equilibrated in the assay buffer (PBS supplemented with 1 mg/mL BSA and 0.05% Tween 20) for 5 min. The association of either C3b (280 nM), FP (94 nM), D121 (714 nM), C3b+FP (280 nM and 94 nM, respectively), C3b+D121 (280 nM and 714 nM, respectively) and C3b+FP+D121 (280 nM, 94 nM and 714 nM, respectively) were assessed for 60 s followed by a 60 s dissociation step in assay buffer. The assay was repeated twice after regeneration of the sensors using PBS supplemented with 4 M of NaCl. The FP used for the assay was approximately 90% dimer and 10% trimer as judged by SEC analysis performed on a 24 mL Superdex200 Increase column.

EWE-hC3Nb1 was generated by cloning a glutamate, tryptophan, glutamate (EWE) motif into the N-terminal of hC3nb1 (Jensen et al., 2018) and purified as in example 1. IgG-Fc-hC3Nb1 was generated by fusing the hC3nb1 nanobody to the C-terminal of the hIgG1 insert in pFUSE-N (Invitrogen) using overlap extension PCR. HEK 293f cells were transfected with the plasmid in a DNA:polyethylenimine ratio of 1:2.5. The conditioned media was harvested 5 days after transfection. The pH of the media was adjusted by application of 20 mM Tris:HCl (pH 8.5) and the media was applied to Histrap Excel (GE Healthcare). The protein was eluted by imidazole, concentrated and applied to Superdex 200 increase (GE Healthcare) column. To analyze binding of IgG-Fc-hC3Nb1 and EWE-hC3Nb1 to C3 and C3b, 140 µg C3b or native C3 was mixed 1:1 molar ratio to the IgG-Fc-hC3Nb1/EWE-hC3Nb1. The complex was incubated 5 min on ice, then applied to Superdex 200 increase (GE Healthcare) column equilibrated in 20 mM HEPES (pH 7.5), 150 mM NaCl for size exclusion chromatography.

AP and LP disposition assays were performed as described by Jensen et al., 2018.

Figure 3A:
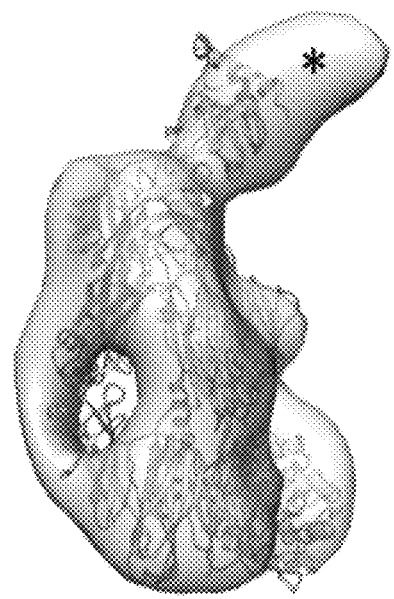
FIGS. 3A-3E.
Figure 3B:
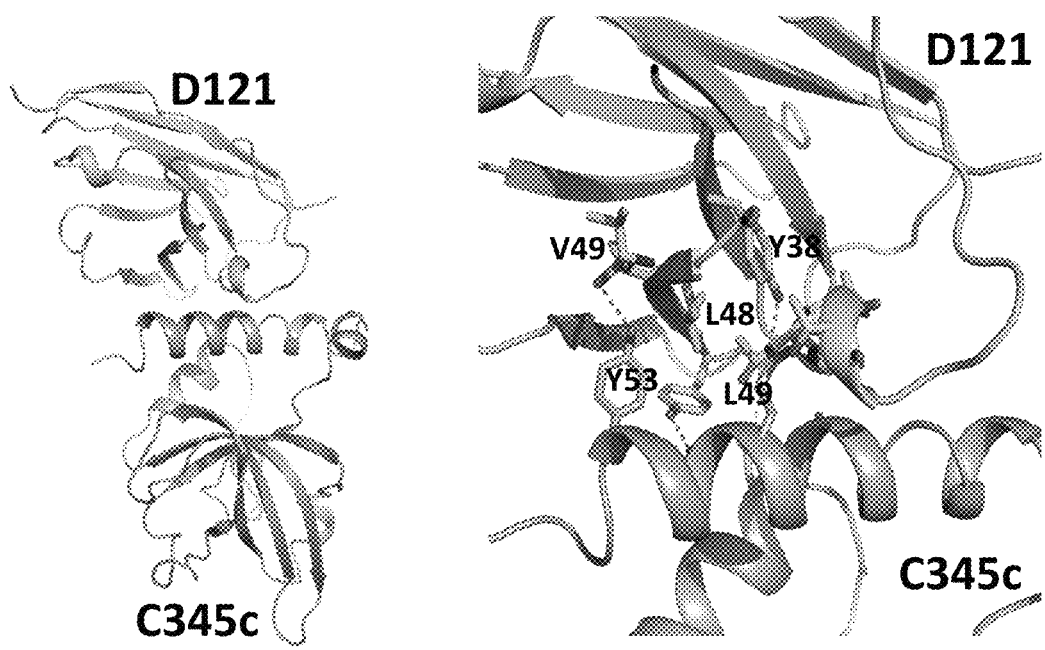
Figure 3C:
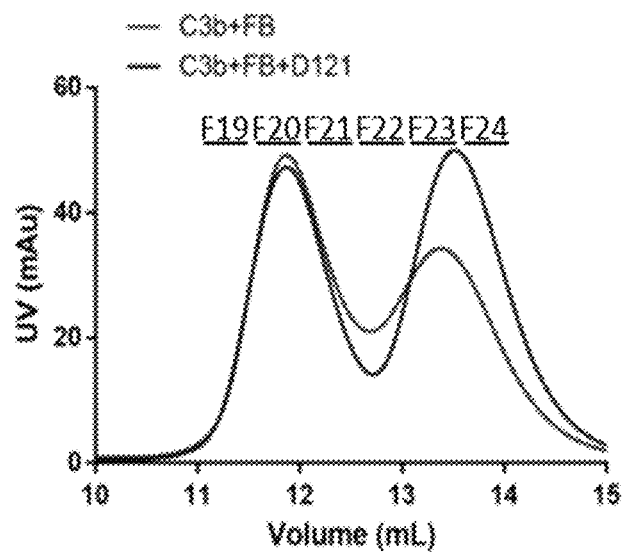
Figure 3D:
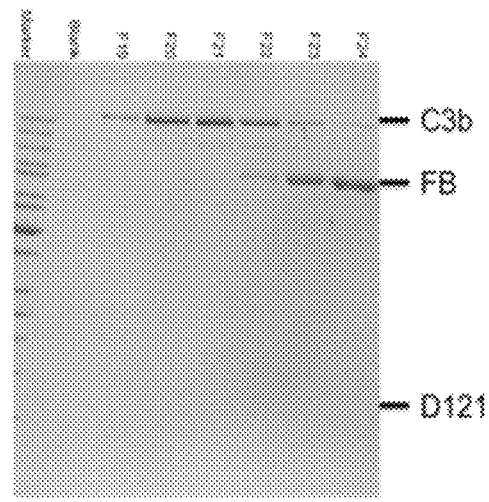
Figure 3E:
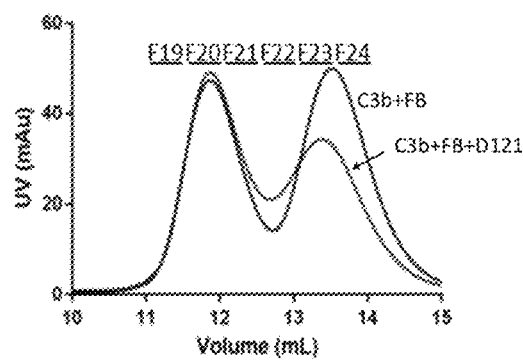

FIG. 3A shows that excess density corresponding to D121 (indicated by *) is present at the C-terminal C345c domain of C3b suggesting that D121 binds the C345c domain. FIG. 3B shows the crystal structure of D121 bound to the C345c domain of C3, confirming that the epitope of D121 is in the C345c domain of C3. As demonstrated in FIG. 3C and FIG. 3D, D121 prevents assembly of the AP C3 proconvertase C3bFB in SEC.

Figure 23A:
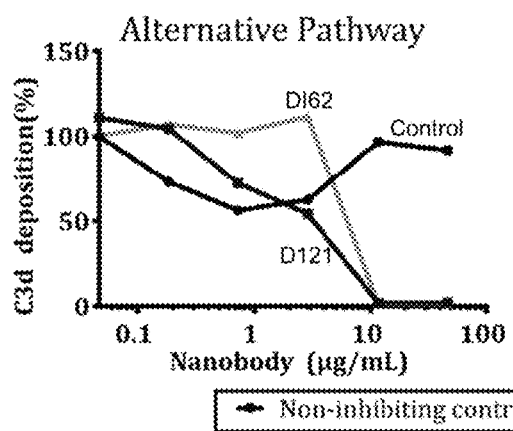
FIGS. 23A-23B. Effect of D121 and DI62 on C3d deposition in the alternative and classical pathways.
Figure 23B:
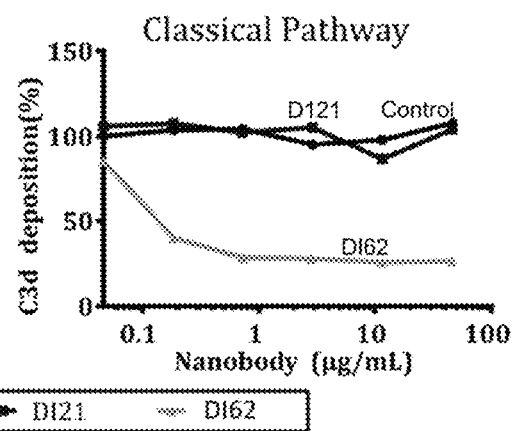
Figure 24:
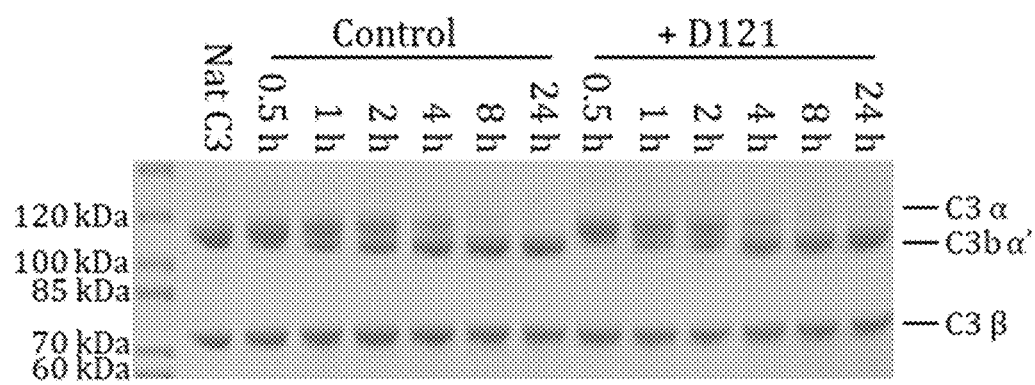
FIG. 24. CVF-Bb mediated cleavage of native C3. Cleavage of C3 into C3b in the presence or absence of D121. D121 does not inhibit the cleavage of C3 into C3b (generation of C3b alpha' chain).
Figure 25:
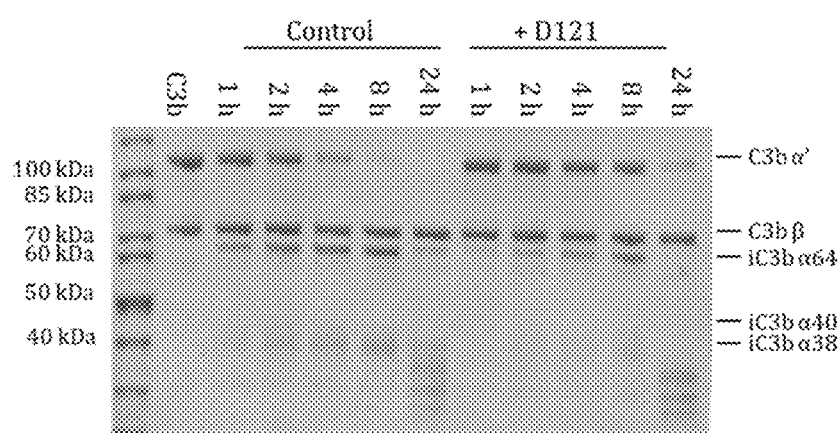
FIG. 25. FI mediate C3b cleavage assay. Cleavage of C3b by FI in the presence or absence of D121. D121 inhibits FI mediated C3b cleavage.
Figure 26:
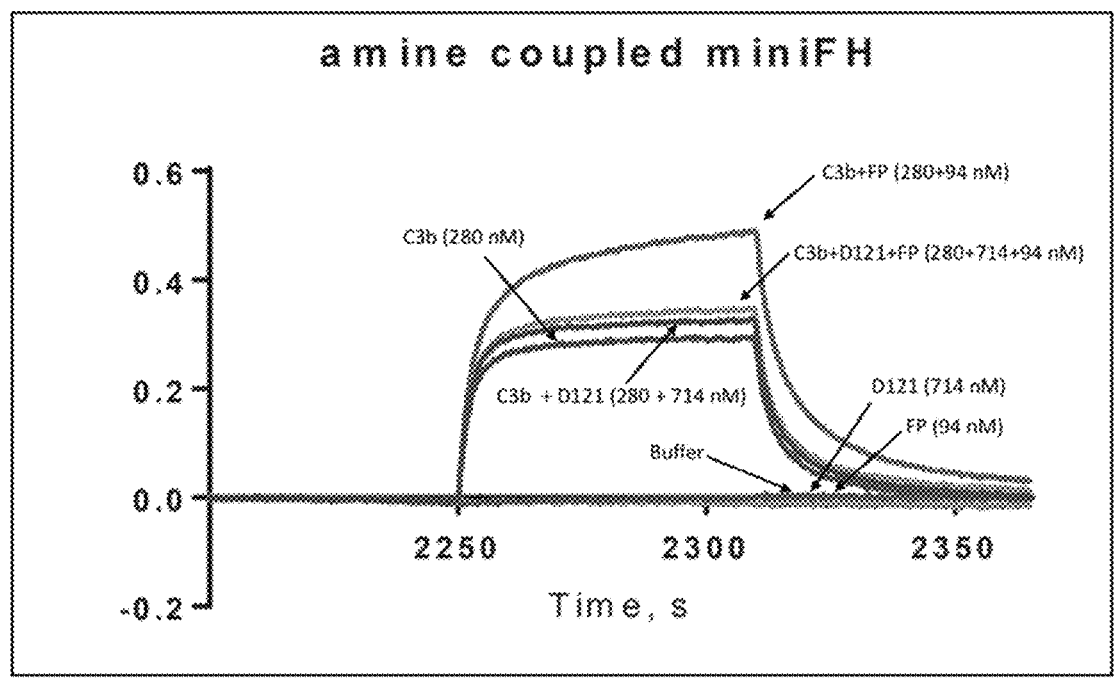
FIG. 26. BLI competition experiment with between D121, mini-FH and FP for binding to C3b. D121 inhibits binding of hFP but not mini-FH to hC3b.

D121 was tested for competition with human properdin (hFP) and human mini-FH for binding to human C3b (hC3b) using BLI. As shown in FIG. 26, D121 inhibits binding of hFP but not mini-FH to hC3b. FIG. 24 shows that D121 does not inhibit the cleavage of C3 into C3b by the CVF-Bb convertase. As shown in FIG. 25, D121 inhibits FI mediated C3b cleavage in the presence of factor H. D121 inhibits the alternative pathway (as assayed by C3d deposition) in a concentration dependent manner (FIG. 23A) but not the classical pathway (FIG. 23B), DI62 do not prevent binding of C3b to FB and assembly of the AP C3 proconvertase C3bFB in SEC as demonstrated in FIG. 4A. FIGS. 4B and 4C shows that DI62 inhibits activation of the AP in a dose dependent manner using human and mouse serum. DI62 also inhibits activation of the LP using human serum as demonstrated in FIG. 4D and activation of the LP using human serum as shown in FIG. 4E.

Figure 27:
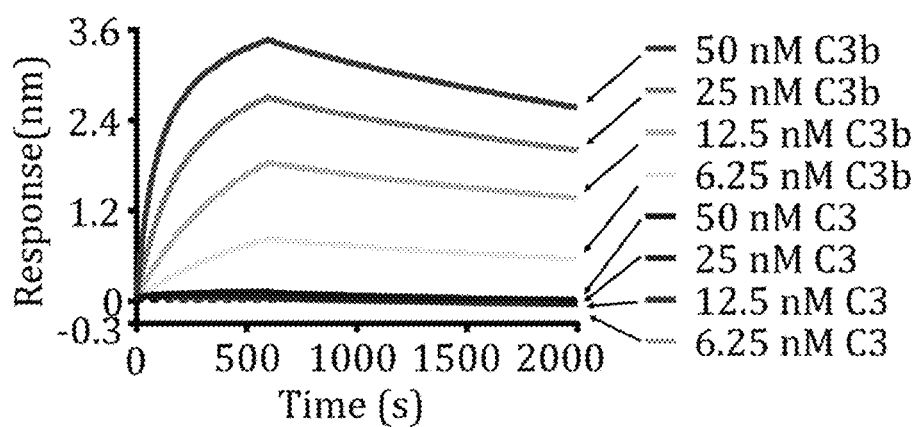
FIG. 27. BLI measurements of the interaction between EWE-hC3nb1, C3 and C3b. EWE-hC3nb1 binds to hC3b but not hC3.

FIG. 5 shows that EWE-hC3bNb1 is specific for C3b as it binds C3b but not C3 in SEC. Binding of EWE-hC3nb1 to hC3b, but not to hC3, was also demonstrated by BLI as shown in FIG. 27. FIG. 6 demonstrates that IgG-Fc-hC3bNb1 is specific for C3b as it binds C3b but not C3 in SEC. EWE-hC3bNb1 and IgG-Fc-hC3bNb1 both inhibits activation of the AP as shown in a C3 deposition assay (FIG. 7A) and in an erythrocyte lysis assay (FIG. 7B).

Figure 28:
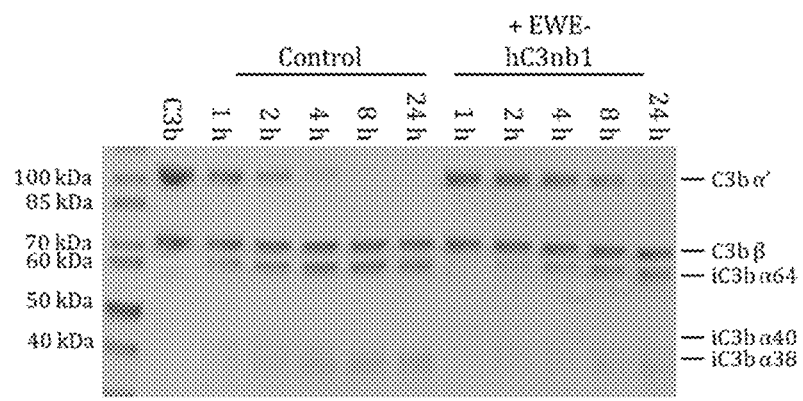
FIG. 28. FI mediate C3b cleavage assay. Cleavage of C3b by FI in the presence or absence of EWE-hC3nb1. EWE-hC3nb1 inhibit FI mediated C3b cleavage.
Figure 29:
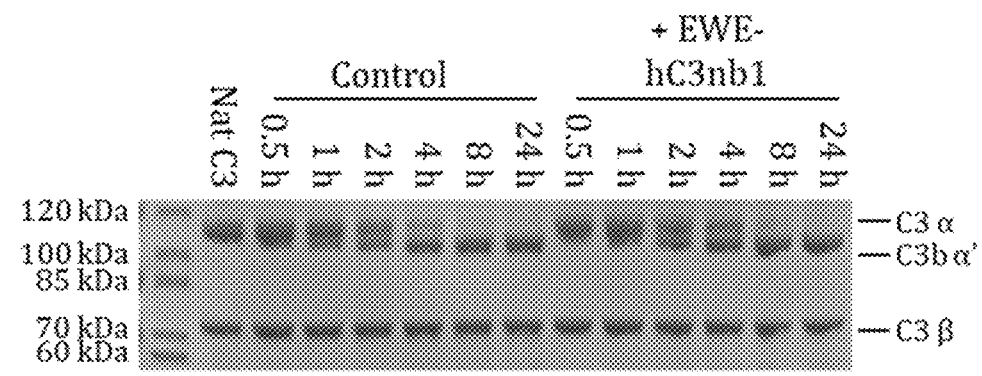
FIG. 29. CVF-Bb mediated cleavage of native C3. Cleavage of C3 into C3b in the presence or absence of EWE-hC3nb1. EWE-hC3nb1 does not inhibit the cleavage of C3 into C3b.

EWE-hC3nb1 was tested for its ability to inhibit cleavage of C3b by factor I (FI) in the presence of factor H (FH) (FIG. 28). As shown in FIG. 28, EWE-hC3nb1 inhibits FI mediated C3b cleavage. EWE-hC3nb1 was tested to assay the inhibitory activity on C3 cleavage by the CVF-Bb convertase (FIG. 29). As shown in FIG. 29, EWE-hC3nb1 does not inhibit the cleavage of C3 into C3b by the CVF-Bb convertase.

Figure 20:
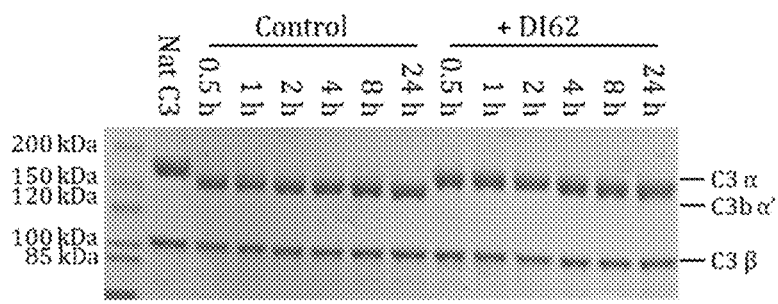
FIG. 20. CVF-Bb cleavage assay. Cleavage of C3 into C3b in the presence or absence of DI62. DI62 inhibits the cleavage of C3 into C3b (generation of C3b alpha' chain) while the C3 is rapidly cleaved in the absence of the nanobody.
Figure 21:
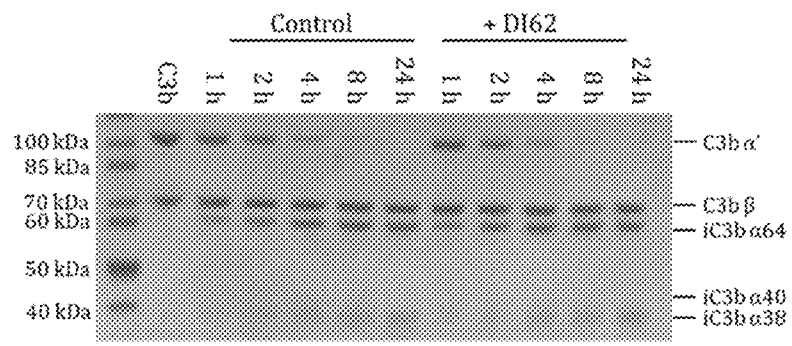
FIG. 21. FI mediate C3b cleavage assay. Cleavage of C3b by FI in the presence or absence of DI62. As shown, DI62 does not inhibit FI mediated C3b cleavage.

FIG. 20 shows that DI62 inhibits the cleavage of C3 into C3b by the CVF-Bb convertase while the C3 is rapidly cleaved in the absence of the nanobody. FIG. 21 shows that DI62 does not inhibit FI mediated C3b cleavage.

Figure 22:
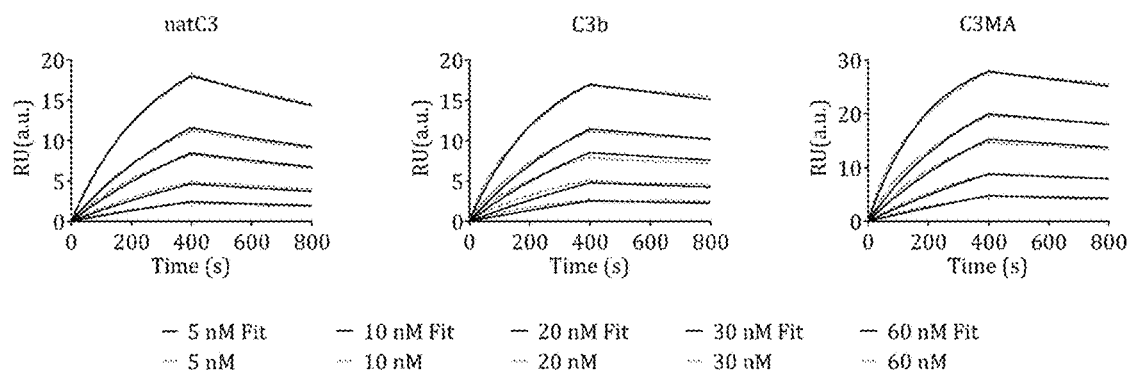
FIG. 22. Surface Plasmon Resonance measurements of the interaction between DI62 and native C3, C3b and C3MA. DI62 binds with high affinity to both native C3, C3b and C3MA.

DI62 binds with high affinity to both native C3, C3b and C3MA as shown in FIG. 22 and table 1.

Example 3

Generation of Inhibitory Nanobodies Specific for C4 and C4b.

Immunization and selection of nanobodies were performed essentially as described by Jensen et al., 2018 but using human C4 and human C4b. Nanobodies were expressed and purified as described in Example 1. C4 was purified from outdated human plasma. 300 mL of plasma were quickly thawed under tap water and 10 mM BZA, 3 µg/mL pancreatic trypsin inhibitor (PTI) and 1 mM PSMF were immediately added while stirring on ice. All the following purification steps were carried out either on ice or at 4° C. 60 mM BaCl2 and 25 mM trisodium citrate were dripped into the plasma while stirring and the precipitate was collected by centrifugation at 6000 rpm for 20 minutes. The supernatant was gaze filtered and loaded on a Q Sepharose FF 200 mL column equilibrated in 10 mM Tris-HCl, 100 mM NaCl, 50 mM EACA (5-amino caproic acid), 5 mM EDTA, 1 mM BZA and 0.5 mM PMSF, pH=7.5. The column was washed until baseline and eluted with a 1200 mL linear gradient from 100 to 600 mM NaCl at 20 mL/min flow rate. The fractions containing C4 were pooled and precipitated by slowly adding 12% w/w PEG6000 while stirring. After precipitation, the precipitate was collected at 4000 g for 30 minutes. The precipitate was resuspended in 100 mL 20 mM Tris-HCl, 200 mM NaCl, 1 mM BZA, 0.5 mM PMSF pH=7.5 (buffer 1A) and the resulting sample was filtered through 0.45 µm filters and applied to a Q Sepharose HP 50 mL column. The column was washed with buffer until baseline and eluted with a 600 mL linear gradient from 200 to 800 mM NaCl at 2 mL/min flow rate, while collecting 4 mL fractions. The fractions containing C4 were pooled and diluted three times with milliQ water. The sample was loaded on a Source15 Q 9 mL column equilibrated in 20 mM Tris-HCl, 200 mM NaCl, 100 UM BZA, 100 µM PMSF, pH=7.5 (buffer 2A). The column was washed until baseline with buffer and eluted with a 100 mL linear gradient from 200 to 400 mM NaCl at 1.5 mL/min flow rate. For C4b generation, C4 was diluted two times in milliQ water and loaded on a 9 mL MonoQ column equilibrated in 50 mM Tris, 200 mM NaCl pH=7.5 (buffer A). The column was washed with buffer A containing 300 mM NaCl and eluted with a 100 mL linear gradient from 300 to 600 mM NaCl at 1.5 mL/min flow rate. The fractions containing C4 were pooled, the concentration was measured and to generate C4b, the sample was supplemented with freshly made 10 mM iodoacetamide (IAA), 50 mM Tris-HCl PH=8.8, 30 mM glycine, followed by incubation with a 0.1% w/w ratio of C1s enzyme (Complement Technologies) for 12 hours at 37° C. To stop the reaction, the sample was added a 1% w/w ratio C1INH:C4 and incubated on ice for 1 hour. The generated C4b was repurified on a Source15 Q 9 mL column equilibrated in 20 mM HEPES, 200 mM NaCl PH=7.5. Elution was performed with an 80 mL linear gradient from 200 to 600 mM NaCl at 1.5 mL/min flow rate.

To crystallize C4b in complex with hC4Nb8, deglycosylated C4b was mixed in a 1:5 w/w ratio with nanobody hC4Nb8. The complex was purified by gel filtration on a Superdex200 increase column (GE Healthcare) equilibrated in 20 mM HEPES-NaOH, 150 mM NaCl, pH=7.5. The fractions containing the complex were concentrated to 8 mg/mL and used to set up crystallization trays where the drops contained 0.15 µL sample and 0.15 µL reservoir. Five days after dispensing the drops, plate crystals of the hC4b: hC4Nb8 complex appeared in 100 mM HEPES-NaOH pH=7, 10% w/w PEG4000, 10% v/v 2-propanol. The crystals were cryoprotected in 20% ethylene glycol for data collection. Datasets with highest resolution shell of 3.5 Å were collected at PETRA III P13 (EMBL Hamburg), at a wavelength of 0.98 Å and at 100 K. The diffraction data were processed using XDS (X-Ray Detector Software, Kabsch (2010)). C4b coordinates (PDB entry: 4XAM) without the C345c domain were used for initial structure determination by molecular replacement in Phenix (Adams, 2010).

pCEP4 plasmid encoding full length wild type C2 was purchased from Genscript and the stabilizing mutations Cys261Ala, Gln263Lys were introduced site using Quick-Change Lightning Site-Directed Mutagenesis Kit (Agilent Technologies) according to supplier's instructions. The DNA was purified using Qiagen Giga prep purification kit. DNA encoding C2 was transfected into HEK293f cells using a DNA:PEI (polyethyleneimine) ratio of 1:3. The conditioned medium was harvested 5 days after transfection and the pH was adjusted to 6.2 using 1 M NaOAc stock solution. The supernatant was supplemented with 0.5 mM PMSF, 1 mM BZA and 0.09% NaN3 and vacuum filtered through a 0.22 µm cellulose filter membrane prior to loading on an SP Sepharose FF 13 mL column, equilibrated in 50 mM NaOAc pH=6.2 (buffer A). All the purification steps were carried out at 4° C. The column was washed until baseline with buffer A and elution was performed with 100 mL linear gradient from 0 to 600 mM NaCl. The fractions containing C2 were concentrated and further purified by gel filtration on a Superdex 200 increase column (GE Healthcare) equilibrated in 20 mM HEPES, 150 mM NaCl pH=7.5. TRIFMA assay for CP was performed as described in Example 1.

To assay proconvertase formation in the presence of nanobodies, each nanobody was incubated with the proconvertase for 5 minutes at 4° C. at a C2:C4b:Nb 1.3:1:6 molar ratio and the sample was injected on a Superdex200 increase column (GE Healthcare) equilibrated in 20 mM HEPES-NaOH, 150 mM NaCl, 2 mM MgCl2 pH=7.5. Disruption of proconvertase formation was monitored by an increased OD (280 nm) intensity of the C4b (11.5 mL) and C2 (13 mL) peaks on the chromatograms.

Surface plasmon resonance measurements were conducted using a BIAcore T200 instrument (GE Healthcare). Streptavidin was diluted to 10 µg/mL in 10 mM sodium acetate pH=4.5 and immobilized to 100 RU on the carboxymethylated dextran surface of a CM5 sensor chip (GE Healthcare) using an amine coupling kit. The biotinylated nanobody was injected on the immobilized streptavidin at 30 µg/mL, giving 13 RU of captured nanobody. The binding measurements were performed in 20 mM HEPES, 150 mM NaCl, 3 mM MgCl2, 0.05% Tween 20 pH=7.5 at 30 µL/min flow rate. At the end of each concentration measurement the surface was regen-erated by injection of 100 mM glycine pH=2.7 for three cycles of 10 s contact time. Sensograms were recorded at concentrations 0.1, 5, 10, 25, 50 and 100 nM for C4, while at 0.1, 1, 5, 10, 25 nM for C4b. Fitting of the data was performed for all the measured concentrations simoultaneously, using BIAevaluation software (GE Healthcare). The apparent equilibrium dissociation constants (KD) were calculated from the ratio between the association and dissociation constants. The presented data are the mean±S.E. from two (C4b) or three (C4) separate experiments.

Figure 9C:
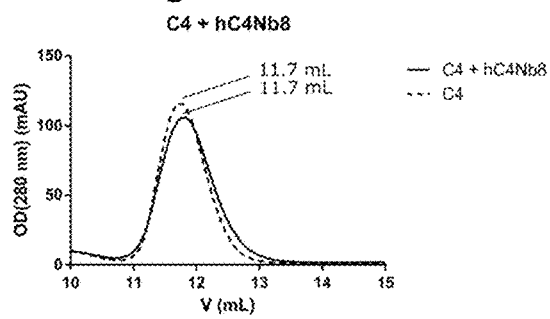
(FIG. 9C) SDS-PAGE analysis of the SEC analysis experiment between C4 and hC4Nb8 shown in panel (A) suggesting that hC4Nb8 binds weaker to C4 as compared to C4b since the nanobody is not apparent in the fractions containing C4.
Figure 9C:
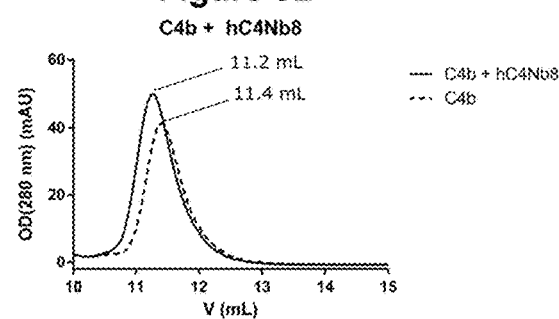
Figure 9C:
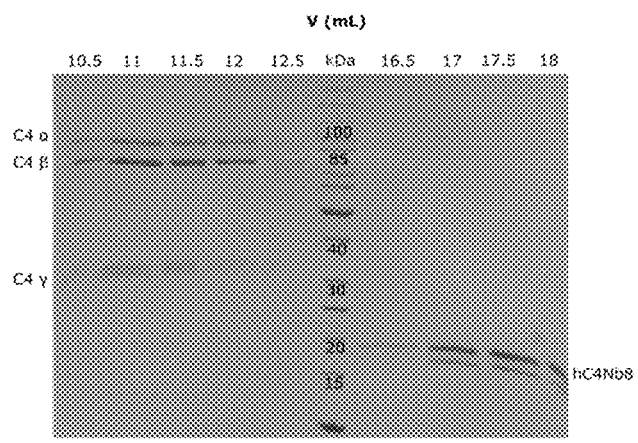
Figure 10A:
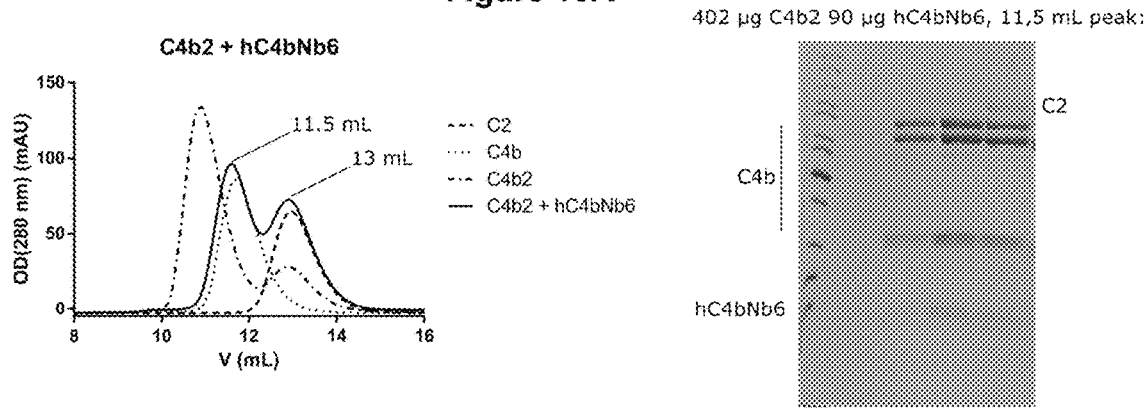
FIGS. 10A-10B.
Figure 10B:
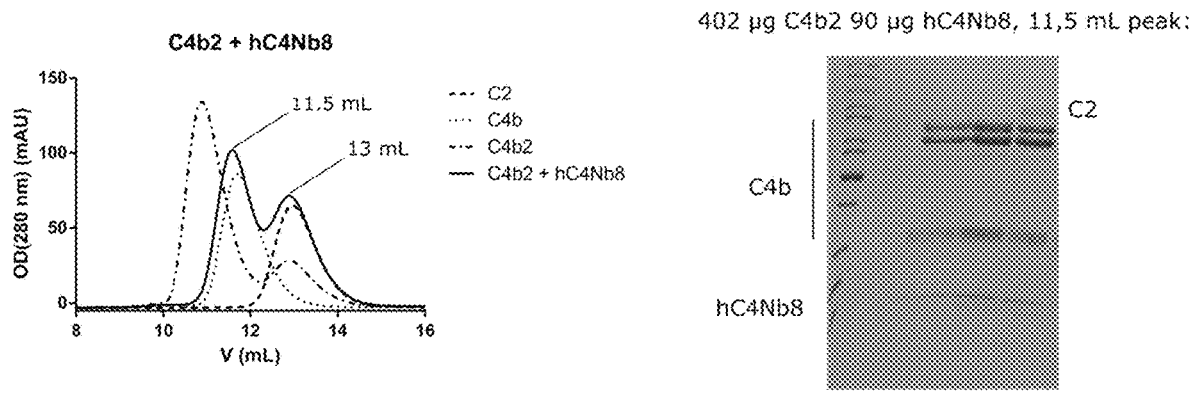
Figure 11A:
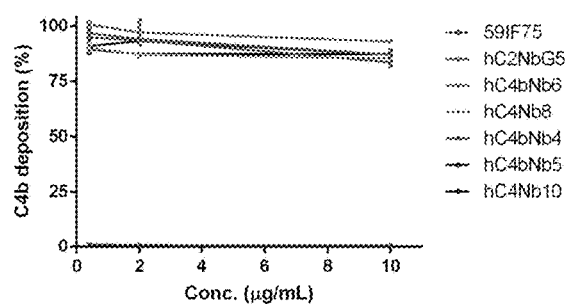
FIGS. 11A-11B.
Figure 11B:
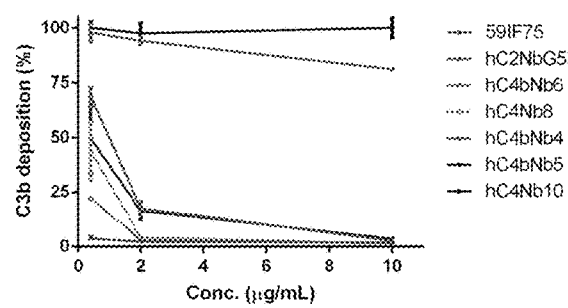

As demonstrated in FIGS. 8A and 8B hC4bNb6 binds to C4b and C4 in SEC. FIGS. 8C-8E shows that hC4bNb6 binds to C4 and C4b with high affinity as measured by SPR. FIG. 9 demonstrates that hC4Nb8 binds to C4b and C4 in SEC. hC4bNb6 and hC4Nb8 prevents formation of the CP C3 proconvertase C4b2 as evident from FIG. 10. hC4bNb6, hC4Nb8, hC4Nb4, hC4Nb5 and hC4Nb10 do not inhibit C4b deposition in a CP activation assay (FIG. 11A) but do inhibit C3b deposition in a dose dependent manner in a CP activation assay (FIG. 11B).

Figure 30:
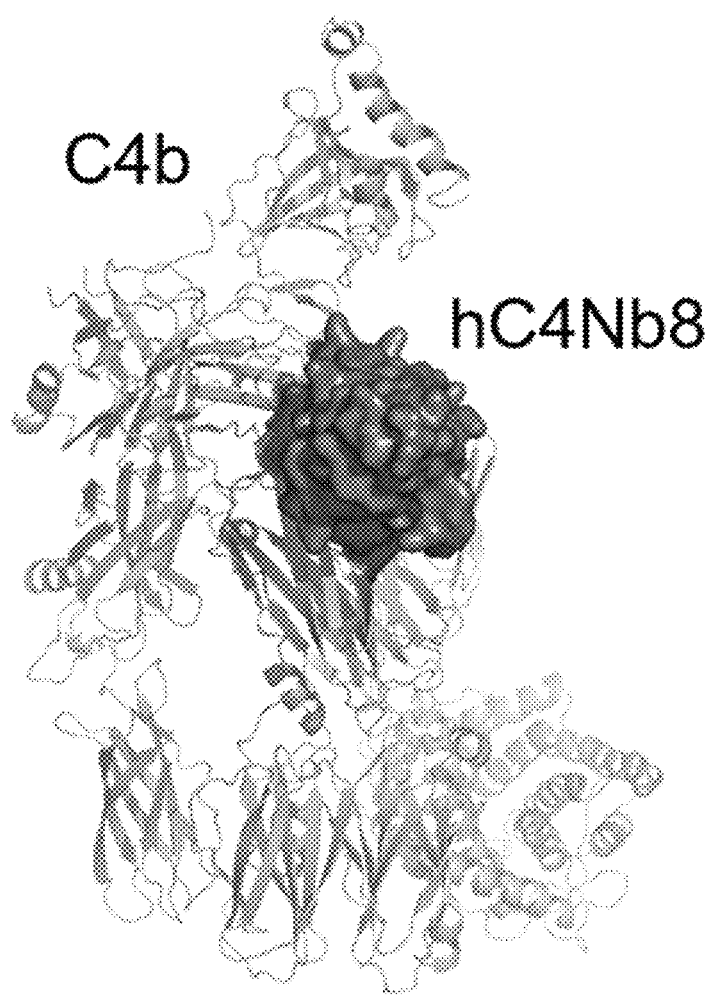
FIG. 30. Structure of human C4b in complex with hC4nb8. C4b is shown in cartoon representation and hC4Nb8 in surface representation. hC4Nb8 interacts with the MG6 domain and the α'NT region of C4b.
Figure 31:
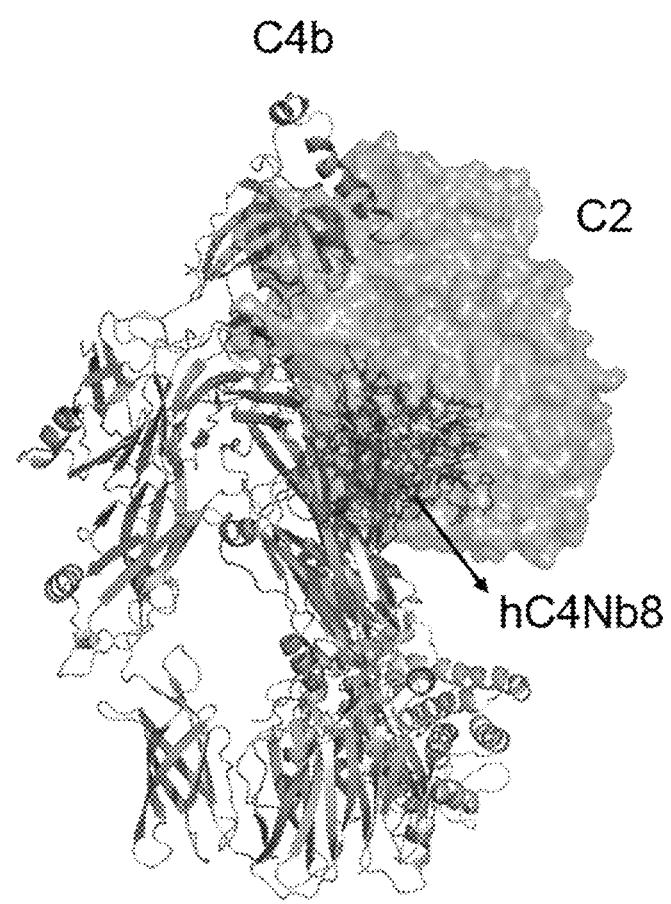
FIG. 31. Superposition of the structure of C4b-hC4nb8 and a model of C4bC2. C4b is shown in cartoon, C2 in surface and line representations. The structure shows that hC4nb8 and C2 cannot bind to C4b simultaneously and thus explains how hC4nb8 prevents assembly of the classical pathway C3 and C5 pro-convertases.

FIG. 30 shows the crystal structure of hC4nb8 in complex with hC4b. hC4bNb8 interacts with the MG6 domain and the α'NT region of C4b. FIG. 31 shows a superposition of the structure of C4b-hC4nb8 and a model of C4bC2. As evident from the figure hC4nb8 clashes C2 and thus inhibit assembly of the classical pathway C3 and C5 pro-convertases.

Figure 14:
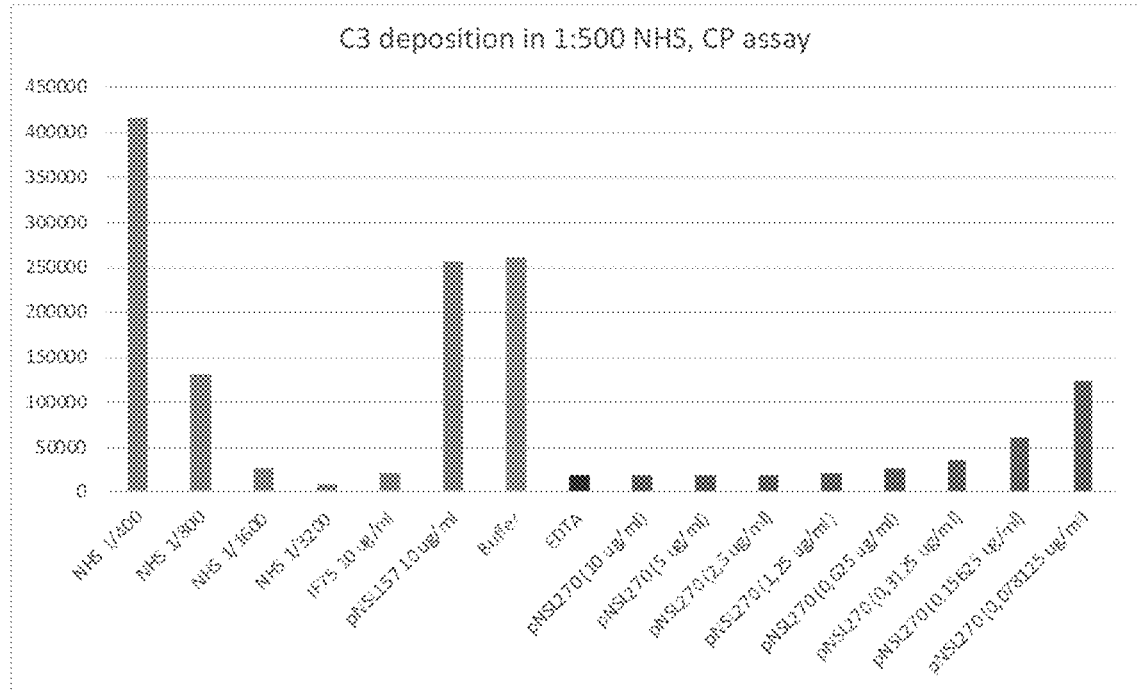
FIG. 14. Inhibitory action of pNSL270 on deposition of C3b in a CP activation assay on a surface of deposited IgG. IF75 is C1q inhibitor described above and pNSL157 is a control nanobody. As shown pNSL270 inhibits C3 deposition, and thus C3 cleavage, in a dose dependent manner upon activation of the classical pathway.
Figure 15:
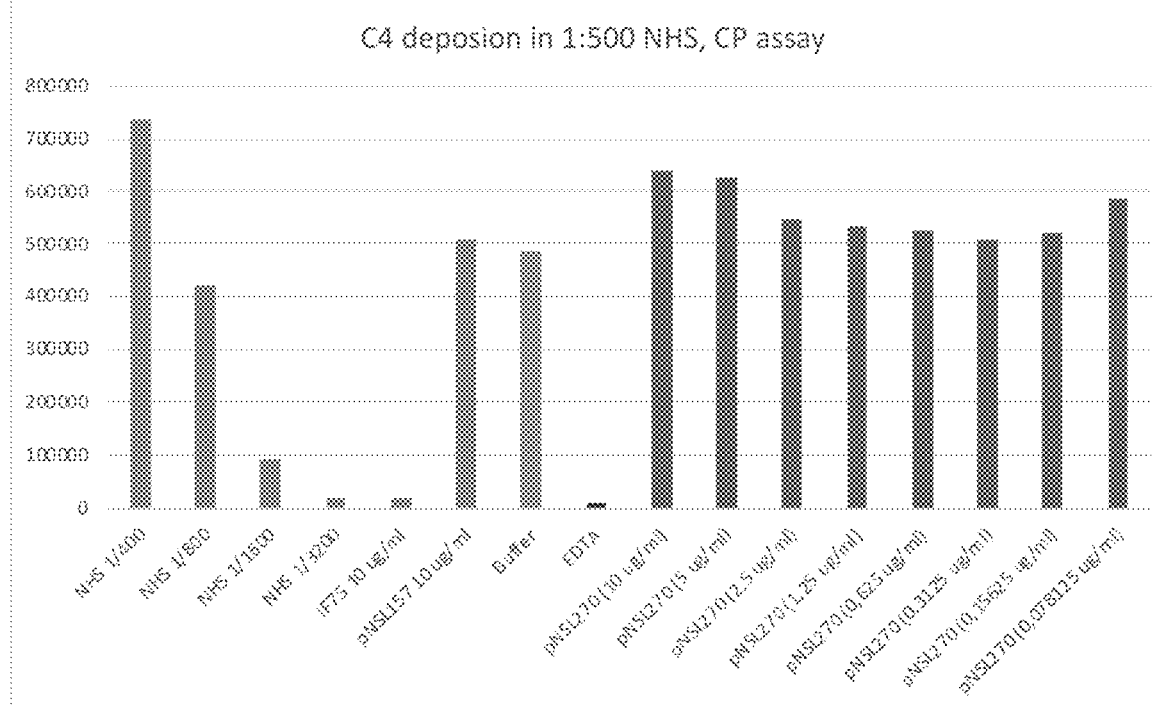
FIG. 15. Inhibitory action of pNSL270 on deposition of C4b in a CP activation assay on a surface of deposited IgG. IF75 is C1q inhibitor described above and pNSL157 is a control nanobody. As shown pNSL270 does not inhibit C4b deposition and thus C4 cleavage.
Figure 16:
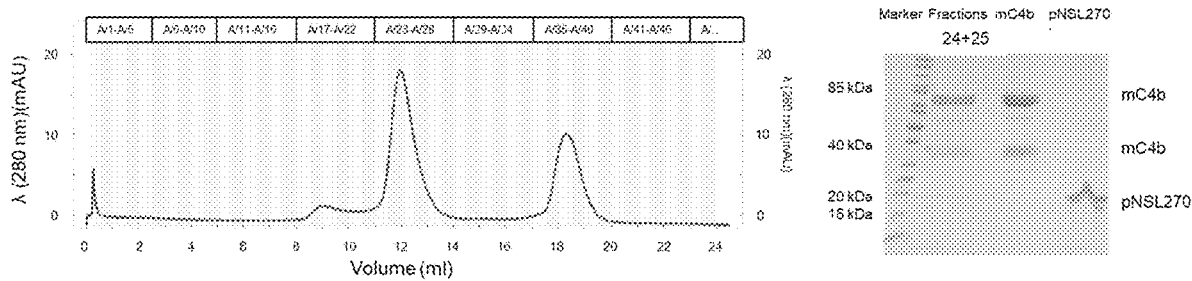
FIG. 16. SEC of the complex between mouse C4b (mC4b) and pNSL270 on a Superdex 200 Increase 10/300 column (left). SDS-PAGE of peak fractions 24+25 from run and pure mC4b and pNSL270 (right). As shown in the SDS-PAGE, pNSL270 binds to mouse C4b.

FIGS. 14 and 15 show classical pathway C3 and C4 deposition assays with normal human serum. As shown, pNSL270 inhibits C3 deposition (FIG. 14) in a dose dependent manner in a classical pathway assay but not C4 deposition (FIG. 15). Thus, pNSL270 prevents human C3 cleavage but not human C4 cleavage upon activation of the classical pathway. As demonstrated in FIG. 16 pNSL270 binds to mouse C4b in SEC.

Example 4

Bispecific C1q Nanobodies Activates Complement on Cancer Cells.

The genes for nanobodies 7D12, 9G8 and MU1053 were purchased from Genscript. For generation of bispecific nanobodies 7D12, 9G8 and MU1053 were genetically fused to C1q nanobodies using a 10 amino acid linker (GGGGSGGGGS) and expressed and purified as described above, Constructs are shown in FIG. 12A. A431, MDA-MB-468 and Raji cells were cultured in RPMI at 37° C. with 8% CO2. A1207 cells were cultured in DMEM at 37° C. with 8% CO2. All cells were supplemented with 10% fetal bovine serum and 0.1 mg/ml Penicillin-Streptomycin. Cells were detached by incubation with Accutase® (Sigma Aldrich) for 10 min at 37° C. Cells were harvested, washed 2 times in PBS and resuspended in veronal buffer saline (VBS). 1.0-0.5×106 cells were incubated with or without Nbs and 10% NHS (final concentration) for 1 h at 37° C. Following cells were centrifuged at 300 g for 5 min and washed 2 times in 800 µl PBA (PBS containing 1% w/v BSA). Cells were resuspended in 100 µl PBA added 100 µl mouse anti C3c (diluted 1:100) or mouse anti C1q (diluted 1:100) and incubated for 1 h on ice. Cells were centrifuged and washed two times in 800 µl PBA, added 100 µl anti mouse-FITC (diluted 1:100) and incubated for 1 h on ice. Cells were centrifuged and washed two times in 800 µl PBA and resuspended in 200 µl PBA. Ten minutes prior to flow cytometry cells were added DAPI. Flow cytometry was performed using a NovoCyte flow cytometer. Cells used for analysis were gated as single cells and live cells. Data were analyzed with FCS express.

Incubation of BiCE161 (anti-C1q fused to anti-CD38) with 10% human serum and Raji cells, which expresses CD38, results in recruitment of C1q (FIG. 12B, left) and complement activation as shown by deposition of C3 on cells (FIG. 12B, right).

Addition of DH38 and DH38 to MDA-MB-468 cells expressing EGFR results in little C3 deposition when incubated with 10% human serum. Addition of IA74 results in a medium amount of deposited C3, while addition of DF85 results in a high amount of C3 deposition (FIG. 12C).

DF85 is able to recruit C1q from human serum to different tumor cell lines that expresses EGFR (FIG. 13A). C1q recruitment results in complement activation and C3 deposition on cells (FIG. 13B). Incubation with BiCE128 results in similar C1q recruitment and C3 deposition as incubation with DF85 (FIGS. 13C and 13D).

REFERENCES

Afonine P V, Grosse-Kunstleve R W, Echols N, Headd J J, Moriarty N W, Mustyakimov M, Terwilliger T C, Urzhumtsev A, Zwart P H, Adams P D. Towards automated crystallographic structure refinement with phenix.refine. Acta Crystallogr D Biol Crystallogr. 2012 April; 68(Pt 4):352-67.

Emsley P, Lohkamp B, Scott W G, Cowtan K. Features and development of Coot. Acta Crystallogr D Biol Crystallogr. 2010 April; 66(Pt 4):486-501.

Jensen R K, Pihl R, Gadeberg T A F, Jensen J K, Andersen K R, Thiel S, Laursen N S, Andersen G R. A potent complement factor C3-specific nanobody inhibiting multiple functions in the alternative pathway of human and murine complement. J Biol Chem. 2018 Apr. 27; 293(17): 6269-6281.

Kabsch, W. (2010) Integration, scaling, space-group assignment and post-refinement. Acta Crystallogr. D Biol. Crystallogr. 66, 133-144.

McCoy A J, Grosse-Kunstleve R W, Adams P D, Winn M D, Storoni L C, Read R J. Phaser crystallographic software. J Appl Crystallogr. 2007 Aug. 1; 40(Pt 4):658-674. Epub 2007 Jul. 13.

Moreau C, Bally I, Chouquet A, Bottazzi B, Ghebrehiwet B, Gaboriaud C, Thielens N. Structural and Functional Characterization of a Single-Chain Form of the Recognition Domain of Complement Protein C1q. Front Immunol. 2016 Mar. 2; 7:79. doi: 10.3389/fimmu.2016.00079.

Scheres S H. RELION: implementation of a Bayesian approach to cryo-EM structure determination. J Struct Biol. 2012 December; 180(3):519-30

Suloway, C., Pulokas, J., Fellmann, D., Cheng, A., Guerra, F., Quispe, J., Stagg, S., Potter, C. S., and Carragher, B. (2005) Automated molecular microscopy: the new Leginon system. J. Struct. Biol. 151, 41-60.

Tenner A J, Lesavre P H, Cooper N R. Purification and radiolabeling of human C1q. J Immunol. 1981 August; 127(2):648-53.

Voss, N. R., Yoshioka, C. K., Radermacher, M., Potter, C. S., and Carragher, B. (2009) DoG Picker and TiltPicker: software tools to facilitate particle selection in single particle electron microscopy. J. Struct. Biol. 166, 205-213.

Sequences

Where relevant, the UniProt reference is provided for specific reference to the respective sequences. It is understood that the present disclosure relates to all variants disclosed in relation to the specific UniProt reference.

```
Human C3 UniProtKB - P01024 (CO3_HUMAN) residues 23-1663
                                                              SEQ ID NO: 1
SPMYSIITPNILRLESEETMVLEAHDAQGDVPVTVTVHDFPGKKLVLSSEKTVLTPATN
HMGNVTFTIPANREFKSEKGRNKFVTVQATFGTQVVEKVVLVSLQSGYLFIQTDKTIYT
PGSTVLYRIFTVNHKLLPVGRTVMVNIENPEGIPVKQDSLSSQNQLGVLPLSWDIPELV
NMGQWKIRAYYENSPQQVFSTEFEVKEYVLPSFEVIVEPTEKFYYIYNEKGLEVTITAR
FLYGKKVEGTAFVIFGIQDGEQRISLPESLKRIPIEDGSGEVVLSRKVLLDGVQNPRAE
DLVGKSLYVSATVILHSGSDMVQAERSGIPIVTSPYQIHFTKTPKYFKPGMPFDLMVFV
TNPDGSPAYRVPVAVQGEDTVQSLTQGDGVAKLSINTHPSQKPLSITVRTKKQELSEA
EQATRTMQALPYSTVGNSNNYLHLSVLRTELRPGETLNVNFLLRMDRAHEAKIRYYTY
LIMNKGRLLKAGRQVREPGQDLVVLPLSITTDFIPSFRLVAYYTLIGASGQREVVADSV
WVDVKDSCVGSLVVKSGQSEDRQPVPGQQMTLKIEGDHGARVVLVAVDKGVFVLNK
KNKLTQSKIWDVVEKADIGCTPGSGKDYAGVFSDAGLTFTSSSGQQTAQRAELQCPQ
PAARRRRSVQLTEKRMDKVGKYPKELRKCCEDGMRENPMRFSCQRRTRFISLGEAC
KKVFLDCCNYITELRRQHARASHLGLARSNLDEDIIAEENIVSRSEFPESWLWNVEDLK
EPPKNGISTKLMNIFLKDSITTWEILAVSMSDKKGICVADPFEVTVMQDFFIDLRLPYSV
VRNEQVEIRAVLYNYRQNQELKVRVELLHNPAFCSLATTKRRHQQTVTIPPKSSLSVP
YVIVPLKTGLQEVEVKAAVYHHFISDGVRKSLKVVPEGIRMNKTVAVRTLDPERLGRE
GVQKEDIPPADLSDQVPDTESETRILLQGTPVAQMTEDAVDAERLKHLIVTPSGCGEQ
NMIGMTPTVIAVHYLDETEQWEKFGLEKRQGALELIKKGYTQQLAFRQPSSAFAAFVK
RAPSTWLTAYVVKVFSLAVNLIAIDSQVLCGAVKWLILEKQKPDGVFQEDAPVIHQEMI
GGLRNNNEKDMALTAFVLISLQEAKDICEEQVNSLPGSITKAGDFLEANYMNLQRSYT
VAIAGYALAQMGRLKGPLLNKFLTTAKDKNRWEDPGKQLYNVEATSYALLALLQLKDF
DFVPPVVRWLNEQRYYGGGYGSTQATFMVFQALAQYQKDAPDHQELNLDVSLQLPS
RSSKITHRIHWESASLLRSEETKENEGFTVTAEGKGQGTLSVVTMYHAKAKDQLTCN
KFDLKVTIKPAPETEKRPQDAKNTMILEICTRYRGDQDATMSILDISMMTGFAPDTDDL
KQLANGVDRYISKYELDKAFSDRNTLIIYLDKVSHSEDDCLAFKVHQYFNVELIQPGAV
KVYAYYNLEESCTRFYHPEKEDGKLNKLCRDELCRCAEENCFIQKSDDKVTLEERLDK
ACEPGVDYVYKTRLVKVQLSNDFDEYIMAIEQTIKSGSDEVQVGQQRTFISPIKCREAL
KLEEKKHYLMWGLSSDFWGEKPNLSYIIGKDTWVEHWPEEDECQDEENQKQCQDL
GAFTESMVVFGCPN Mouse C3 UniProtKB - P01027 (CO3_MOUSE) residues 25-1663
                                                              SEQ ID NO: 2
IPMYSIITPNVLRLESEETIVLEAHDAQGDIPVTVTVQDFLKRQVLTSEKTVLTGASGHL
RSVSIKIPASKEFNSDKEGHKYVTVVANFGETVVEKAVMVSFQSGYLFIQTDKTIYTPG
STVLYRIFTVDNNLLPVGKTVVILIETPDGIPVKRDILSSNNQHGILPLSWNIPELVNMGQ
WKIRAFYEHAPKQIFSAEFEVKEYVLPSFEVRVEPTETFYYIDDPNGLEVSIIAKFLYGK
NVDGTAFVIFGVQDGDKKISLAHSLTRVVIEDGVGDAVLTRKVLMEGVRPSNADALVG
KSLYVSVTVILHSGSDMVEAERSGIPIVTSPYQIHFTKTPKFFKPAMPFDLMVFVTNPD
GSPASKVLVVTQGSNAKALTQDDGVAKLSINTPNSRQPLTITVRTKKDTLPESRQATK
TMEAHPYSTMHNSNNYLHLSVSRMELKPGDNLNVNFHLRTDPGHEAKIRYYTYLVMN
KGKLLKAGRQVREPGQDLVVLSLPITPEFIPSFRLVAYYTLIGASGQREVVADSVWVD
VKDSCIGTLVVKGDPRDNHLAPGQQTTLRIEGNQGARVGLVAVDKGVFVLNKKNKLT
QSKIWDVVEKADIGCTPGSGKNYAGVFMDAGLAFKTSQGLQTEQRADLECTKPAASV
QLMERRMDKAGQYTDKGLRKCCEDGMRDIPMRYSCQRRARLITQGENCIKAFIDCC
NHITKLREQHRRDHVLGLARSELEEDIISRSHFPQSWLWTIEELKEPEKNGIST
KVMNIFLKDSITTWEILAVSLSDKKGICVADPYEIRVMQDFFIDLRLPYSVVRNEQVEIR
AVLFNYREQEELKVRVELLHNPAFCSMATAKNRYFQTIKIPPKSSVAVPYVIVPLKIGQ
QEVEVKAAVFNHFISDGVKKTLKVVPEGMRINKTVAIHTLDPEKLGQGGVQKVDVPAA
DLSDQVPDTDSETRIILQGSPVVQMAEDAVDGERLKHLIVTPAGCGEQNMIGMTPTVI
AVHYLDQTEQWEKFGIEKRQEALELIKKGYTQQLAFKQPSSAYAAFNNRPPSTWLTA
```

-continued

```
YVVKVFSLAANLIAIDSHVLCGAVKWLILEKQKPDGVFQEDGPVIHQEMIGGFRNAKEA
DVSLTAFVLIALQEARDICEGQVNSLPGSINKAGEYIEASYMNLQRPYTVAIAGYALAL
MNKLEEPYLGKFLNTAKDRNRWEEPDQQLYNVEATSYALLALLLLKDFDSVPPVVRW
LNEQRYYGGGYGSTQATFMVFQALAQYQTDVPDHKDLNMDVSFHLPSRSSATTFRL
LWENGNLLRSEETKQNEAFSLTAKGKGRGTLSVVAVYHAKLKSKVTCKKFDLRVSIRP
APETAKKPEEAKNTMFLEICTKYLGDVDATMSILDISMMTGFAPDTKDLELLASGVDRY
ISKYEMNKAFSNKNTLIIYLEKISHTEEDCLTFKVHQYFNVGLIQPGSVKVYSYYNLEES
CTRFYHPEKDDGMLSKLCHSEMCRCAEENCFMQQSQEKINLNVRLDKACEPGVDYV
YKTELTNIELLDDFDEYTMTIQQVIKSGSDEVQAGQQRKFISHIKCRNALKLQKGKKYL
MWGLSSDLWGEKPNTSYIIGKDTWVEHWPEAEECQDKYQKQCEELGAFTESMVV
YGCPN

Human C1q chain A UniProtKB - P02745 (C1QA_HUMAN) residues 23-245
                                                    SEQ ID NO: 3
EDLCRAPDGKKGEAGRPGRRGRPGLKGEQGEPGAPGIRTGIQGLKGDQGEPGPSG
NPGKVGYPGPSGPLGARGIPGIKGTKGSPGNIKDQPRPAFSAIRRNPPMGGNVVIFDT
VITNQEEPYQNHSGRFVCTVPGYYYFTFQVLSQWEICLSIVSSSRGQVRRSLGFCDTT
NKGLFQVVSGGMVLQLQQGDQVWVEKDPKKGHIYQGSEADSVFSGFLIFPSA Human C1q chain B UniProtKB - P02746 (C1QB_HUMAN) residues 28-253
                                                    SEQ ID NO: 4
QLSCTGPPAIPGIPGIPGTPGPDGQPGTPGIKGEKGLPGLAGDHGEFGEKGDPGIPGN
PGKVGPKGPMGPKGGPGAPGPKGESGDYKATQKIAFSATRTINVPLRRDQTIRF
DHVITNMNNNYEPRSGKFTCKVPGLYYFTYHASSRGNLCVNLMRGRERAQKVVTFC
DYAYNTFQVTTGGMVLKLEQGENVFLQATDKNSLLGMEGANSIFSGFLLFPDMEA Human C1q chain C UniProtKB - P02747 (C1QC_HUMAN) residues 29-245
                                                    SEQ ID NO: 5
NTGCYGIPGMPGLPGAPGKDGYDGLPGPKGEPGIPAIPGIRGPKGQKGEPGLPGHP
GKNGPMGPPGMPGVPGPMGIPGEPGEEGRYKQKFQSVFTVTRQTHQPPAPNSLIRF
NAVLTNPQGDYDTSTGKFTCKVPGLYYFVYHASHTANLCVLLYRSGVKVVTFCGHTS
KTNQVNSGGVLLRLQVGEEVWLAVNDYYDMVGIQGSDSVFSGFLLFPD Human C4A alpha chain UniProtKB - P0C0L4 (C04A_HUMAN) residues 680-1446
                                                    SEQ ID NO: 6
NVNFQKAINEKLGQYASPTAKRCCQDGVTRLPMMRSCEQRAARVQQPDCREPFLSC
CQFAESLRKKSRDKGQAGLQRALEILQEEDLIDEDDIPVRSFFPENWLWRVETVDRF
QILTLWLPDSLTTWEIHGLSLSKTKGLCVATPVQLRVFREFHLHLRLPMSVRRFEQLEL
RPVLYNYLDKNLTVSVHVSPVEGLCLAGGGGLAQQVLVPAGSARPVAFSVVPTAAAA
VSLKVVARGSFEFPVGDAVSKVLQIEKEGAIHREELVYELNPLDHRGRTLEIPGNSDP
NMIPDGDFNSYVRVTASDPLDTLGSEGALSPGGVASLLRLPRGCGEQTMIYLAPTLAA
SRYLDKTEQWSTLPPETKDHAVDLIQKGYMRIQQFRKADGSYAAWLSRDSSTWLTAF
VLKVLSLAQEQVGGSPEKLQETSNWLLSQQQADGSFQDPCPVLDRSMQGGLVGND
ETVALTAFVTIALHHGLAVFQDEGAEPLKQRVEASISKANSFLGEKASAGLLGAHAAAI
TAYALTLTKAPVDLLGVAHNNLMAMAQETGDNLYWGSVTGSQSNAVSPTPAPRNPS
DPMPQAPALWIETTAYALLHLLLHEGKAEMADQASAWLTRQGSFQGGFRSTQDTVIA
LDALSAYWIASHTTEERGLNVTLSSTGRNGFKSHALQLNNRQIRGLEEELQFSLGSKI
NVKVGGNSKGTLKVLRTYNVLDMKNTTCQDLQIEVTVKGHVEYTMEANEDYEDYEYD
ELPAKDDPDAPLQPVTPLQLFEG Human C4A beta chain UniProtKB - P0C0L4 (C04A_HUMAN) residues 20-675
                                                    SEQ ID NO: 7
KPRLLLFSPSVVHLGVPLSVGVQLQDVPRGQVVKGSVFLRNPSRNNVPCSPKVDFTL
SSERDFALLSLQVPLKDAKSCGLHQLLRGPEVQLVAHSPWLKDSLSRTTNIQGINLLF
SSRRGHLFLQTDQPIYNPGQRVRYRVFALDQKMRPSTDTITVMVENSHGLRVRKKEV
YMPSSIFQDDFVIPDISEPGTWKISARFSDGLESNSSTQFEVKKYVLPNFEVKITPGKP
YILTVPGHLDEMQLDIQARYIYGKPVQGVAYVRFGLLDEDGKKTFFRGLESQTKLVNG
QSHISLSKAEFQDALEKLNMGITDLQGLRLYVAAAIIESPGGEMEEAELTSWYFVSSPF
SLDLSKTKRHLVPGAPPLLQALVREMSGSPASGIPVKVSATVSSPGSVPEVQDIQQNT
DGSGQVSIPIIIPQTISELQLSVSAGSPHPAIARLTVAAPPSGGPGFLSIERPDSRPPRV
GDTLNLNLRAVGSGATFSHYYYMILSRGQIVFMNREPKRTLTSVSVFVDHHLAPSFYF
VAFYYHGDHPVANSLRVDVQAGACEGKLELSVDGAKQYRNGESVKLHLETDSLALVA
LGALDTALYAAGSKSHKPLNMGKVFEAMNSYDLGCGPGGGDSALQVFQAAGLAFSD
GDQWTLSRKRLSCPKEKTT Human C4A gamma chain UniProtKB - P0C0L4 (C04A_HUMAN) residues 1454-
1744
                                                    SEQ ID NO: 8
EAPKVVEEQESRVHYTVCIWRNGKVGLSGMAIADVTLLSGFHALRADLEKLTSLSDRY
VSHFETEGPHVLLYFDSVPTSRECVGFEAVQEVPVGLVQPASATLYDYYNPERRCSV
FYGAPSKSRLLATLCSAEVCQCAEGKCPRQRRALERGLQDEDGYRMKFACYYPRVE
YGFQVKVLREDSRAAFRLFETKITQVLHFTKDVKAAANQMRNFLVRASCRLRLEPGKE
YLIMGLDGATYDLEGHPQYLLDSNSWIEEMPSERLCRSTRQRAACAQLNDFLQEYGT
QGCQV EA57
                                                    SEQ ID NO: 9
QVQLVESGGGLVQPGGSLRLSCAASGFTLNQYAIGWFRQAPGKEREGVSCISNSDG
GLYYADSVKGRFTISRDNAKNTVYLQMNSLKPEDTAVYYCATDPGGPTMYGSRWCD
SRLFYSWGQGTQVTVSS
```

-continued

CDR1:  
GFTLNQYAIG  
SEQ ID NO: 10

CDR2:  
CISNSDGGLY  
SEQ ID NO: 11

CDR3:  
DPGGPTMYGSRWCDSRLFYS  
SEQ ID NO: 12

IF75  
QVQLVETGGGLVQAGGSLRLSCAASGRTFNNDVMAWFRQAPGTEREFVALITAGGG
THYADSVKGRFVISRDNDKNMAYLQMNSLKSEDTAIYYCGADENPPGWPSRWSSAY
DYWGQGTQVTVSS  
SEQ ID NO: 13

CDR1:  
GRTFNNDVMA  
SEQ ID NO: 14

CDR2:  
LITAGGGTH  
SEQ ID NO: 15

CDR3:  
DENPPGWPSRWSSAYDY  
SEQ ID NO: 16

IF78  
QVQLVESGGGLVQDGDSLRLSCAGSGWTFRDSMYNMGWFRQAPGKEREFVAAISW
RGGSTLYADSVKGRFTISRDNAKNTVYLQMNSLKPEDTAVYQCAADTSARAALYSTG
YEYDHWGQGTQVTVSS  
SEQ ID NO: 17

CDR1:  
GWTFRDSMYNMG  
SEQ ID NO: 18

CDR2:  
AISWRGGSTLY  
SEQ ID NO: 19

CDR3:  
DTSARAALYSTGYEYDH  
SEQ ID NO: 20

IH31  
QVQLVESGGGLVQAGGSLRLSCAASGRTSSDHITAWFRQAPGKEREFVASINWSGS
RAYYADSDKRRFTISRDNAKNTVSLQTNSLKPEDTAVYYCAVKFADISDAYYHHQTDY
DYWGQGTQVTVSS  
SEQ ID NO: 21

CDR1:  
GRTSSDHITA  
SEQ ID NO: 22

CDR2:  
SINWSGSRAY  
SEQ ID NO: 23

CDR3:  
KFADISDAYYHHQTDYDY  
SEQ ID NO: 24

IH33  
QVQLVETGGGLVQTGGSLRLSCAASGSTDSIAAIIWYRQTPENEREFVAGITSGVNTN
YAAPVKGRFTISRDNAKNTVYLQMNSLKPEDTGVYYCKAAVVMGPSTTDYWGQGTQ
VTVSS  
SEQ ID NO: 25

CDR1:  
GSTDSIAAII  
SEQ ID NO: 26

CDR2:  
GITSGVN  
SEQ ID NO: 27

CDR3:

AVVMGPSTTDY                                                SEQ ID NO: 28

IH35
                                                           SEQ ID NO: 29
QVQLVETGGGVAQAGGSLRLSCAASGFSFDDYAIGWLRQAPGKEREGVSCISAGDG
SPQYADSVKGRFTISSDNAKNTVYLQMNSLKPEDTAVYYCAVSRWSNCAWDYYGMD
PWGKGTLVTVSS

CDR1:
                                                           SEQ ID NO: 30
GFSFDDYAIG

CDR2:
                                                           SEQ ID NO: 31
CISAGDGSPQ

CDR3:
                                                           SEQ ID NO: 32
SRWSNCAWDYYGMDP

IH37
                                                           SEQ ID NO: 33
QVQLVESGGGLAQAGGSLRLSCQGSGRTFNNDVLAWFRQAPGKEREYVAMITSGG
NPFYADSVKGRFVISRDNDKNTVYLQMNSLKSEDTAIYYCAADENPPGWPSRWSSAY
DYWGQGTQVTVSS

CDR1:
                                                           SEQ ID NO: 34
GRTFNNDVLA

CDR2:
                                                           SEQ ID NO: 35
MITSGGNPF

CDR3:
                                                           SEQ ID NO: 36
DENPPGWPSRWSSAYDY

IH39
                                                           SEQ ID NO: 37
QVQLVESGGGLVQAGGSLRLSCVAYGVASVTTVMGWFRQSPGKEREFVAAIGPSGG
THYGDSAKGRFTISRDNAKNTVYLQMNSLKPEDTAVYDCAADLRGGGMWASSGRYE
YWGQGTQVTVSS

CDR1:
                                                           SEQ ID NO: 38
GVASVTTVMG

CDR2:
                                                           SEQ ID NO: 39
AIGPSGGTH

CDR3:
                                                           SEQ ID NO: 40
DLRGGGMWASSGRYEY hC4bNb6
                                                           SEQ ID NO: 41
QVQLVETGGGVVRAGGSLRLSCAASGRTLGRYSMAWFRQAPGKERQFVAAINWSG
GSTYYPDFAKDRFTISRDSAKNMVYLQMNSLKPEDTAVYYCAAGGMDIEITRANEYDY
WGQGTQVTVSS

CDR1:
                                                           SEQ ID NO: 42
GRTLGRYSMA

CDR2:
                                                           SEQ ID NO: 43
AINWSGGSTY

CDR3:

GGMDIEITRANEYDY

SEQ ID NO: 44 hC4Nb8

SEQ ID NO: 45

QVQLVESGGGLVQTGDSLRLSCAASGRTFSRYAMGWFRQAPGKERELVAAINWSG
GSTYYADFAKGRFTISRDNAKNMLYLRMSSLKPEDTAVYYCAAGGPEVEITRANEYD
YWGQGTQVTVSS

CDR1:

GRTFSRYAMG

SEQ ID NO: 46

CDR2:

AINWSGGSTY

SEQ ID NO: 47

CDR3:

GGPEVEITRANEYDY

SEQ ID NO: 48

D121

SEQ ID NO: 49

QVQLVESGGGLVQAGGSLRLSCVVSGSTFSDYAMGWYRQAAGEQRELVAAIYSTGR
TNYIDSVKGRFTISRDNAKTTVYLQMNSLKPEDTAVYYCNLLGATTMINTKWGQGTQV
TVSS

CDR1:

SGSTFSDYAMG

SEQ ID NO: 50

CDR2:

AIYSTGRTN

SEQ ID NO: 51

CDR3:

LGATTMINTK

SEQ ID NO: 52

DI62

SEQ ID NO: 53

QVQLVESGGGLVQAGGSLRLSCAASGRTFSDYTMGWFRQAPGKEREFVAGLSTGG
SFTRYAASVEGRFTISRDNAKTTVYLQMNNLQPEDTAVYYCAADFTPYGTNWSRFRE
ARDHYWGQGTQVTVSS

CDR1:

SGRTFSDYTMG

SEQ ID NO: 54

CDR2:

GLSTGGSFTR

SEQ ID NO: 55

CDR3:

DFTPYGTNWSRFREARDHY

SEQ ID NO: 56

EWE-hC3Nb1

SEQ ID NO: 57

MEWEQVQLVETGGGLVQAGGSLRLSCAASGSIFSINAMGWFRQAPGKEREFVATIN
RSGGRTYYADSVKGRFTISRDNGKNMVYLQMHSLKPEDTAIYYCAAGTGWSPQTDN
EYNYWGQGTQVTVSS

CDR1:

SGSIFSINAMG

SEQ ID NO: 58

CDR2:

TINRSGGRTY

SEQ ID NO: 59

-continued

CDR3:
SEQ ID NO: 60
GTGWSPQTDNEYNY

IgG-Fc-hC3Nb1
SEQ ID NO: 61
APLEPKSSDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNK
ALPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQKS
LSLSPGAQVQLVETGGGLVQAGGSLRLSCAASGSIFSINAMGWFRQAPGKEREFVAT
INRSGGRTYYADSVKGRFTISRDNGKNMVYLQMHSLKPEDTAIYYCAAGTGWSPQTD
NEYNYWGQGTQVTVSS

CDR1:
SEQ ID NO: 62
SGSIFSINAMG

CDR2:
SEQ ID NO: 63
TINRSGGRTY

CDR3:
SEQ ID NO: 64
GTGWSPQTDNEYNY

Polypeptide linker:
SEQ ID NO: 65
GGGGSGGGGS hC4Nb5
SEQ ID NO: 66
QVQLVETGGGLVQPGGSLRLSCAASGRTFNKNPMAWFRQPPGQERDLVAAISWSG
DSTNYANSVQGRFTISRNNAQRTVSLSMNNLKPEDTAVYYCAAVGRTDYSPNSLALT
AQNYDYWGQGTQVTVSS

CDR1:
SEQ ID NO: 67
GRTFNKNPMA

CDR2:
SEQ ID NO: 68
AISWSGDSTN

CDR3:
SEQ ID NO: 69
VGRTDYSPNSLALTAQNYD hC4Nb4
SEQ ID NO: 70
QVQLVETGGGLVEAGGSLRISCAASGRYAMGWFRQAPGNERDFVAAISRSGDSANY
ADTAWGRFTISRDNAQNTMTLQMNSLKPEDTAVYYCAAKAGLYSLNSLFLRSQEYTY
WGQGTQVTVSS

CDR1:
SEQ ID NO: 71
GRYAMG

CDR2:
SEQ ID NO: 72
AISRSGDSAN

CDR3:
SEQ ID NO: 73
KAGLYSLNSLFLRSQEYTY

Mouse C3 C345c domain UniProtKB - P01027 (CO3_MOUSE)
SEQ ID NO: 74
ENCFMQQSQEKINLNVRLDKACEPGVDYVYKTELTNIELLDDFDEYTMTIQQVIKSGS
DEVQAGQQRKFISHIKCRNALKLQKGKKYLMWGLSSDLWGEKPNTSYIIGKDTWVEH
WPEAEECQDQKYQKQCEELGAFTESMVVYGCPN Mouse C3, partial part of protein

SEQ ID NO: 75

EKINLNVRLDKAC
PEAEECQDQKYQKQCEELGAFTESMVVYGCPN pNSL270

SEQ ID NO: 76

QVQLVESGGGLVQAGGSLR
LSCVASASTLDIYTYAMAWF
RQAPGKRREFVAAISRNGYS
TYYADSVKGRFTISKLNAKN
TLYLQMNSLEPEDTAAYYCA
ADRTTEVVDREDDYGYWGQG
TQVTVSS

CDR1:

SEQ ID NO: 77

ASTLDIYTYAMA

CDR2:

SEQ ID NO: 78

AISRNGYSTY

CDR3:

SEQ ID NO: 79

DRTTEVVDREDDYGY

Human C4B alpha chain UniProtKB - P0C0L5 (CO4B_HUMAN) residues 680-1446

SEQ ID NO: 80

NVNFQKAINEKLGQYASPTAKRCCQDGVTRLPMMRSCEQRAARVQQPDCREPFLSC
CQFAESLRKKSRDKGQAGLQRALEILQEEDLIDEDDIPVRSFFPENWLWRVETVDRF
QILTLWLPDSLTTWEIHGLSLSKTKGLCVATPVQLRVFREFHLHLRLPMSVRRFEQLEL
RPVLYNYLDKNLTVSVHVSPVEGLCLAGGGGLAQQVLVPAGSARPVAFSVVPTAATA
VSLKVVARGSFEFPVGDAVSKVLQIEKEGAIHREELVYELNPLDHRGRTLEIPGNSDP
NMIPDGDFNSYVRVTASDPLDTLGSEGALSPGGVASLLRLPRGCGEQTMIYLAPTLAA
SRYLDKTEQWSTLPPETKDHAVDLIQKGYMRIQQFRKADGSYAAWLSRGSSTWLTAF
VLKVLSLAQEQVGGSPEKLQETSNWLLSQQQADGSFQDLSPVIHRSMQGGLVGNDE
TVALTAFVTIALHHGLAVFQDEGAEPLKQRVEASISKASSFLGEKASAGLLGAHAAAIT
AYALTLTKAPADLRGVAHNNLMAMAQETGDNLYWGSVTGSQSNAVSPTPAPRNPSD
PMPQAPALWIETTAYALLHLLLHEGKAEMADQAAAWLTRQGSFQGGFRSTQDTVIAL
DALSAYWIASHTTEERGLNVTLSSTGRNGFKSHALQLNNRQIRGLEEELQFSLGSKIN
VKVGGNSKGTLKVLRTYNVLDMKNTTCQDLQIEVTVKGHVEYTMEANEDYEDYEDE
LPAKDDPDAPLQPVTPLQLFEG

Human C4b-A alpha chain UniProtKB - P0C0L4 (C04A_HUMAN) residues 757-1446

SEQ ID NO: 81

ALEILQEEDLIDEDDIPVRSFFPENWLWRVETVDRFQILTLWLPDSLTTWEIHGLSLSKT
KGLCVATPVQLRVFREFHLHLRLPMSVRRFEQLELRPVLYNYLDKNLTVSVHVSPVEG
LCLAGGGGLAQQVLVPAGSARPVAFSVVPTAAAAVSLKVVARGSFEFPVGDAVSKVL
QIEKEGAIHREELVYELNPLDHRGRTLEIPGNSDPNMIPDGDFNSYVRVTASDPLDTLG
SEGALSPGGVASLLRLPRGCGEQTMIYLAPTLAASRYLDKTEQWSTLPPETKDHAVD
LIQKGYMRIQQFRKADGSYAAWLSRDSSTWLTAFVLKVLSLAQEQVGGSPEKLQETS
NWLLSQQQADGSFQDPCPVLDRSMQGGLVGNDETVALTAFVTIALHHGLAVFQDEG
AEPLKQRVEASISKANSFLGEKASAGLLGAHAAAITAYALTLTKAPVDLLGVAHNNLMA
MAQETGDNLYWGSVTGSQSNAVSPTPAPRNPSDPMPQAPALWIETTAYALLHLLLHE
GKAEMADQASAWLTRQGSFQGGFRSTQDTVIALDALSAYWIASHTTEERGLNVTLSS
TGRNGFKSHALQLNNRQIRGLEEELQFSLGSKINVKVGGNSKGTLKVLRTYNVLDMK
NTTCQDLQIEVTVKGHVEYTMEANEDYEDYEDELPAKDDPDAPLQPVTPLQLFEG

Human C4b-B alpha chain UniProtKB - P0C0L5 (CO4B_HUMAN) residues 757-1446

SEQ ID NO: 82

ALEILQEEDLIDEDDIPVRSFFPENWLWRVETVDRFQILTLWLPDSLTTWEIHGLSLSKT
KGLCVATPVQLRVFREFHLHLRLPMSVRRFEQLELRPVLYNYLDKNLTVSVHVSPVEG
LCLAGGGGLAQQVLVPAGSARPVAFSVVPTAATAVSLKVVARGSFEFPVGDAVSKVL
QIEKEGAIHREELVYELNPLDHRGRTLEIPGNSDPNMIPDGDFNSYVRVTASDPLDTLG
SEGALSPGGVASLLRLPRGCGEQTMIYLAPTLAASRYLDKTEQWSTLPPETKDHAVD
LIQKGYMRIQQFRKADGSYAAWLSRGSSTWLTAFVLKVLSLAQEQVGGSPEKLQETS
NWLLSQQQADGSFQDLSPVIHRSMQGGLVGNDETVALTAFVTIALHHGLAVFQDEGA
EPLKQRVEASISKASSFLGEKASAGLLGAHAAAITAYALTLTKAPADLRGVAHNNLMA
MAQETGDNLYWGSVTGSQSNAVSPTPAPRNPSDPMPQAPALWIETTAYALLHLLLHE
GKAEMADQAAAWLTRQGSFQGGFRSTQDTVIALDALSAYWIASHTTEERGLNVTLSS
TGRNGFKSHALQLNNRQIRGLEEELQFSLGSKINVKVGGNSKGTLKVLRTYNVLDMK
NTTCQDLQIEVTVKGHVEYTMEANEDYEDYEDELPAKDDPDAPLQPVTPLQLFEG

Mouse Complement C4 beta chain - P01029 residues 20-673

SEQ ID NO: 83

KPRLLLFSPSVVNLGTPLSVGVQLLDAPPGQEVKGSVFLRNPKGGSCSPKKDFKLSS
GDDFVLLSLEVPLEDVRSCGLFDLRRAPHIQLVAQSPWLRNTAFKATETQGVNLLFSS

-continued

RRGHIFVQTDQPIYNPGQRVRYRVFALDQKMRPSTDFLTITVENSHGLRVLKKEIFTST
SIFQDAFTIPDISEPGTWKISARFSDGLESNRSTHFEVKKYVLPNFEVKITPWKPYILMV
PSNSDEIQLDIQARYIYGKPVQGVAYTRFALMDEQGKRTFLRGLETQAKLVEGRTHISI
SKDQFQAALDKINIGVRDLEGLRLYAATAVIESPGGEMEEAELTSWRFVSSAFSLDLS
RTKRHLVPGAHFLLQALVQEMSGSEASNVPVKVSATLVSGSDSQVLDIQQSTNGIGQ
VSISFPIPPTVTELRLLVSAGSLYPAIARLTVQAPPSRGTGFLSIEPLDPRSPSVGDTFIL
NLQPVGIPAPTFSHYYYMIISRGQIMAMGREPRKTVTSVSVLVDHQLAPSFYFVAYFY
HQGHPVANSLLINIQSRDCEGKLQLKVDGAKEYRNADMMKLRIQTDSKALVALGAVD
MALYAVGGRSHKPLDMSKVFEVINSYNVGCPGGGDDALQVFQDAGLAFSDGDRLT
QTREDLSCPKEKKS

Mouse Complement C4 alpha chain - P01029 residues 678-1443     SEQ ID NO: 84

NVNFQKAVSEKLGQYSSPDAKRCCQDGMTKLPMKRTCEQRAARVPQQACREPFLS
CCKFAEDLRRNQTRSQAHLARNNHNMLQEEDLIDEDDILVRTSFPENWLWRVEPVDS
SKLLTVWLPDSMTTWEIHGVSLSKSKGLCVAKPTRVRVFRKFHLHRLPISIRRFEQFE
LRPVLYNYLNDDVAVSVHVTPVEGLCLAGGGMMAQQVTVPAGSARPVAFSVVPTAA
ANVPLKVVARGVFDLGDAVSKILQIEKEGAIHREELVYNLDPLNNLGRTLEIPGSSDPNI
VPDGDFSSLVRVTASEPLETMGSEGALSPGGVASLLRLPQGCAEQTMIYLAPTLTASN
YLDRTEQWSKLSPETKDHAVDLIQKGYMRIQQFRKNDGSFGAWLHRDSSTWLTAFVL
KILSLAQEQVGNSPEKLQETASWLLAQQLGDGSFHDCPVIHRAMQGGLVGSDETVA
LTAFVVIALHHGLDVFQDDDAKQLKNRVEASITKANSFLGQKASAGLLGAHAAAITAYA
LTLTKASEDLRNVAHNSLMAMAEETGEHLYWGLVLGSQDKVVLRPTAPRSPTEPVPQ
APALWIETTAYALLHLLREGKGKMADKAASWLTHQGSFHGAFRSTQDTVVTLDALS
AYWIASHTTEEKALNVTLSSMGRNGLKTHGLHLNNHQVKGLEEELKFSLGSTISVKVE
GNSKGTLKILRTYNVLDMKNTTCQDLQIEVKVTGAVEYAWDANEDYEDYYDMPAADD
PSVPLQPVTPLQLFEGRRS

SEQ ID NO: 85

EAPKVVEEQESRVQYTVCIWRNGKLGLSGMAIADITLLSGFHALRADLEKLTSLSDRY
VSHFETDGPHVLLYFDSVPTTRECVGFGASQEVVVGLVQPSSAVLYDYYSPDHKCSV
FYAAPTKSQLLATLCSGDVCQCAEGKCPRLLRSLERRVEDKDGYRMRFACYYPRVE
YGFTVKVLREDGRAAFRLFESKITQVLHFRKDTMASIGQTRNFLSRASCRLRLEPNKE
YLIMGMDGETSDNKGDPQYLLDSNTWIEEMPSEQMCKSTRHRAACFQLKDFLMEFS
SRGCQV

---

The invention claimed is:

1. A single domain antibody capable of specifically binding to an epitope of a human and/or mouse C1q complement factor, wherein the single domain antibody comprises a complementarity determining region-1 (CDR1), a complementarity determining region-2 (CDR2), and a complementarity determining region-3 (CDR3); wherein:

(a) the CDR1 comprises the amino acid sequence of SEQ ID NO: 10, the CDR2 comprises the amino acid sequence of SEQ ID NO: 11, and the CDR3 comprises the amino acid sequence of SEQ ID NO: 12;

(b) the CDR1 comprises the amino acid sequence of SEQ ID NO: 14, the CDR2 comprises the amino acid sequence of SEQ ID NO: 15, and the CDR3 comprises the amino acid sequence of SEQ ID NO: 16;

(c) the CDR1 comprises the amino acid sequence of SEQ ID NO: 18, the CDR2 comprises the amino acid sequence of SEQ ID NO: 19, and the CDR3 comprises the amino acid sequence of SEQ ID NO: 20;

(d) the CDR1 comprises the amino acid sequence of SEQ ID NO: 22, the CDR2 comprises the amino acid sequence of SEQ ID NO: 23, and the CDR3 comprises the amino acid sequence of SEQ ID NO: 24;

(e) the CDR1 comprises the amino acid sequence of SEQ ID NO: 26, the CDR2 comprises the amino acid sequence of SEQ ID NO: 27, and the CDR3 comprises the amino acid sequence of SEQ ID NO: 28;

(f) the CDR1 comprises the amino acid sequence of SEQ ID NO: 30, the CDR2 comprises the amino acid sequence of SEQ ID NO: 31, and the CDR3 comprises the amino acid sequence of SEQ ID NO: 32;

(g) the CDR1 comprises the amino acid sequence of SEQ ID NO: 34, the CDR2 comprises the amino acid sequence of SEQ ID NO: 35, and the CDR3 comprises the amino acid sequence of SEQ ID NO: 36; or (h) the CDR1 comprises the amino acid sequence of SEQ ID NO: 38, the CDR2 comprises the amino acid sequence of SEQ ID NO: 39, and the CDR3 comprises the amino acid sequence of SEQ ID NO: 40.

2. The single domain antibody according to claim 1, wherein said antibody is fused to another entity or moiety.

3. The single domain antibody according to claim 2, wherein said another entity or moiety binds a cancer-specific marker, a pathogenic marker, a tissue-specific marker or an organ-specific marker.

4. The single domain antibody according to claim 1, wherein the said antibody binds said complement factor with an affinity corresponding to a $K_D$ of about $10^{-6}$ M or less.

5. A composition that comprises the single domain antibody of claim 1.

6. The composition of claim 5, further comprising an additional entity or moiety.

7. The composition of claim 6, wherein the single domain antibody and the additional entity or moiety are fused by a linker.

8. The composition of claim 6, wherein the additional entity or moiety is albumin.

9. The composition of claim 7, wherein the additional entity or moiety is a binding moiety that binds to a cancer-specific marker, a pathogenic marker, a tissue-specific marker or an organ-specific marker.

10. A single domain antibody capable of specifically binding to an epitope of a human and/or mouse C1q complement factor, wherein the single domain antibody comprises a complementarity determining region-1 (CDR1), a complementarity determining region-2 (CDR2), and a complementarity determining region-3 (CDR3), wherein the CDR1 comprises the amino acid sequence of SEQ ID NO: 18 or a functional variant thereof, wherein the functional variant comprises a single amino acid substitution, wherein the CDR2 comprises the amino acid sequence of SEQ ID NO: 19 or a functional variant thereof, wherein the functional variant comprises a single amino acid substitution, and wherein the CDR3 comprises the amino acid sequence of SEQ ID NO: 20.

11. The single domain antibody according to claim 10, wherein said antibody is fused to another entity or moiety.

12. The single domain antibody according to claim 11, wherein said another entity or moiety binds a cancer-specific marker, a pathogenic marker, a tissue-specific marker or an organ-specific marker.

13. The single domain antibody according to claim 10, wherein the said antibody binds said complement factor with an affinity corresponding to a $K_D$ of about $10^{-6}$ M or less.

14. A composition that comprises the single domain antibody of claim 10.

15. The composition of claim 14, wherein the single domain antibody is fused to an additional entity or moiety.

16. The composition of claim 15, wherein the single domain antibody and the additional entity or moiety are fused by a linker.

17. The composition of claim 15, wherein the additional entity or moiety is albumin.

18. The composition of claim 15, wherein the additional entity or moiety is a binding moiety that binds to a cancer-specific marker, a pathogenic marker, a tissue-specific marker or an organ-specific marker.

* * * * *